(12) United States Patent
Hunt et al.

(10) Patent No.: US 7,534,622 B2
(45) Date of Patent: May 19, 2009

(54) ELECTRON TRANSFER DISSOCIATION FOR BIOPOLYMER SEQUENCE MASS SPECTROMETRIC ANALYSIS

(75) Inventors: Donald F. Hunt, Charlottesville, VA (US); Joshua J. Coon, Charlottesville, VA (US); John Edward Philip Syka, Charlottesville, VA (US); Jarrod A. Marto, Wayland, MA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 779 days.

(21) Appl. No.: 11/079,147

(22) Filed: Mar. 14, 2005

(65) Prior Publication Data
US 2005/0199804 A1    Sep. 15, 2005

Related U.S. Application Data

(60) Provisional application No. 60/552,876, filed on Mar. 12, 2004, provisional application No. 60/572,884, filed on May 20, 2004, provisional application No. 60/599,341, filed on Aug. 6, 2004.

(51) Int. Cl.
*G01N 24/00* (2006.01)
(52) U.S. Cl. .................................... 436/173
(58) Field of Classification Search ........................ None
See application file for complete search history.

(56) References Cited

U.S. PATENT DOCUMENTS

2002/0092980 A1    7/2002    Park

2002/0166958 A1    11/2002    Afeyan et al.

FOREIGN PATENT DOCUMENTS

EP    0 409 362 A2    1/1991

OTHER PUBLICATIONS

Wells et al. ""Dueling" ESI: Instrumentation to Study Ion/Ion Reactions of Electrospray-generated Cations and Anions", J Am Soc Mass Spectrom 2002, 13, 614-622.*
Zubarev et al. "Electron Capture Dissociation of Multiply Charged Protein Cations. A Nonergodic Process", J. Am. Chem. Soc. 1998, 120, 3265-3266.*
Douglas et al. "Linear Ion Traps in Mass Spectrometry", Mass Spectrometry Reviews, 2005, 24, 1-29.*
Herron et al., "Gas-Phase Electron Transfer Reactions from Multiply-Charged Anions to Rare Gas Cations", J. Am. Chem. Soc., vol. 117, 1995, pp. 11555-11562.
Stephenson et al., "Ion/Ion Proton Transfer Reactions for Protein Mixture Analysis", Anal. Chem., vol. 68, 1996, pp. 4026-4032.

(Continued)

*Primary Examiner*—Yelena G Gakh
(74) *Attorney, Agent, or Firm*—Barnes & Thornburg LLP

(57) ABSTRACT

The present invention relates to a new method for fragmenting ions in a mass spectrometer through the use of electron transfer dissociation, and for performing sequence analysis of peptides and proteins by mass spectrometry. In the case of peptides, the invention promotes fragmentation along the peptide backbone and makes it possible to deduce the amino acid sequence of the sample, including modified amino acid residues, through the use of an RF field device.

35 Claims, 26 Drawing Sheets

OTHER PUBLICATIONS

Stephenson et al., "Anion Effects on Storage and Resonance Ejection of High Mass-to-Charge Cations in Quadrupole Ion Trap Mass Spectrometry", *Anal. Science*, vol. 69, 1997, pp. 3760-3766.

Stephenson et al., "Ion-Ion Proton Transfer Reactions of Bio-Ions Involving Noncovalent Interactions: Holomyoglobin", *J. Am. Soc. Mass. Spectrometry*, vol. 8, 1997, pp. 637-644.

McLuckey et al., "Ion/Ion Proton-Transfer Kinetics: Implications for Analysis of Ions Derived from Electrospray of Protein Mixtures", *Anal. Chem.*, vol. 70, 1998, pp. 1198-1202.

Stephenson et al., "Simplification of Product Ion Spectra Derived from Multiply Charged Ions via Ion/Ion Chemistry", *Anal. Chem.*, vol. 70, 1998, pp. 3533-3544.

McLuckey et al., "Ion/Ion Chemistry of High-Mass Multiply Charged Ions", *Mass Spectrometry Reviews*, vol. 17, 1998, pp. 369-407.

Loo et al., "Proton Transfer Reaction Studies of Multiply Charge Proteins in a High Mass-to-Charge Ratio Quadrupole Mass Spectrometry", *J. Am. Soc. Mass Spectrometry*, vol. 5, 1994, pp. 1064-1071.

Syka et al., "Peptide and Protein Sequence Analysis by Electron Transfer Dissociation Mass Spectrometry", *PNAS*, vol. 101, No. 26, Jun. 2004, pp. 9528-9533.

McLafferty et al., "Electron Capture Dissociation of Multiply Charged Protein Cations. A Nonergodic Process", *J. Am. Chem. Soc.*, vol. 120, 1998, pp. 3265-3266.

Schwartz et al., "A Two-Dimensional Quadrupole Ion Trap Mass Spectrometer", *J. Am. Soc. Mass Spectrometry*, vol. 13, 2002, pp. 659-669.

Martin et al., "Subfemtomole MS and MS/MS Peptide Sequence Analysis Using Nano-HPLC Micro-ESI Fourier Transform Ion Cyclotron Resonance Mass Spectrometry", *Anal. Chem.*, vol. 72, 2000, pp. 4266-4274.

Ficarro et al., "Phosphoproteome Analysis by Mass Spectrometry and its Application to *Saccharomyces cerevisiae*", *J. Am. Chem. Soc.*, vol. 20, 2002, pp. 301-305.

Eng et al., "An Approach to Correlate Tandem Mass Spectral Data of Peptides with Amino Acid Sequence in a Protein Database", *J. Am. Soc. Mass Spectrometry*, vol. 5, 1994, pp. 976-989.

Aebersold, Ruedi et al.; "Mass Spectrometry in Proteomics," Chem. Rev, vol. 101, No. 2, Feb. 2001, pp. 269-295.

Coon, Joshua J. et al., "Electron Transfer Dissociation of Peptide Anions," American Society for Mass Spectrometry, vol. 16, Nr. 6, Jun. 2005, pp. 880-882.

\* cited by examiner

Fig. 3 NICI Source Gas Inlet Connections Used For The Initial ETD Experiments

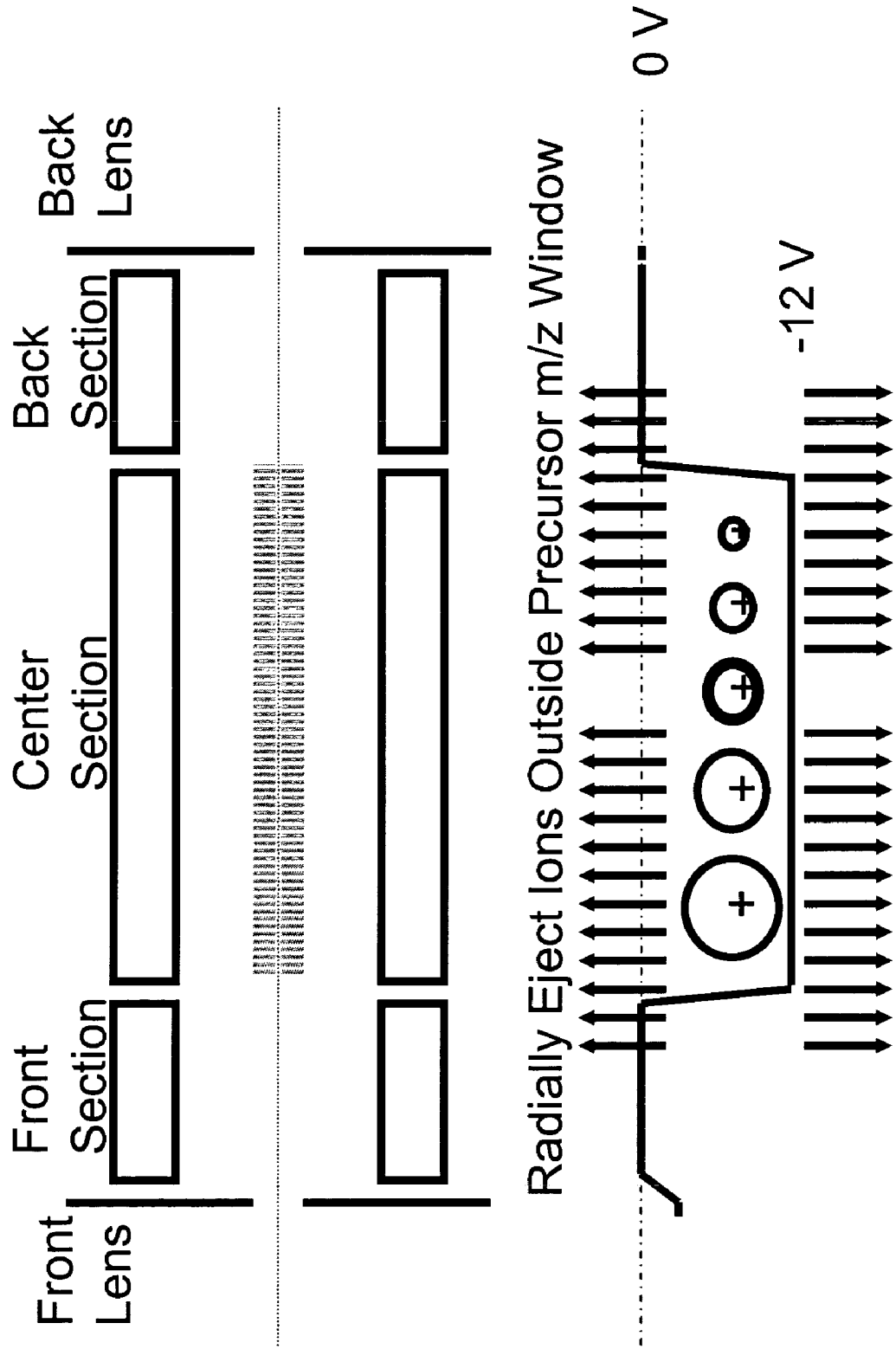

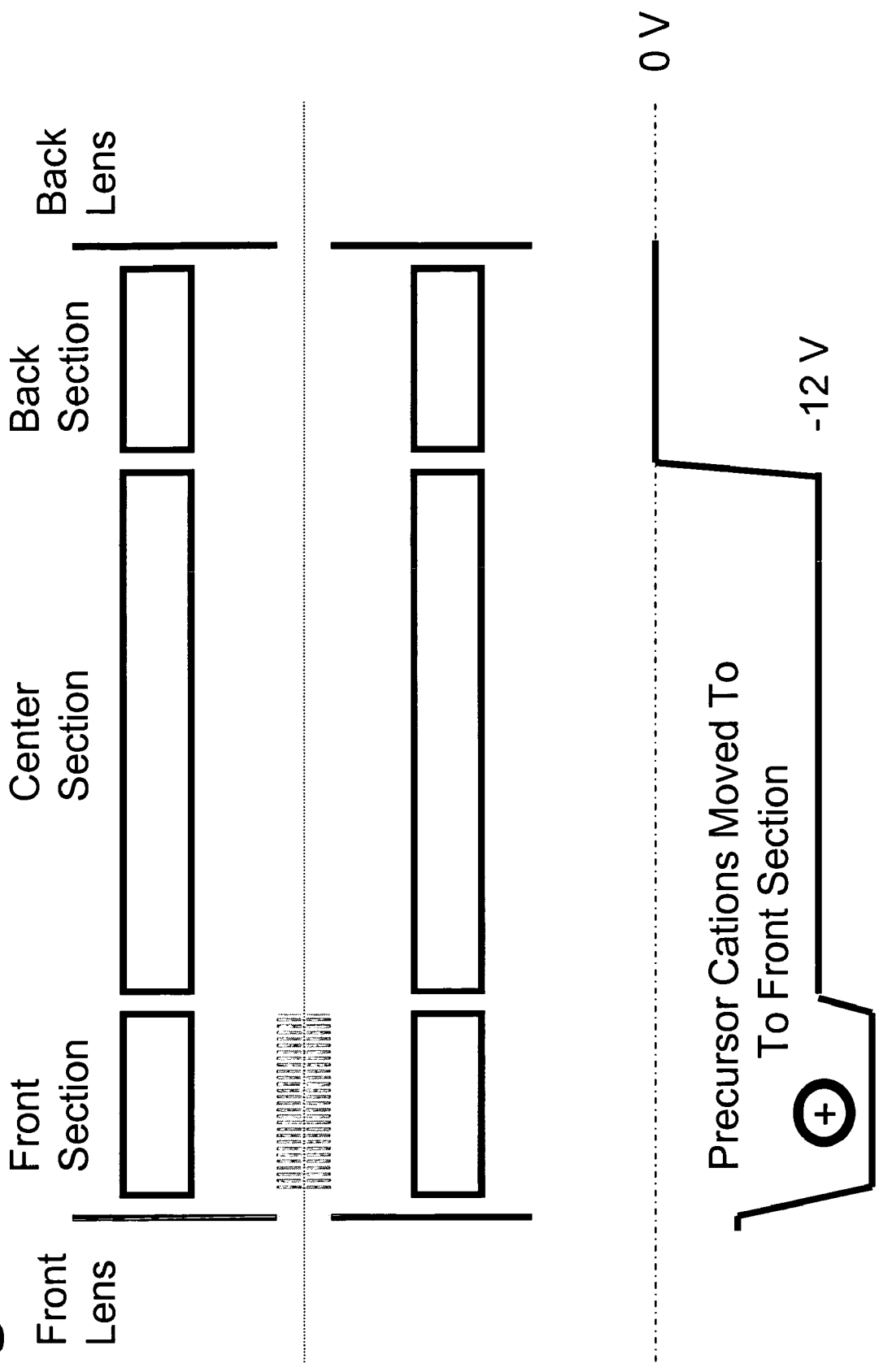

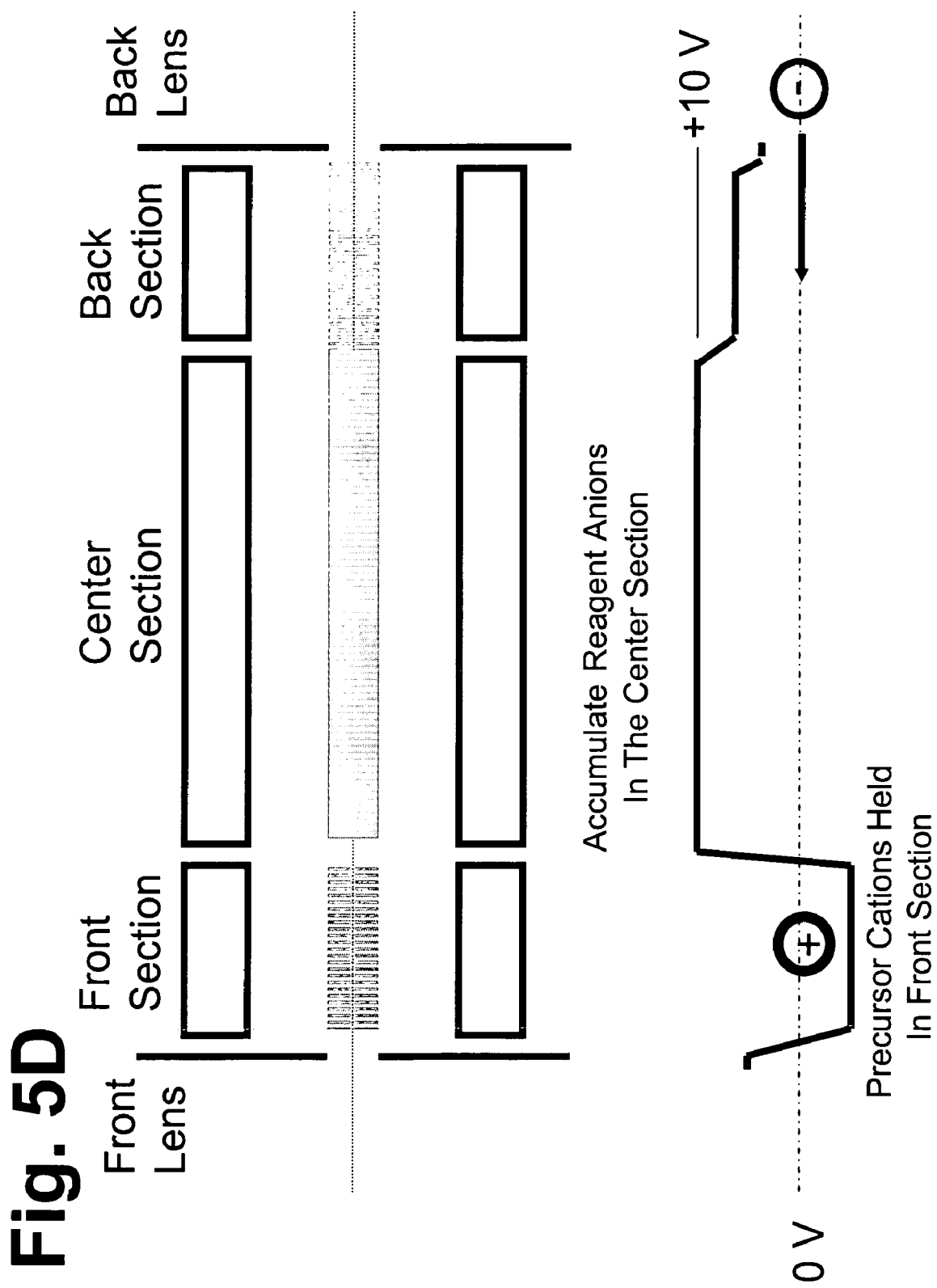

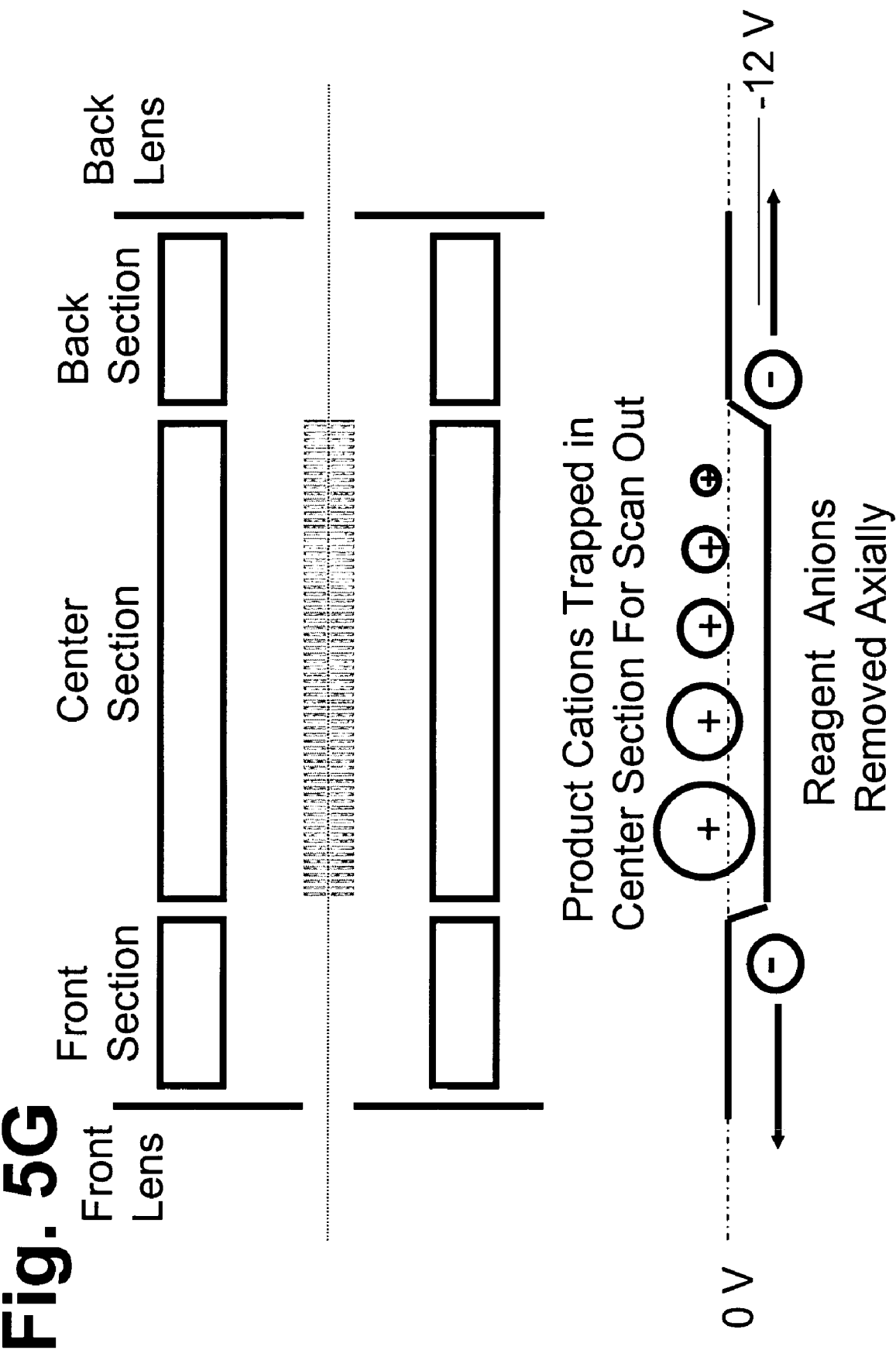

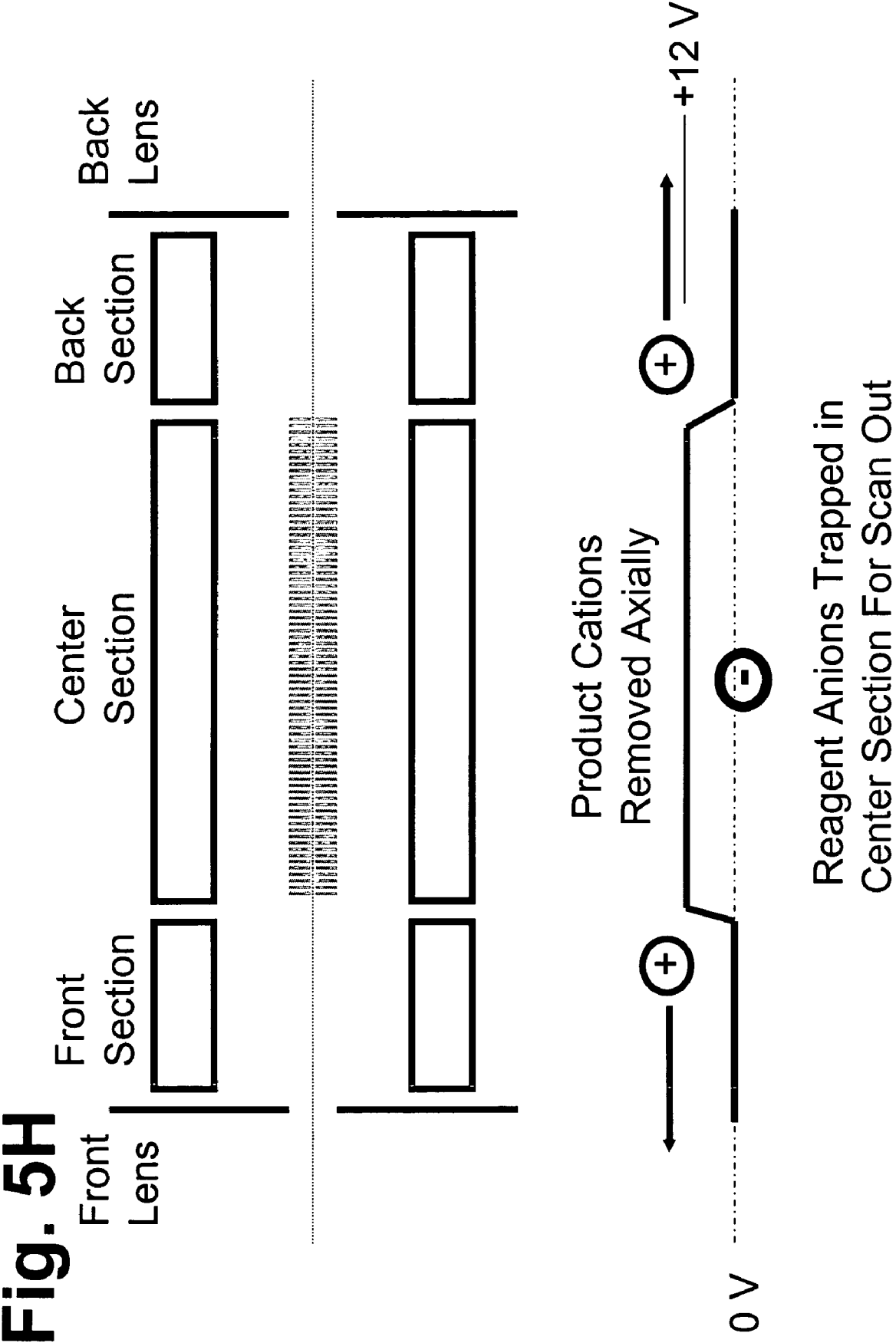

C = 181 337 504 660 827 983 1150 1306 1473 <u>1570</u> <u>1733</u> 1907

Y R S* R S* R S* R S* P Y R$_{-OCH_3}$

1907 <u>1725</u> <u>1569</u> <u>1402</u> <u>1246</u> <u>1079</u> <u>923</u> <u>756</u> 600 433 <u>336</u> <u>173</u> = z

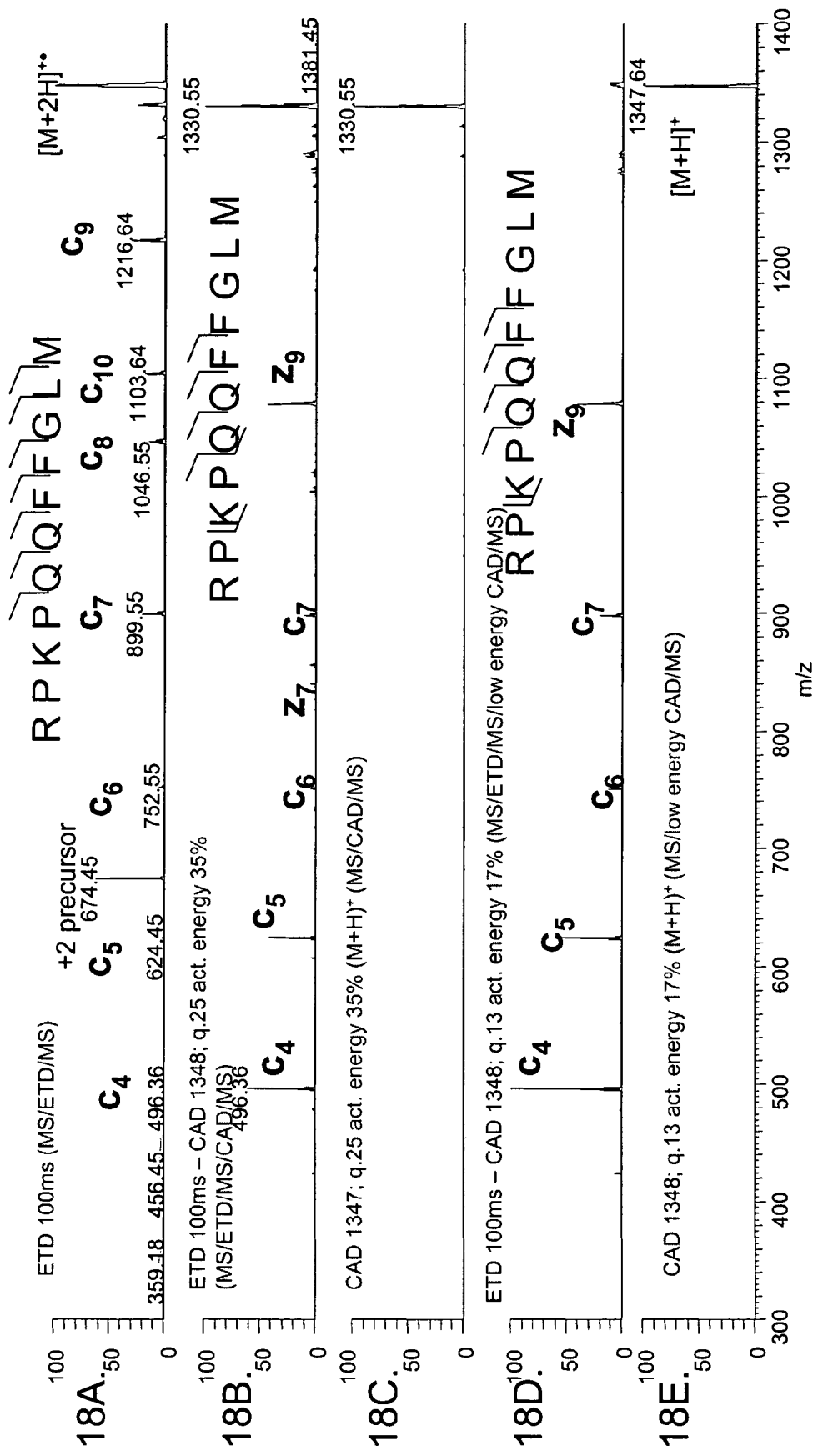

SEQUENCE LISTING

```
<160> NUMBER OF SEQ ID NOS: 72

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide for amino acid sequencing
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 1

Leu Pro Ile Ser Ala Ser His Ser Ser Lys Thr Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide for sequence analysis

<400> SEQUENCE: 2

Asp Arg Val Tyr Ile His Pro Phe His Leu
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic
```

```
<220> FEATURE:
<221> NAME/KEY: MOD_RES
<222> LOCATION: (10)..(10)
<223> OTHER INFORMATION: PHOSPHORYLATION

<400> SEQUENCE: 3

Ala Pro Val Ala Pro Arg Pro Ala Ala Thr Pro Asn Leu Ser Lys
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 4

Asp Arg Ser Pro Ile Arg Gly Ser Pro Arg
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 5

Glu Arg Ser Leu Ser Arg Glu Arg
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (9)..(9)
<223> OTHER INFORMATION: PHOSPHORYLATION

<400> SEQUENCE: 6

Arg Leu Pro Ile Phe Asn Arg Ile Ser Val Ser Glu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (1)..(1)
```

```
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 7

Ser Arg Ser Phe Asp Tyr Asn Tyr Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 8

Arg Ser Ser Gly Leu Ser Arg His Arg
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION

<400> SEQUENCE: 9

Arg Ser Met Ser Leu Leu Gly Tyr Arg
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION

<400> SEQUENCE: 10

Gly Ser Pro His Tyr Phe Ser Pro Phe Arg Pro Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
```

```
<222> LOCATION: (3)..(3)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 11

Asp Arg Ser Pro Ile Arg Gly Ser Pro Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 12

Arg Arg Ser Pro Ser Pro Tyr Tyr Ser Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 13

Ser Arg Val Ser Val Ser Pro Gly Arg
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 14

Ala Pro Val Ala Ser Pro Arg Pro Ala Ala Thr Pro Asn Leu Ser Lys
1               5                   10                  15

<210> SEQ ID NO 15
<211> LENGTH: 8
<212> TYPE: PRT
```

```
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: METHYLATION

<400> SEQUENCE: 15

Glu Arg Ser Leu Ser Arg Glu Arg
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 16

Arg Tyr Arg Ser Arg Ser Arg Ser Pro Tyr Arg Arg Ile
1               5                   10              15

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 17

Arg Ser Tyr Ser Pro Asp Gly Lys Glu Ser Pro Ser Asp Lys Lys Ser
1               5                   10                  15

<210> SEQ ID NO 18
<211> LENGTH: 11
<212> TYPE: PRT
```

<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 18

Arg Lys Arg Ser Tyr Ser Pro Asp Gly Lys Glu
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 19

Lys Thr Asp Ser Glu Lys Pro Phe Arg Gly Ser Gln Ser Pro Lys Arg
1               5                   10                  15

Tyr

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 20

Lys Ser Arg Glu Ser Val Asp Ser Arg Asp Ser Ser His Ser Arg Glu
1               5                   10                  15

Arg Ser

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide for sequence analysis
<220> FEATURE:

```
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 21

Lys Ser Arg Glu Ser Val Asp Ser Arg Asp Ser Ser His Ser Arg Glu
1               5                   10                  15

Arg Ser

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 22

Arg Arg Arg Ser Ser Ser Pro Phe Leu Ser Lys Arg Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 23

Arg Ser Gly Ser Tyr Ser Gly Arg Ser Pro Ser Pro Tyr Gly Arg Arg
1               5                   10                  15

<210> SEQ ID NO 24
<211> LENGTH: 16
<212> TYPE: PRT
<213> ORGANISM: Artificial Sequence
<220> FEATURE:
```

```
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 24

Arg Ser Gly Ser Tyr Ser Gly Arg Ser Pro Ser Pro Tyr Gly Arg Arg
 1               5                  10                  15

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 25

Arg Ser Arg Ser His Ser Pro Met Ser Asn Arg Arg
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 26

Arg Arg Ser Arg Ser Ile Ser Leu Arg Arg Ser
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
```

```
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 27

Arg Ser Arg Ser Ala Ser Leu Arg Arg Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 28

Arg Lys Arg Ser Ile Ser Glu Ser Ser Arg Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 29

Arg Ser Ile Ser Glu Ser Ser Arg Ser Gly Lys Arg Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 30
```

```
Arg Arg Glu Arg Ser Leu Ser Arg Asp Arg Asn
1               5                   10
```

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 31

```
Arg Glu Arg Ser Leu Ser Arg Asp Arg Asn
1               5                   10
```

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 32

```
Arg Lys Arg Ser Pro Ser Pro Ser Pro Thr Pro Glu Ala Lys Lys
1               5                   10                  15
```

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 33

```
Arg Ser Arg Ser Arg Ser Tyr Glu Arg Arg
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES

```
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 34

Arg Arg Arg Ser Pro Ser Pro Ala Pro Pro Arg Arg Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 35

Lys Arg Glu Ser Pro Ser Pro Ala Pro Lys Pro Arg Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 36

Lys Arg Arg Thr Ala Ser Pro Pro Pro Pro Lys Arg Arg
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 37

Lys Arg Arg Ser Pro Ser Leu Ser Ser Lys His
1               5                   10

<210> SEQ ID NO 38
<211> LENGTH: 11
<212> TYPE: PRT
```

```
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 38

Arg Arg Arg Thr Pro Ser Pro Pro Arg Arg
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 39

Arg Arg Arg Ser Pro Ser Pro Pro Pro Thr Arg Arg
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 40

Arg Arg Pro Ser Pro Arg Arg Pro Ser Pro Arg Arg Arg
1               5                   10

<210> SEQ ID NO 41
<211> LENGTH: 18
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION

<400> SEQUENCE: 41

Arg Ser Ser Ala Ser Leu Ser Gly Ser Ser Ser Ser Ser Ser
1               5                   10                  15

Arg Ser
```

```
<210> SEQ ID NO 42
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION

<400> SEQUENCE: 42

Arg Arg Ala Ser Pro Ser Pro Pro Pro Lys Arg Arg
1               5                   10

<210> SEQ ID NO 43
<211> LENGTH: 19
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (14)..(14)
<223> OTHER INFORMATION: PHOSPHORYLATION

<400> SEQUENCE: 43

Arg Arg Val Ser His Ser Pro Pro Pro Lys Gln Arg Ser Ser Pro Val
1               5                   10                  15

Thr Lys Arg

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 44

Arg Arg Arg Thr Pro Thr Pro Pro Pro Arg Arg
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 45

Arg Glu Ser Arg Arg Ser Glu Ser Leu Ser Pro Arg Arg Glu
```

```
<210> SEQ ID NO 46
<211> LENGTH: 17
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 46

Arg Ser Arg Ser Gly Ser Arg Gly Arg Asp Ser Pro Tyr Gln Ser Arg
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 47

Arg Ser Arg Ser Gly Ser Arg Gly Arg Asp Ser Pro Tyr Gln Ser Arg
1               5                   10                  15

Gly

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 48

Arg Arg Glu Arg Ser Leu Ser Arg Glu Arg Asn
1               5                   10

<210> SEQ ID NO 49
```

```
<211> LENGTH: 10
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 49

Arg Glu Arg Ser Leu Ser Arg Glu Arg Asn
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 50

Arg Asn His Lys Pro Ser Arg Ser Phe Ser Arg Ser Arg Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 51

Lys Arg Lys Leu Ser Arg Ser Pro Ser Pro Arg Arg
1               5                   10

<210> SEQ ID NO 52
<211> LENGTH: 11
<212> TYPE: PRT
<213> ORGANISM: Artificial Sequence
<220> FEATURE:
```

```
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 52

Arg Lys Leu Ser Arg Ser Pro Ser Pro Arg Arg
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 53

Arg Arg Ser Arg Ser Ala Ser Arg Glu Arg Arg
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (9)..(9)
<223> OTHER INFORMATION: PHOSPHORYLATION

<400> SEQUENCE: 54

Arg Arg Ser Arg Ser Gly Thr Arg Ser Pro Lys Lys
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 55

Arg Gly Lys Lys Ser Arg Ser Pro Val Asp Leu Arg Gly
1               5                   10
```

```
<210> SEQ ID NO 56
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 56

Lys Arg Arg Ser Leu Ser Pro Lys Pro Arg Asp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 57

Arg Arg Arg Ser Pro Ser Pro Tyr Tyr Ser Arg Gly
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 58

Arg Arg His Ser His Ser His Ser Pro Met Ser Thr Arg Arg
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
```

```
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 59

Arg Ser Arg Ser Tyr Ser Arg Asp Tyr Arg Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 60

Lys Ala Arg Ser Val Ser Pro Pro Pro Lys Arg Ala
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 61

Arg Ser Tyr Ser Gly Ser Arg Ser Arg Ser Arg Ser
1               5                   10

<210> SEQ ID NO 62
<211> LENGTH: 17
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 62
```

```
Lys Arg Lys Ser Leu Ser Asp Ser Glu Ser Asp Ser Lys Ser Lys
1               5                   10                  15

Lys

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 63

Lys Arg Lys Ser Leu Ser Asp Ser Glu Ser Asp Ser Lys Ser
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 64

Arg Arg Ser Arg Ser His Ser Asp Asn Asp Arg Phe Lys His
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 65

Arg Arg Ser Arg Ser His Ser Asp Asn Asp Arg Phe Lys His
1               5                   10

<210> SEQ ID NO 66
<211> LENGTH: 13
<212> TYPE: PRT
<213> ORGANISM: Artificial Sequence
<220> FEATURE:
```

```
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 66

Arg Ser Arg Ser His Ser Asp Asn Asp Arg Phe Lys His
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION

<400> SEQUENCE: 67

Arg Ser Arg Ser Arg Asp Lys Glu Glu Arg Arg
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (3)..(3)
<223> OTHER INFORMATION: PHOSPHORYLATION

<400> SEQUENCE: 68

Arg Lys Ser Ile Leu His Thr Ile Arg
1               5

<210> SEQ ID NO 69
<211> LENGTH: 16
<212> TYPE: PRT
<213> ORGANISM: Artificial Sequence
<220> FEATURE:
<223> OTHER INFORMATION: Synthetic peptide for sequence analysis
<220> FEATURE:
<221> NAME/KEY: MOD_RES
<222> LOCATION: (8)..(8)
<223> OTHER INFORMATION: O-GlcNAc modification

<400> SEQUENCE: 69

Lys Lys Phe Glu Leu Leu Pro Thr Pro Pro Leu Ser Pro Ser Arg Arg
1               5                   10                  15

<210> SEQ ID NO 70
<211> LENGTH: 9
<212> TYPE: PRT
<213> ORGANISM: Artificial Sequence
```

```
<220> FEATURE:
<223> OTHER INFORMATION: Synthetic peptide for sequence analysis
<220> FEATURE:
<221> NAME/KEY: MOD_RES
<222> LOCATION: (5)..(5)
<223> OTHER INFORMATION: SULFATATION

<400> SEQUENCE: 70

Gly Arg Leu Gly Ser Arg Ala Gly Arg
1               5

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide for sequence analysis

<400> SEQUENCE: 71

Arg Pro Lys Pro Gln Phe Phe Gly Leu Met
1               5                   10

<210> SEQ ID NO 72
<211> LENGTH: 24
<212> TYPE: PRT
<213> ORGANISM: Artificial Sequence
<220> FEATURE:
<223> OTHER INFORMATION: Synthetic peptide for sequence analysis

<400> SEQUENCE: 72

Ser Tyr Ser Met Glu His Phe Arg Trp Gly Lys Pro Val Gly Lys Lys
1               5                   10                  15

Arg Arg Pro Val Arg Val Tyr Pro
            20
```

ELECTRON TRANSFER DISSOCIATION FOR BIOPOLYMER SEQUENCE MASS SPECTROMETRIC ANALYSIS

RELATED APPLICATIONS

This application claims priority under 35 USC §119(e) to U.S. Provisional Application Ser. Nos. 60/552,876, filed Mar. 12, 2004, 60/572,884, filed May 20, 2004, and 60/599,341, filed Aug. 6, 2004, the disclosures of which are incorporated herein by reference.

GOVERNMENT RIGHTS

This invention was made with United States Government support under Grant Nos. AI 33933, GM37537 and 1 F32 RR018688-01 awarded by the National Institutes of Health as well as MCB-0209793 awarded by NSF. The United States Government has certain rights in the invention.

BACKGROUND

The study and characterization of proteins and peptides has become such a significant part of modern biology that it has its own name: Proteomics. Mass spectrometry has become one of the most important techniques used for the analysis of peptides and proteins, and a number of different mass spectrometry experiments are performed in this field. The present invention relates to the use of mass spectrometry to characterize the sequence of amino acids in peptides and proteins, using either the "bottom up" or the "top down" techniques as have been previously described in the literature. Presently, the most widely used of these types of experiments is the "bottom up" proteomics experiment. However, the present invention described herein will significantly advance the practice of the "top down"-type experiments, as well as any proteomic mass spectrometry experiment which utilizes tandem mass spectrometry (MS/MS).

In the "bottom up"-type experiment, mixtures of proteins, usually derived from some biological sample (such as a cell lysate) and therefore potentially containing as many as several thousand proteins with relative abundances ranging over several orders of magnitude, are analyzed. Such protein samples are digested with a proteolytic enzyme (typically trypsin, or a combination of trypsin and endo-Lys) resulting in a complex mixture of tryptic peptides (the digestion typically yields about 30 peptides/protein). After the digestion step, there generally are various steps of sample cleanup, separation, fractionation and/or chemical derivatization prior to the introduction of the sample to the mass spectrometer. In one embodiment, the processed peptide samples are chromatographically separated and introduced to the mass spectrometer by means of a nanoflow-HPLC (5-200 nL/min) interfaced directly to an electrospray ionization source on one of three different types of mass spectrometers: Finnigan LCQ Deca or LCQ XP (RF 3D quadruole ion traps), Finnigan LTQ (radial ejection RF 2D quadrupole ion trap) or Finnigan LTQ/FT instruments (tandem RF 2D quadrupole ion trap/Fourier transform ion cyclotron resonance mass spectrometer).

The electrospray ionization source converts neutral sample peptides, eluting from the HPLC column, to ions in the gas-phase for analysis by the mass spectrometer. In an aqueous acidic solution, tryptic peptides are protonated on both the amino terminus and the side chain of the C-terminal amino acid (Lys or Arg). As the electrosprayed-peptides enter the mass spectrometer, the water is pumped away and the positively charged amino groups both hydrogen bond and transfer protons to the amide groups along the backbone of the peptide. The result is that the aggregate of each tryptic peptide species eluting from the HPLC is converted into a collection of ionized peptide molecules protonated at different sites along the peptide backbone.

In accordance with one procedure, MS/MS spectra of the ions produced from different peptide species are obtained (mass spectra of fragment ions) in the following sequence of steps.

1. Peptide Ions are introduced and trapped in a RF quadrupole ion trap (2D or 3D)
2. All ions outside of a narrow range of mass-to-charge ratios (m/z) associated with the chosen peptide precursor ion species are eliminated from the trap.
3. The isolated precursor peptide ions are kinetically excited and undergo collisionally activated decomposition (CAD).
4. Retained product ions are mass analyzed to produce a mass (m/z) spectrum.

During step 2, the protonated peptides ions undergo several hundred or thousand collisions with helium atoms, which are present at a pressure of about 1-5 millitorr. During this process the internal energy of the ions is increased by small increments until it exceeds the activation energy required to break the protonated amide bond in the backbone of the molecule (this process is also often referred to as collision induced dissociation, CID). Ideally, the result is a collection of b and y-type fragment ions that differ in mass by a single amino acid. FIG. 1 displays the nomenclature describing the various types of peptide backbone cleavage. Type b ions contain the amino terminus plus one or more amino acid residues. Type y ions contain the carboxyl terminus plus one or more amino acid residues. Subtraction of m/z values for fragments of the same type that differ by a single amino acid yield the mass, and thus the identity of the extra residue in the larger of the two fragments. By continuing this process, it is possible to read the amino acid sequence of the targeted peptide backwards (y ions) and forwards (b ions). A skilled analyst can ascertain all or part of the amino acid sequence of the precursor peptide. There are also computer programs that compare peptide MS/MS spectra to theoretical MS/MS spectra of peptides derived from protein and nucleic acid databases to produce a list of likely precursor peptides (and their structures) for each MS/MS spectrum.

The typical sample is quite complex, so tens or hundreds of different peptides may simultaneously elute from the LC column. To give the instrument time to record MS/MS spectra of a larger percentage of the coeluting peptide precursors a procedure referred to as Peak Parking can be used to extend the chromatography to provide sample peak widths from 10 sec to 200 sec. The use of Peak Parking has been previously described in the literature and is known to those skilled in the art. Generally the experiment is automated and involves the repetition of a sequence mass spectral experiments involving a first full scan MS experiment from which precursor m/z peaks are selected (through automated analysis of the resulting m/z spectrum) for subsequent MS/MS analysis. Depending, upon the instrument speed and the chromatographic peak width (duration of elution of individual species), typically anywhere from 3 to 10 MS/MS spectra are acquired for precursor m/z values determined from the initial MS only experiment. The critera for data dependent selection of precursor m/z values are designed so as to minimize the recording of redundant MS/MS spectra and MS/MS spectra of known background and contaminant peaks. A single such data dependent mode LC MS/MS experiment may vary in duration from 30 minutes to 4 hours and thousands of MS/MS spectra of peptide ions may be recorded. At the end of the chromatographic run, proteins in the original mixture are identified by processing the set of recorded MS/MS spectra of peptide precursors against the various protein and nucleic acid databases. Computer programs for analyzing the data are commercially available and include the SEQUEST (marketed by Thermo Electron) and MASCOT (Matix Science) computer programs. Routinely, six thousand sequences of tryptic peptides can be obtained in a single 4 hr chromatographic run with the above technology. Peptides present at the 5-10 fmol level in complex mixtures (loaded on column) are readily identified.

For the analysis of these complex mixtures of peptides, the greater number of unique MS/MS spectra recorded, the more complete the characterization of the mixture and the greater portion of the peptides from source proteins will be observed (sequence coverage), yielding greater certainty in their identification. Hence, the time it takes to obtain a single MS/MS spectrum is important. A mass spectrometer or method of performing MS/MS that isn't capable of producing a MS/MS spectrum in less than about 2 seconds is considered unsuitable for chromatographic applications such as the "bottom up" type proteomics experiment.

The use of CAD for the production of product ions suffers from several disadvantages include the following:

a) Peptides with post-translational modifications (i.e., phosphorylation and glycosylation, etc) often fragment by loss of the modification rather by cleavage of the peptide backbone. Only a relatively small percentage about (20%-30%) of these types of peptide ion precursors produce interpretable/searchable product ion spectra.

b) Peptides that contain multiple basic amino acid residues (Lys, Arg, and His) and thus carry more than two charges, also fail to fragment randomly along the peptide backbone and thus afford incomplete sequence information when analyzed by the above technology.

c) Peptides that contain more than 40 amino acids also fail to fragment randomly along the peptide backbone. These also afford incomplete sequence information.

Accordingly, there is a need for an improved method of fragmenting peptides to produce a suitable array of interpretable/searchable product ion spectra. An alternate strategy for fragmenting protonated peptides and proteins in the gas phase was suggested by McLafferty, et al., in 1998 (J. Am. Chem. Soc. 1998, 120, 3265-3266). This technique involves interacting the protonated peptides with thermal electrons while both are stored inside an ICR cell of a Fourier transform mass spectrometer. This process is referred to as electron capture dissociation (ECD). The originally proposed mechanism for this dissocation process is as follows:

Reaction of a protonated amine group, $RNH_3^+$, on a multiply charged peptide with a thermal electron is exothermic by about 6 eV and forms a neutral hypervalent nitrogen species, $RNH_3$ (see FIGS. 2A-C). This compound then dissociates to $RNH_2$ and a hydrogen radical, H·, on a time scale that is short compared to energy delocalization via vibrational modes of the molecule. The hydrogen radical attaches to the peptide backbone and triggers cleavage reactions to produce a homologous series of fragment ions of type a, c, y, and z. The c and z type ions are generally more abundant. Again subtraction of m/z values for fragments within a given ion series that differ by a single amino acid affords the mass, and thus the identity of the extra residue in the larger of the two fragments. By continuing this process, it is possible to read the amino acid sequence of the targeted peptide backwards (y and z ions) and forwards (a and c ions). Since this mobile hydrogen radical mechanism was first proposed, alternative mechanisms have been proposed which account for various perceived inadequacies the proposed mechanism such as the capacity of ECD to equivalently fragment multiply sodiated protein and peptide ions (ionized by the addition of $Na^+$ rather that $H^+$).

The advantages of this approach include the following:

1) Peptides with post-translational modifications (phosphorylation or glycosylation) primarily fragment at the peptide backbone bonds and are easily sequenced by mass spectrometry. Fragmentation with loss of the post-translational modification and loss of other side chain moieties is only a minor side reaction or not observed at all.

2) Peptides that contain multiple basic residues (and thus carry more than two positive charges in the gas phase), still fragment more or less randomly along the peptide backbone and are easily sequenced.

3) ECD fragmentation is not limited by the size of the peptide being analyzed. The McLafferty group has now provided extensive evidence that ECD can be employed to confirm the sequences of intact proteins and to locate post-translational modification on the intact molecules.

However, the McLafferty technique does suffer from a number of disadvantages, include the following:

1) It is very difficult to confine positive ions and electrons simultaneously at the near thermal kinetic energies required for the ECD reaction to occur. This has until very recently only been accomplished in an ICR cell located within the high magnetic field of an FT-ICR mass spectrometer. These ECD ICR instruments use a superconducting magnet to generate magnetic fields typically on the order of 4.7 to 9 Tesla and therefore cost 0.5-1.5 million dollars each. Most protein sequence analyses are presently conducted on RF quadrupole ion trap, RF quadrupole linear trap, Q-TOF (quadrupole-time-of-flight), or TOF-TOF instruments. The primary difficultly with implementing ECD on any mass spectrometer other than an FTICR, is that the inhomogeneous RF field devices (RF traps and ion guides) conventionally used to contain ions during CAD will not confine electrons. This is because the mass of the electron is so small. Electrons injected into these devices also fail to remain at near thermal energies for a time interval that is sufficient to allow ECD reactions to occur with any efficiency. Accordingly, although some groups have recently reported performing ECD in RF ion traps, the sensitivity/fragment ion yield of these experiments is substantially lower than results obtained with conventional ECD.

2. ECD in the Fourier transform instruments is not very efficient. The best data we are aware of from the most advanced instruments indicates that the total (integrated) product ion signal is about 20% of that of the precursor (a precursor to product conversion efficiency of 20%). For comparison, commercial ion trap instruments, that utilize CAD, routinely produce precursor to product conversion efficiencies in the range of 50-100% depending on the precursor ion. Peptide ions generally have precursor to product conversion efficiencies on the higher end of this range. Instruments, such as the Q-TOF, that use RF-multipole, collision cell have somewhat lower precursor to product conversion efficiencies, but these are still generally in the range of 30-90%.

3. Most published ECD spectra are the averages (or sums) of several tens of recorded mass spectra. Typically a single FT/ICR spectrum takes on the order of a second to generate. This means that an ECD product-ion spectrum, having a reasonable signal to noise ratio, typically takes several tens of seconds to record. It probably takes at least 30 ions to create detectable ion signal. In contrast, RF quadrupole ion trap and Q-TOF type instruments, using electron multiplier-based detectors, readily detect single ions.

4. A further disadvantage of ECD is that when the precursor ions are large peptide or protein ions, the product ions of a given precursor often remain bound together, presumably by non-covalent bonds (hydrogen bonding) and fail to dissociate under ECD experimental conditions. A second activation (e.g., photo or collisional-activation) dissociation step is required to break these hydrogen bonds and to allow observation of ECD product ions (c and z-type product ions).

The present invention provides a new method of fragmenting positively charged peptides in an RF field mass spectrometer or an RF field ion containment device and for performing sequence analysis of peptides and proteins by mass spectrometry. The invention involves the use of a gas-phase anion to transfer an electron to a positively charged sample ion resulting in fragmentation of the positively charged sample ion.

SUMMARY OF VARIOUS EMBODIMENTS

The present disclosure is directed to a new method for fragmenting ions in a mass spectrometer and for performing sequence analysis of peptides and proteins by mass spectrometry. In accordance with one embodiment polypeptide ions are fragmented randomly along the peptide backbone by an electron transfer dissociation event, wherein a target polypeptide is ionized, and injected into a quadrupole linear ion trap. Singly or multiply charged gas-phase ions, having the opposite charge as the ionized polypeptide, are then introduced into a quadrupole linear ion trap and the gas-phase reagent ions and the ionized polypeptides are allowed to mix under controlled conditions so as to facilitate electron transfer from the anion to the cation, and thus induce the production of electron transfer dissociation polypeptide product ions.

In accordance with one embodiment a method for dissociating multiply charged cations is provided. The method comprises the steps of introducing multiply charged cations into an RF electric field ion containment device, introducing gas-phase electron transfer reagent anions into said ion containment device, and then mixing the introduced reagent anions, or derivative reagent ions thereof, and the multiply charge cations, or derivative multiply charged cations thereof, so as to facilitate electron transfer from the reagent anions, or derivative reagent ions thereof, to the multiply charge cations, or derivative multiply charged cations thereof, to produce dissociation product cations. This process is herein referred to as electron transfer dissociation (ETD). In this embodiment the mixing of the ions comprises superimposing the two ion clouds so that electron transfer takes place.

In accordance with one embodiment, ion-ion reactions involving the transfer (abstraction) of electrons from multiply charged polypeptide ions are used to effect negative electron transfer dissociation (NETD) of the polypeptide analyte ions within an RF electric field ion containment device. In the ETD process, the multiply charged polypeptide analyte ions are cations (positive ions). In the NETD process, the multiply charge polypeptide analyte ions are anions (negative ions). The term negative electron transfer dissociation (NETD) is used to distinguish this process from ETD. ETD and NETD represent two separate and distinct types of dissociation promoting ion-ion reactions, as is suggested by both opposing polarity of analyte ions involved as well as the opposing directions of the electron transfer relative to the analyte.

In accordance with one embodiment the ionized polypeptide is a multiply deprotonated peptide and the radical gas-phase ion is a cation selected from the group consisting of any inert gas cation (e.g., $He^+$, $Ne^+$, $Xe^+$, $Ar^+$, $N_2^+$, $O_2^+$, $CO^+$) or any other radical cation. The transfer of an electron is sufficiently exothermic to cause fragmentation of the sample molecule. In an alternative embodiment a gas-phase anion is used to transfer an electron to a positively charge sample ion. This process is sufficiently exothermic to cause fragmentation of the sample molecule. In accordance with one embodiment the radical gas-phase anions are singly or multiply charged and are injected along the linear axis of a 2D-multipole trap, and the polypeptide cation precursors are injected along the linear axis of a 2D-multipole trap from the opposite direction as the gas-phase anions.

In the case of peptides, the invention promotes fragmentation along the peptide backbone and makes it possible to deduce the amino acid sequence of the sample. In accordance with one embodiment a method for analyzing the amino acid sequence of a polypeptide is provided. The method comprises the steps of injecting a multi-charged polypeptide into a quadrupole linear ion trap, and spatially isolating the multi-charged polypeptide in a first defined region of the ion trap, injecting singly or multiply charged gas-phase anions into a quadrupole linear ion trap and spatially isolating the anions in a second defined region of the ion trap, mixing the gas-phase anions and the multi-charged polypeptide so as to facilitate electron transfer from the radical anions to the multi-charged polypeptide, thus inducing the production of electron transfer dissociation product ions, terminating the reactions by separating the remaining radical gas-phase anions from the electron transfer dissociation product ions and sequentially resonantly ejecting the electron transfer dissociation product ions though slots in the rod electrodes to an ion detector to conduct mass analysis of the ions and determination of the amino acid sequence of the polypeptide.

BRIEF DESCRIPTION OF THE DRAWINGS

FIGS. 5A-5H are schematic representations of the linear ion trap operation to accomplish positive and negative injection, simultaneous +/−storage, and ion/ion reaction. Initially cations are injected from the front of the device, as in normal operation, and accumulated in the center section of the linear trap (FIG. 5A). Next, a chosen precursor ion species is selected and isolated by radial ejection of all other positive ions outside of the selected m/z window (FIG. 5B). Afterwards, the ions of the selected precursor type are moved to the front section of the linear ion trap by adjusting the DC offset of front section (FIG. 5C). FIGS. 5D and 5E displays the procedure for injecting anions, from the rear source, by raising the DC offsets on both the center and back sections of the linear ion trap. In this way, positive ions are contained in the front section, while negative ions are injected through the back section and accumulate in the center. FIG. 5E m/z selecting (m/z isolating) the anions before the anions and the cations are allowed to mix and react. Finally, by imposition an axially confining of a pseudo-potential, created by 150 Vp, 600 kHz RF, applied to the lenses, the cations and anions are allowed to mix and react in a compined trapping region(FIG. 5F). The the reaction period is terminated by lowering the DC offset of the center section and removing the pseudo-potential, to cause axial release of the anions while still providing axial containment of the remaining precursor and product cations. These cations are then m/z analysed by, ramping the main RF (FIG. 5G) and m/z seqentially radially ejecting the ions (vias resonant excitation) to a detector. Alternatively, the remaining reagent anions can be retained and m/z analyzed by simply reversing the DC offset, (FIG. 5H).

FIG. 7A shows the total ion chromatogram (peaks are ≈10 sec wide). FIG. 7B represents data from a single-scan, 500- to 600-msec, ETD spectrum recorded on 100 fmol of the triply protonated peptide, DRVYIHPFHL (SEQ ID NO: 2). FIG. 7C represents data from a single-scan, 500- to 600-msec, ETD spectrum recorded on 1 fmol of the triply protonated peptide, DRpSPIRGpSPR.

FIG. 8A shows a CAD spectrum dominated by fragment ions corresponding to the loss of phosphoric acid and either methanol or water moieties. FIG. 8B demonstrates an ETD spectrum containing 13 of 14 possible c- and z-type product ions. Note that the spectrum is devoid of fragment ions corresponding to the loss of phosphoric acid.

FIG. 12A is a CAD MS/MS spectrum of a quadruply charged human nuclear phosphopeptide containing strong neutral losses of phosphoric acid. FIG. 12B is the corresponding ETD spectrum of the same phosphopeptide showing a near complete series of c and z fragment type ions. Note the CAD and ETD spectra were acquired back-to-back during single analysis (scans 2681 and 2682). Note, —OCH3 indicates C-terminal conversion to a methyl ester.

As seen in FIG. 16A, the rest of the ions in the spectrum are not detectable. When GRLGsSRAGR (SEQ ID NO: 70) was fragmented by ETD, a complete c and z ions series was observed with no observable loss of $SO_3$ from the parent ion (FIG. 16B).

FIGS. 18A-18E represents a tandem mass spectra resulting from analyzing the doubly protonated peptide, RPKPQFFGLM (SEQ ID NO: 71) by CAD and ETD dissociation. FIG.

18A represents the spectrum resulting from a 100 ms reaction of the radical anion of fluoranthene. FIG. 18B represents the spectrum resulting from a 100 ms reaction of the radical anion of fluoranthene followed by CAD conducted at q=0.25, normalized activation energy of 35%. FIG. 18C represents the spectrum resulting from a CAD conducted at q=0.25, normalized activation energy of 35%. FIG. 18D represents the spectrum resulting from a 100 ms reaction of the radical anion of fluoranthene followed by CAD conducted at q=0.13, normalized activation energy of 17%. FIG. 18E represents the spectrum resulting from a CAD conducted at q=0.13, normalized activation energy of 17%.

DETAILED DESCRIPTION

Definitions

Figure 1:
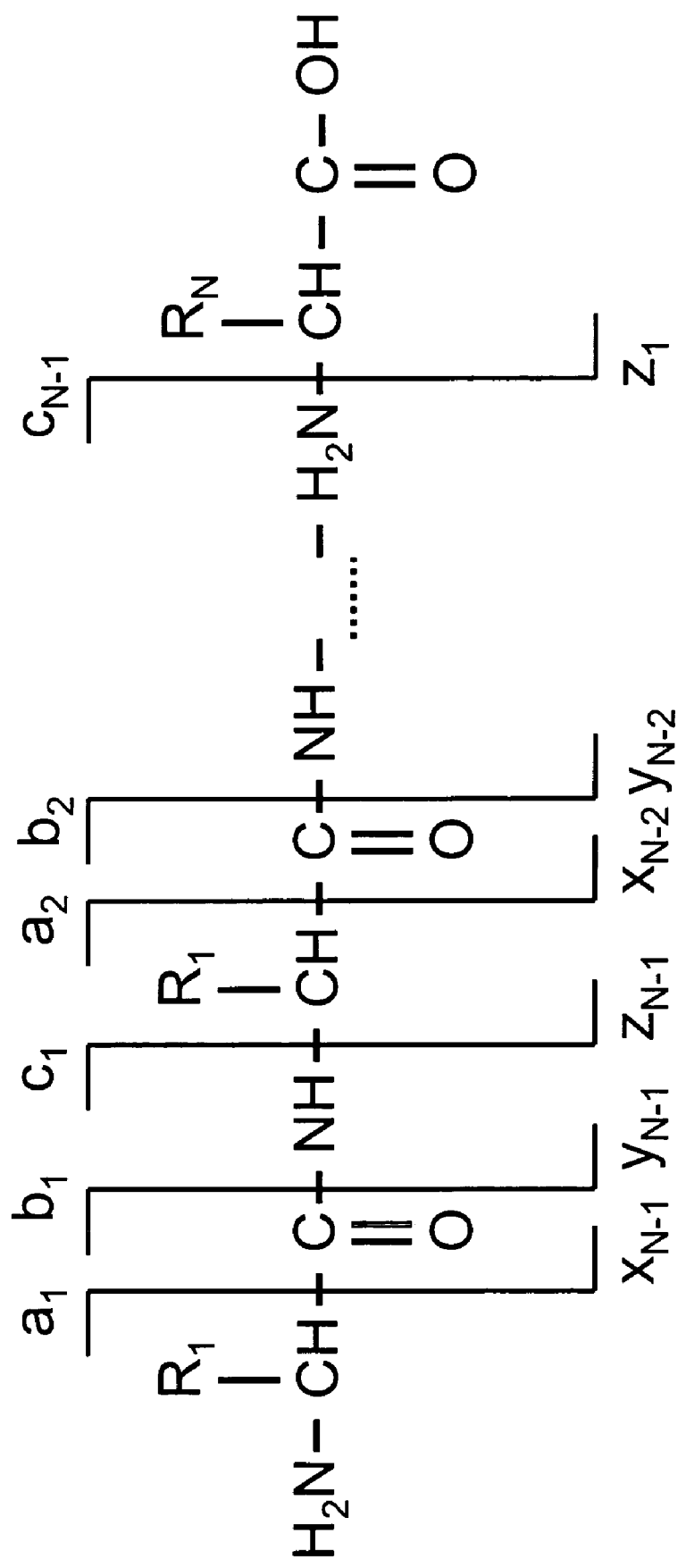
FIG. 1 is a schematic representation of the various types of peptide backbone cleavage produced by mass spectrometry peptide analysis and the associated nomenclature for the cleaved products. Note a, b, c-type fragment ions contain the amino-terminus, while x, y, z-type fragment ions contain the c-terminus of the precursor peptide ion. The low energy CAD process predominantly cleaves the amide linkage to form b/y-type pairs; ECD and ETD cleave the amine bond to form mostly c/z-type fragment ions.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

As used herein the term "aryl" refers to a mono- or multi-cyclic carbocyclic ring system having one or more aromatic rings including, but not limited to, phenyl, benzyl, naphthyl, tetrahydronaphthyl, indanyl, indenyl, anthracenyl and the like. "Optionally substituted aryl" includes aryl compounds having from zero to four substituents, and "substituted aryl" includes aryl compounds having one to three substituents, wherein the substituents include hydroxyl, $C_1$-$C_4$ alkyl, halo or amino substituents.

The term "polyaromatic hydrocarbon" refers to a multi-cyclic carbocyclic ring system comprising two or more aromatic rings (selected from aryl and heteroaryl ring structures), and including but not limited to napthalene, fluorene, phenanthrene, pyrene, fluoranthene, chrysene, triphenylene, perylene, acridine; 2,2' dipyridyl; 2,2' biquinoline; 9-anthracenecarbonitrile; dibenzothiophene; 1,10'-phenanthroline; 9' anthracenecarbonitrile; and anthraquinone. "Substituted polyaromatic hydrocarbon" includes polyaromatic hydrocarbon compounds having one to three substituents, wherein the substituents include aryl, heteraryl, hydroxy, $C_1$-$C_4$ alkyl, halo, —CN, or amino substituents.

The term "heterocyclic group" refers to a mono- or multi-cyclic carbocyclic ring system containing one or more heteroatoms wherein the heteroatoms are selected from the group consisting of oxygen, sulfur, and nitrogen.

As used herein the term "heteroaryl" refers to a mono- or multi-cyclic carbocyclic ring system having one or more aromatic rings containing one or more heteroatoms (such as O, N and S) and includes, but is not limited to, furyl, thienyl, pyridyl and the like.

As used herein the term "macromolecule" refers to polymers of monomeric units or derivatives thereof, including synthetically derived polymers as well as naturally occurring polymers. Examples of macromolecules include polypeptides, polysaccharides, and nucleic acids.

The terms "polypeptide", "peptides", "oligopeptide" and "protein" refer to a polymer of amino acids without regard to the length of the polymer; thus, the terms are used interchangeably. This term also does not specify or exclude chemical or post-expression modifications of the polypeptides of the invention, although chemical or post-expression modifications of these polypeptides may be included or excluded as specific embodiments. Modifications to polypeptides include the covalent attachment of glycosyl groups, acetyl groups, phosphate groups, lipid groups, ubiquitin groups, sulfur groups and the like are expressly encompassed by the term polypeptide. Further, polypeptides with these modifications may be specified as individual species to be included or excluded from the present invention. The modifications of the polypeptides can occur anywhere in a polypeptide, including the peptide backbone, the amino acid side-chains and the amino or carboxyl termini. It will be appreciated that the same type of modification may be present in the same or varying degrees at several sites in a given polypeptide. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).).

Embodiments

The present disclosure is directed to the use of ion-ion reactions to effect the dissociation of polypeptide ions in a mass spectrometer system. More particularly, one aspect of the present disclosure is directed to utilizing ion-ion reactions involving the transfer of electrons to mutilply charged polypeptide analyte ions within an RF electrical field ion containment device and thereby promote electron transfer dissociation (ETD) of the polypeptide ions.

In accordance with another embodiment, ion-ion reactions involving the transfer (abstraction) of electrons from multiply charged polypeptide ions are used to effect negative electron transfer dissociation (NETD) of the polypeptide analyte ions within an RF electric field ion containment device. In the ETD process, the multiply charged polypeptide analyte ions are cations (positive ions). In the NETD process, the multiply charge polypeptide analyte ions are anions (negative ions). The term negative electron transfer dissociation (NETD) is used to distinguish from ETD. ETD and NETD represent two separate and distinct types of dissociation promoting ion-ion reactions, as is suggested by both opposing polarity of analyte ions involved as well as the opposing directions of the electron transfer relative to the analyte. As will be explained and shown below these different processes lead to the dissociation of different chemical bonds along the backbone the analyte polypeptide ions.

In accordance with one embodiment multiply charged polypeptide anions are introduced into a quadrupole linear ion trap, and confined in a first defined region of the ion trap. Singly or multiply charged radical gas-phase cations, having a charge opposite of the polypeptide ion are then introduced into a quadrupole linear ion trap along the linear axis of the quadrupole linear ion trap. The two ion species, or ions derived from the originally introduced species, are then mixed within the linear ion trap so as to facilitate electron transfer from the anions to the cations, thus inducing the production of negative electron transfer dissociation (NETD) product anions. In accordance with one embodiment the polypeptide is multiply deprotonated and the gas phase ion is a cation. In one embodiment the cation is any inert gas cation (e.g., He, Ne, Xe, Ar, $N_2^+$, $O_2^+$, $CO^+$) or any other radical cation, that will abstract an electon from an polypepdide anion.

In accordance with one embodiment a method for dissociating multiply charged cations is provided. The cations may be selected from a broad range of material including macromolecules, such as nucleic acids, polysaccharides and polypeptides as well as other compounds including pharmaceutical agents and complex mixtures of organic compounds. The method comprises the steps of introducing multiply charged cations into an RF electric field ion containment device, introducing gas-phase electron transfer reagent anions into said ion containment device, and mixing the introduced reagent anions so as to facilitate electron transfer from the reagent anions, or derivative reagent ions thereof, to the multiply charge cations. It is considered within the scope of the present invention that the respective cations and/or anion can be directly injected into the RF electric field ion containment device and allowed to mix and react, or alternatively the injected cations and/or anions can be subjected to further manipulations after injection and prior to being mixed together.

In accordance with one embodiment, after the cations are injected into the RF electric field ion containment device, the cations are subjected to one or more of the following manipulations. The this initial cation population may be subjected to m/z isolation, proton transfer charge reduction (including ion parking), photo-dissociation, collisional activation and ion-molecule reactions to produce derivative multiply charged cations of the original injected cation population. Similarly, the originally injected anions can be subjected to various manipulations before the anion is mixed with the cation (or cation derivatives). In particular, the anion population may be subjected to one or more of the following manipulations: m/z isolation, photo-dissociation, collisional activation and ion-molecule reactions to produce derivative singly or multiply charged anions of the original injected anion population.

Accordingly, in one embodiment multiply charged cations are injected into an RF electric field ion containment device, gas-phase electron transfer reagent anions are introduced into the ion containment device, the injected anions and cation are then optionally further manipulated and then the introduced reagent anions, or derivative reagent ions thereof, are mixed with the multiply charge cations, or derivative multiply charged cations thereof, so as to facilitate electron transfer from the reagent anions, or derivative reagent ions thereof, to the multiply charge cations, or derivative multiply charged cations thereof, to produce dissociation product cations.

In accordance with one embodiment the introduced multiply charged cation is a polypeptide. In accordance with one embodiment the kinetic energies of the introduced reagent anions, or derivative reagent ions thereof, and the multiply charge polypeptides, or derivative multiply charged polypetides thereof, are less than electron volt. In accordance with one embodiment collisions with background gas molecules in are used to reduce the kinetic energies of the anions and the multiply charged cations to near thermal levels during the mixing and reaction step.

In accordance with one embodiment the RF electric field ion containment device is an RF ion guide. In another embodiment the RF electric field ion containment device is an RF ion trap. One such device suitable for use in the present invention is a RF linear multipole ion trap, and in one embodiment the RF ion trap is a RF 3 dimensional multipole ion trap. In one embodiment the anions are injected along the linear axis of a RF linear multipole ion trap.

In accordance with one embodiment a method for fragmenting a positively multi-charged polypeptide is provided. The method comprising the steps of introducing positively multi-charged polypeptides into an ion trap, introducing gas-phase anions into an ion trap, and mixing the gas-phase anions and the positively multi-charged polypeptide so as to facilitate electron transfer from the anions to the positively multi-charged polypeptide, thus inducing fragmentation of the positively multi-charged polypeptide to produce electron transfer dissociation product ions. As used herein the term introducing ions into the ion trap is intended to encompass not only those ions that are directly injected into the ion trap, but also derivative ions that are produced from the originally injected ions after they are injected into the ion trap. The ion trap may be selected from any of the ion containment devices known to those skilled in the art. Suitable devices include Fourier transform ion cyclotron resonance (FTICR) mass spectrometers, RF 3D multipole ion traps (QIT) and RF linear 2D multipole ion traps. In one embodiment the device is selected based on its capability of separately storing anions/cations and subsequently combining them. In one embodiment the ion trap is an RF ion trap, and more particularly, in one embodiment the RF ion trap is a segmented linear RF multipole ion trap.

During or after the mixing of the multiply charged polypeptide and the anion, the electron transfer dissociation product ions can be subjected to additional activation energy. More particularly, the electron transfer dissociation product ions are supplied with sufficient energy to trigger an electron transfer-type dissociation pathway, without production of substantial conventional collision-activated dissociation products. In accordance with one embodiment the procedure produces less than 20% CAD products, in a further embodiment less than about 10% CAD products are produce and in a further embodiment less than about 5% CAD products are produced and in a further embodiment less than about 1% CAD products are produced. The energy can be supplied in the form of photoactivation or collisional activation. In one embodiment the electron transfer dissociation product ions are subjected to low-energy, off-resonance collisional activation wherein less than 20% of the products produced are conventional collision-activated dissociation products. In accordance with one embodiment the electron transfer dissociation product ions are further activated, after the multiply charged polypeptide have been mixed with the anions, using reduced Finnigan LTQ CAD conditions, having a $q=0.15$ or less, and a normalized activation energy 20% or less, for 60 ms duration). In one embodiment the reduced activation conditions comprise a q value of 0.13 or less, and a normalized activation energy of 17%, for 60 ms duration.

In accordance with one embodiment after the multiply charged polypeptide is mixed with the anion and electron transfer dissociation product ions are formed, the remaining anions from the linear ion trap are ejected, while the electron transfer dissociation product ions are retained within the linear ion trap. The remaining electron transfer dissociation product ions are then subjected to low-energy, off-resonance collisional activation such that the activation generates less than about 20% or less than about 5% of total ion products that are derived from conventional collision-activated dissociation pathways (for peptides this would typically be b or y-type ions and/or neutral losses thereof).

The electron transfer dissociation product ions produced by the present method can be subjected to mass (m/z) analysis. In accordance with one embodiment a method for analyzing the amino acid sequence of a polypeptide is provided. The method comprises the steps of introducing multiply charged polypeptide cations into an RF ion trap, introducing gas-phase anions into an RF ion trap, mixing gas-phase anions and multiply charged polypeptide cations so as to facilitate electron transfer from the anions to the multiply charged polypeptide cations, thus inducing the production of electron transfer dissociation product ions, terminating the reactions by physically separating the remaining gas-phase anions from the electron transfer product cations and conducting m/z analysis of cations remaining in the trap. The remaining cations may include the electron transfer product cations, or derivative cations of those electron transfer product cations. In accordance with the present disclosure the term "mixing" is intended to encompass the process of allowing the two ion clouds to superimpose so that ETD occurs.

Prior to the step of mass (m/z) analyzing and detecting said electron transfer dissociation product ions, in one embodiment the first type of anions are expelled from the ion trap and then anions of a second type are introduced into the linear ion trap, wherein the second type anions will substantially exclusively abstract protons from cations (PTR), and the second type of anions are mixed and reacted with the cations. In accordance with on embodiment the second anion type is derived from a carboxylic acid, phenolic, and alkoxide containing compound. In one embodiment the second anion is an anion of a compound selected from the group consisting of benzoic acid, perfluoro-1,3-dimethylcyclohexane, (PDCH), $SF_6$, and perfluorotributylamine (PFTBA).

In accordance with one embodiment a positively multi-charged polypeptide is injected into a quadrupole linear ion trap, and is isolated in a first defined region of the ion trap. Singly or multiply charged gas-phase anions are then injected into a quadrupole linear ion trap and isolated in a second defined region of the ion trap. In accordance with one embodiment the anion is a radical gas-phase anion and the polypeptide is a multi-protonated polypeptide. The gas-phase anions and the multi-charged polypeptide are then mixed so as to facilitate electron transfer from the radical anions to the multi-protonated polypeptide, thus inducing the production of electron transfer dissociation product ions.

Electron transfer dissociation (ETD) causes random fragmentation of the polypeptide along the peptide backbone to allow sequence analysis of the polypeptide by mass spectrometry. Electron transfer dissociation (ETD) combines the strengths of two existing methods, collision induced dissociation or (CID) and electron capture dissociation (ECD). ECD is presently restricted (for analytical purposes) to expensive Fourier transform instruments that employ a Penning trap in a super conducting magnet as the mass analyzer. In contrast, ETD, like CID, can be adapted to various RF quadrupole ion trap mass spectrometers, as well as to Q-TOF-type instruments and to other hybrid-type instruments that utilize (or can be adapted to utilize) RF multipole linear traps for accumulation of ions ahead of the last mass analyzer. ETD produces the same type of fragment ions as ECD and thus is ideally suited for characterization of peptides containing multiple basic amino acids and post-translational modifications. As shown herein the ETD technique produces a high quality spectra (precursor to product conversion efficiency of about 5-20%) that is generated on the chromatographic time scale (about 200-500 ms/spectrum).

Figure 2:
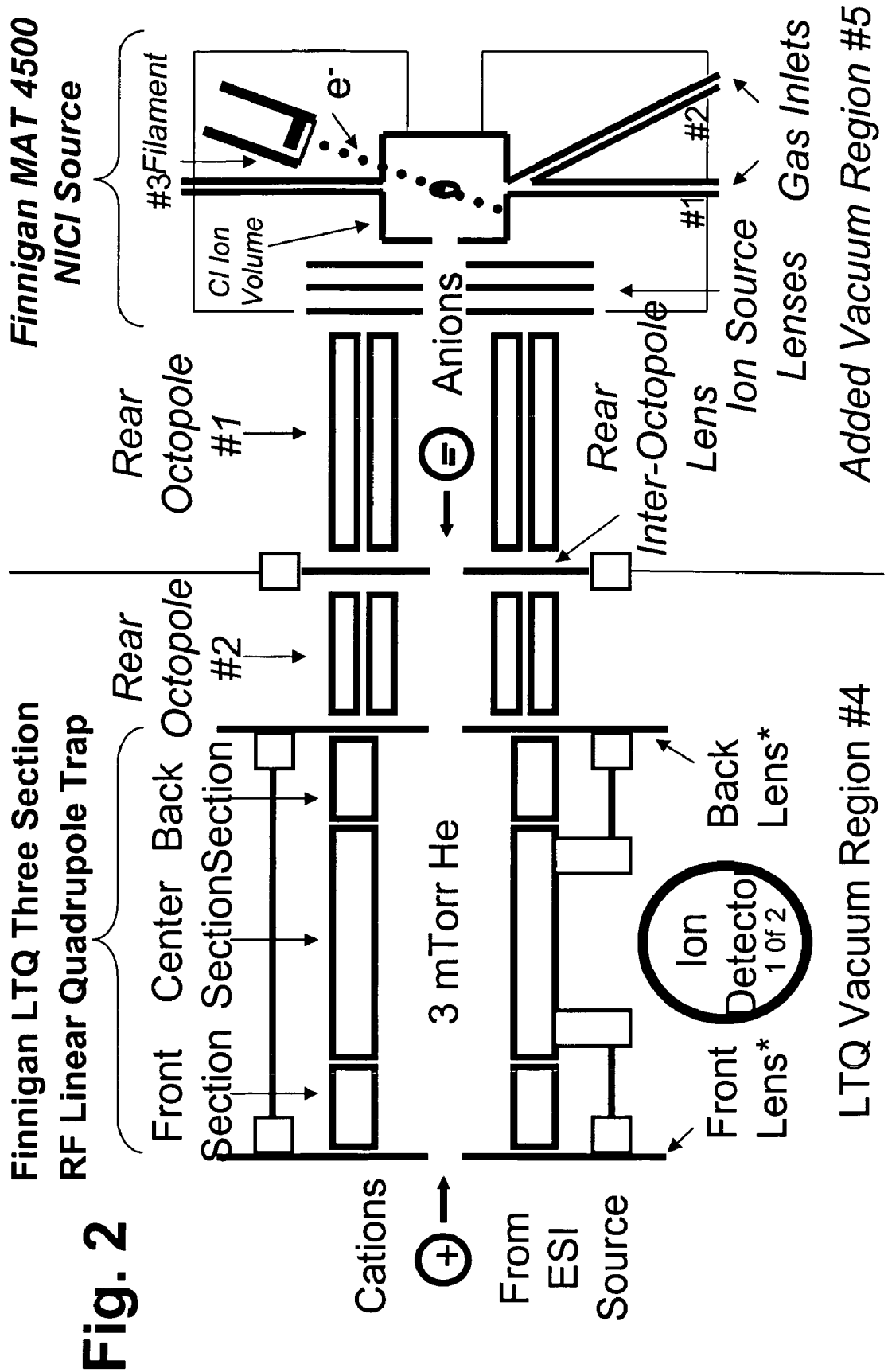
FIG. 2 is a schematic representation showing the instrumental setup and components added to the Finnigan LTQ for the ETD experiments described herein. Items listed in italics are added components, the astericks on the front and back lens indicate where the secondary RF voltage is applied. The NICI (Negative Ion Chemical Ionization) ion source (shown on the right) is interfaced with the linear ion trap by the addition of two octopoles and an inter-octopole lens. These added features serve to produce and transport anions (or cations, if desired) into the linear ion trap.

In accordance with one embodiment, a gas-phase anion is used to transfer an electron to a positively charged sample ion within an RF multipole linear ion trap of a mass spectrometer (FIG. 2 displays an instrument overview). This process is sufficiently exothermic to cause fragmentation of the sample molecule. In the case of peptides, the invention promotes fragmentation along the peptide backbone and makes it possible to deduce the amino acid sequence of the sample. Using this method, anions are generated in a chemical ionization (CI) source using methane, for example, as the reagent gas (see FIGS. 3 and 4). Electron bombardment of methane at 1 torr pressure with 70 eV electrons generates $CH_4^{+\cdot}$, $CH_3^+$ and a population of near thermal electrons.

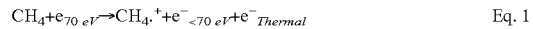

$$CH_4 + e^-_{70\,eV} \rightarrow CH_4^{+\cdot} + e^-_{<70\,eV} + e^-_{Thermal} \qquad \text{Eq. 1}$$

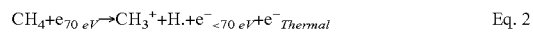

$$CH_4 + e^-_{70\,eV} \rightarrow CH_3^+ + H\cdot + e^-_{<70\,eV} + e^-_{Thermal} \qquad \text{Eq. 2}$$

To produce anions for the ETD reaction, molecules are vaporized into the chemical ionization source and allowed to react with a population of thermal electrons. This is well-known technology that has been previously described (Hunt et al., Anal. Chem. 1976, 48, 2098 and Hunt et al., Anal. Chem. 1978, 50, 1781-1784). Any molecule that possesses a positive electron affinity (EA) (reacts exothermically to form a stable or transiently stable radical anion) can function as an electron donor and thus has the potential to be used a reagent in the electron transfer dissociation reaction. However, it should be noted that non-radical (even electron) anions can also serve as electron donors. Examples of potential reagent anions are as follows:

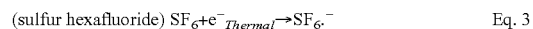

$$\text{(sulfur hexafluoride)}\ SF_6 + e^-_{Thermal} \rightarrow SF_6^{-\cdot} \qquad \text{Eq. 3}$$

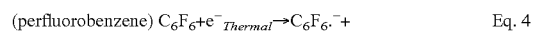

$$\text{(perfluorobenzene)}\ C_6F_6 + e^-_{Thermal} \rightarrow C_6F_6^{-\cdot} \qquad \text{Eq. 4}$$

$$\text{(perfluorobenzene)}\ C_6F_6 + e^-_{Thermal} \rightarrow C_6F_5^- + F\cdot \qquad \text{Eq. 5}$$

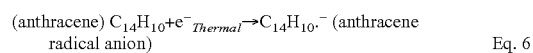

$$\text{(anthracene)}\ C_{14}H_{10} + e^-_{Thermal} \rightarrow C_{14}H_{10}^{-\cdot}\ \text{(anthracene radical anion)} \qquad \text{Eq. 6}$$

Equations for the non-radical anthracene ions are as follows:

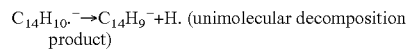

$$C_{14}H_{10}^{-\cdot} \rightarrow C_{14}H_9^- + H\cdot\ \text{(unimolecular decomposition product)}$$

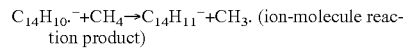

$$C_{14}H_{10}^{-\cdot} + CH_4 \rightarrow C_{14}H_{11}^- + CH_3\cdot\ \text{(ion-molecule reaction product)}$$

In accordance with one embodiment of the invention, a method is provided for randomly dissociating positively charged ions in a mass spectrometer. In one embodiment the method comprises the steps of transferring an electron from a gas phase anion to a positively charged ion in an RF field instrument. In one embodiment the anion is a singly charged anion and in another embodiment the RF field instrument is a segmented-2D-multipole trap, and in one embodiment the instrument is a segmented-2D quadrupole trap. In one embodiment the stable or transiently stable anions are injected along the linear axis of a segmented-2D-multipole trap to prevent collision activated detachment of an electron from the reagent anion. In a further embodiment the positively charged ions are injected along the linear axis of a 2D-multipole trap into the opposite end of the segmented-2D-multipole trap from where the anions were injected.

Figure 5A:
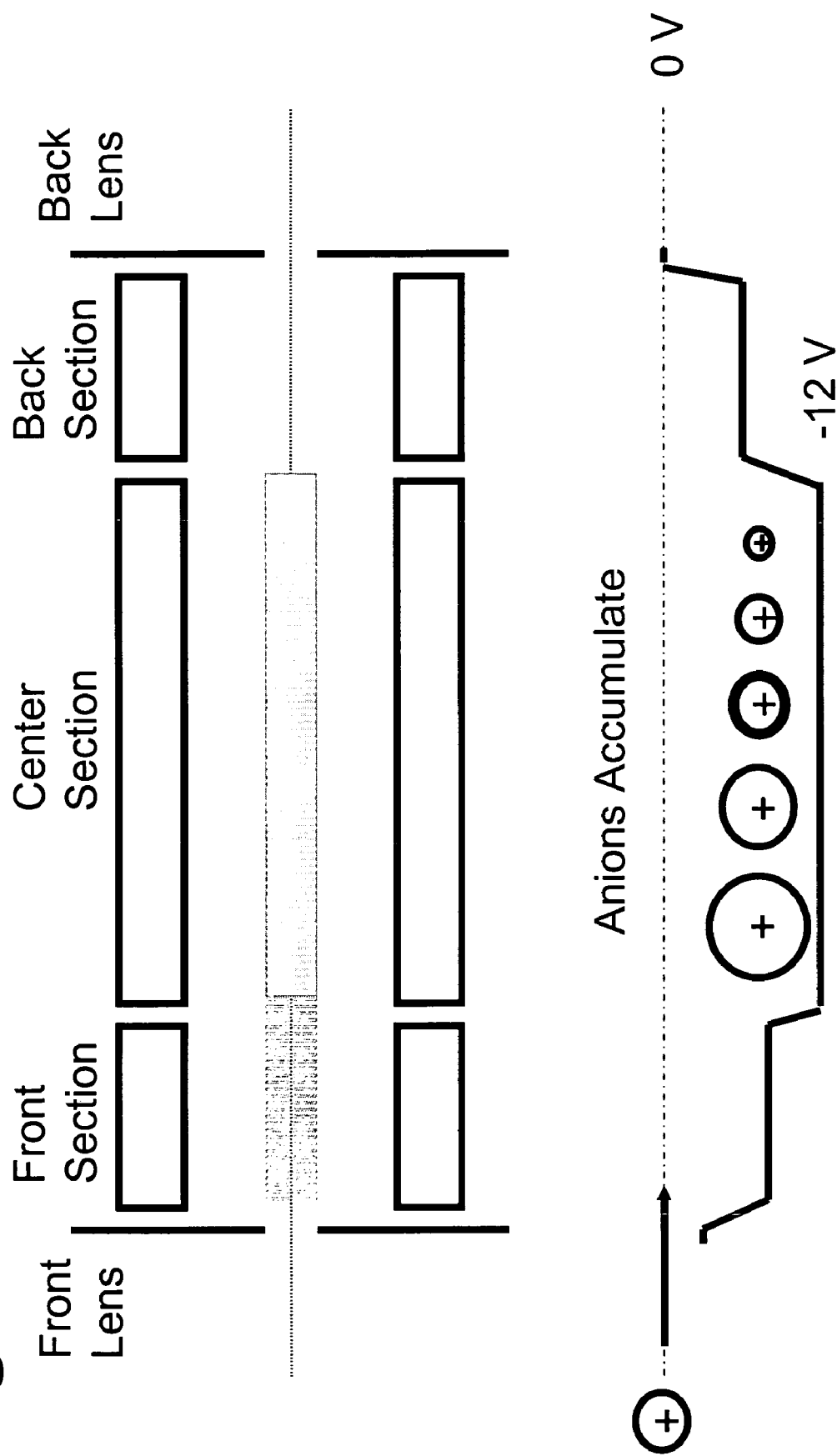
Figure 5E:
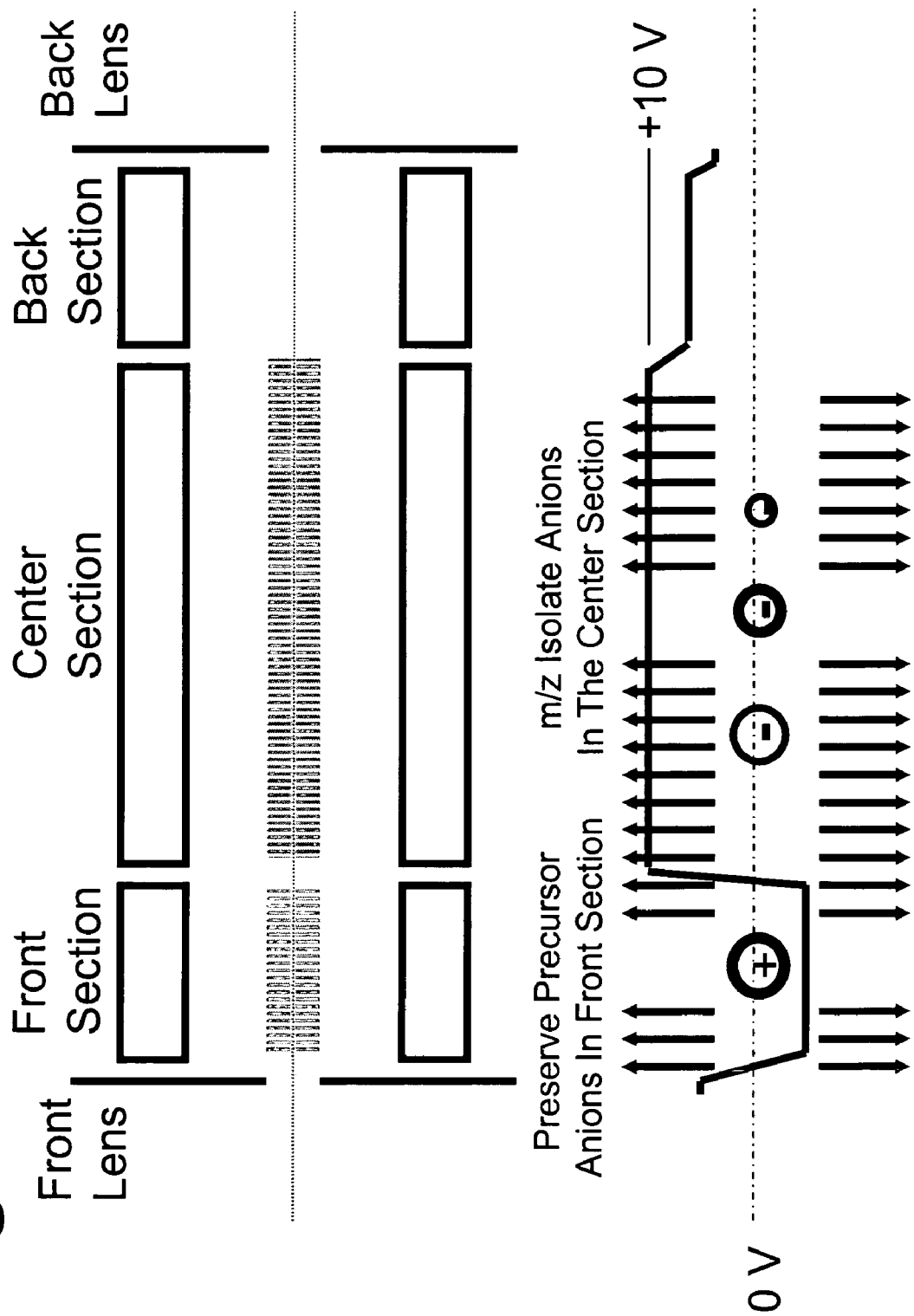
Figure 5F:
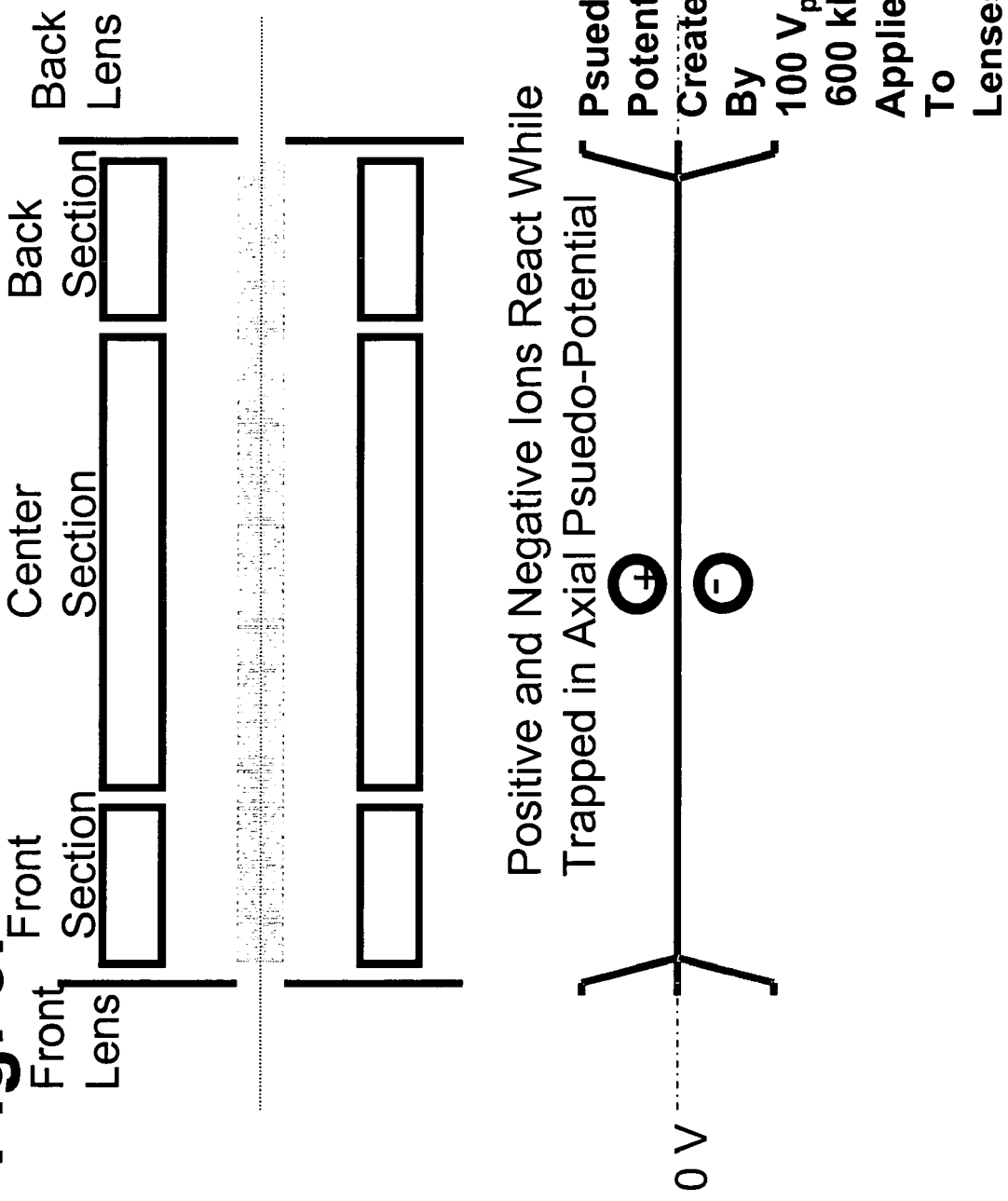

In accordance with one embodiment the ETD experiment is conducted by injecting protonated peptides, generated by electrospray ionization, along the linear axis from one end of a segmented 2D-multipole ion trap and storing them in the front segment (FIGS. 5A-5C). Negative ions are then injected along the linear axis of the same segmented-2D-multipole trap, but from the opposite end (FIG. 5D). Negative ions are stored in the center segment of the linear ion trap (FIGS. 5D and 5E) and then allowed to mix with the positive ions (FIG. 5F). After the defined reaction period the anions are axially ejected, while the cation products are mass analyzed (FIGS. 5G and 5H).

In accordance with one embodiment ETD can be used for the direct sequence analysis of proteins through the use of sequential ion/ion reactions coupled with online chromatography. In this embodiment multiply charged polypeptides are first isolated and reacted with a singly or multiply charged anion within a linear ion trap spectrometer. In one embodiment the anion is a radical anion, and in another embodiment the anion is a singly charged radical anion. After a relatively short reaction (about 5 to about 20 ms) the remaining anions are expelled from the ion trap and the polypeptide ion products are reacted with a second anion species injected into the ion trap. The second anion species injected into the trap is selected based on its ability to transfer protons. The transfer of a proton to the polypeptide ion products serves to simplify the product spectrum to contain only singly protonated fragment ions and to produce a homologous series of singly charged c and z type fragment ions characteristic of the the N and C terminal sequence of the precursor protein. In one embodiment the second anion injected into the ion trap is even electron anions of benzoic acid and the reaction is conducted for about 75 to about 150 ms.

Various reactions may occur when a multiply charged (protonated) peptide, $(M+nH)^{+n}$, either encounters an odd-electron anion, $A^{\cdot -}$, or an even electron anion, $A^-$. Here the number, n, is an integer that defines the initial number of charges on the precursor ion (it is assumed to be 2 or greater). Primarily reactions have been observed by applicants that involve either electron transfer (Eqs 7 and 9) or proton transfer (Eqs 8 and 10) as outlined below. Electron transfer reactions (Eqs 7 and 9) produce hydrogen radicals that initiate the peptide backbone fragmentation observed under ECD conditions. Proton transfer reactions (Eqs 8 and 10) reduce the charge on the peptide, but fail to promote fragmentation. Energy released in the proton transfer reaction remains in the product that contains the newly formed covalent bond and is, therefore, concentrated in either AH or AH., not the protonated peptide.

$$[M+nH]^{+n} + A^{\cdot -} \rightarrow \quad\text{Eq. 7}$$
$$[M+nH]^{\bullet(n-1)+} + A \rightarrow [M+(n-1)H]^{(n+1)+} + H^\bullet + A$$

$$[M+nH]^{+n} + A^{\cdot -} \rightarrow [M+(n-1)H]^{(n-1)+} + [AH]^\bullet \quad\text{Eq. 8}$$

$$[M+nH]^{+n} + A^- \rightarrow \quad\text{Eq. 9}$$
$$[M+(nH)]^{\bullet(n-1)+} + [A]^\bullet \rightarrow [M+(n-1)H]^{(n+1)+} + H^\bullet + A^\bullet$$

$$[M+nH]^{+n} + A^- \rightarrow [M+(n-1)H]^{(n-1)+} + [AH] \quad\text{Eq. 10}$$

Associative reactions have also been observed where the cations and anions form bound complexes which may subsequently dissociate to produce various product ions.

Electron transfer involves the abstraction of an electron from the reagent anion by the precursor cation. This is followed, almost instantaneously, by dissociation of the resulting radical cation. Dissociation of a multiple charged peptide cation yields primarily c' and z, and, less abundantly, a, and y' type fragment species.

Electron Transfer $$[M+nH]^{n+} + [A]^{-\bullet} \rightarrow [M+nH]^{\bullet(n-1)+} + A \quad\text{Eq. 11}$$

Hydrogen emission $$[M+nH]^{\bullet(n-1)+} \rightarrow \quad\text{Eq. 12}$$
$$[M+(n-1)H]^{(n-1)+} + H^\bullet \quad\text{Hydrogen emission}$$

Recombination and Dissociation $$[M+(n-1)H]^{(n-1)+} + H^\bullet \rightarrow \quad\text{Eq. 13a}$$
$$[C_i+(m+1)H]^{(m)+} + [Z_{N-i}+(n-1-m)H]^{\bullet(n-1-m)+}$$
$$\qquad c' \qquad\qquad\qquad z$$

or $$[M+(n-1)H]^{(n-1)+} + H^\bullet \rightarrow \quad\text{Eq. 13b}$$
$$[A_i+mH]^{\bullet(m)+} + [Y_{N-i}+(n-m)H]^{+(n-1-m)}$$
$$\qquad a \qquad\qquad\qquad y'$$

The products may or may not be ionized depending on the location of the residual protons on the peptide. Here index, i, defines location of the peptide backbone cleavage, according to standard notation, for the product containing the amino terminus. The numbers, N and m, are integers that define the number amino acids in the peptide or fragment and the number of protons retained by the c, or a type fragments, respectively. The mechanisms that produce the product species in ETD are believed to be identical to those that produce the identical fragmentation observed with ECD.

In accordance with one embodiment a method of randomly fragmenting peptides within a mass spectrometer comprises the following steps:

Gas phase anions are generated from low electron affinity substrates by vaporizing inorganic and organic molecules into a Townsend discharge source or into conventional negative ion chemical ionization source operated with a buffer gas such as methane, isobutane, or argon. These sources produce an abundance of thermal electrons for capture by gas-phase organic or inorganic molecules.

The desired anion will then be injected into an ion storage device in a manner that eliminates or minimizes destruction of the anion by electron detachment. In one embodiment, this step involves injection of anions into the segmented, Thermo Electron, 2D-quadrupole linear ion trap (LTQ) along the linear axis of the device and storage of the ions in segment two of the device. Energetic collisions with the helium bath gas are minimized by this protocol. Accordingly, this procedure makes it possible to employ anions for ETD from substrates having a wide spectrum of electron affinities.

Multiply charged peptide ions will be generated by electrospray ionization and injected into an ion storage device for reaction with negative ions. In one embodiment, this step involves injection of multiply charged positive ions into the segmented, 2D-quadrupole linear ion trap along the linear axis of the device and storage of the ions in segment one of the device.

The two ion populations will be mixed in segment 2 so as to facilitate electron transfer from the anions to the multiply charged positive ions. Electron transfer from a radical to a positively charged sample ion is sufficiently exothermic to cause fragmentation of the sample molecule. In the case of peptides, the invention promotes fragmentation along the peptide backbone and makes it possible to deduce the amino acid sequence of the sample.

Reagent Anions

As noted above, any molecule that possesses a positive electron affinity (EA) (reacts exothermically to form a stable or transiently stable radical anion) can function as an electron donor and thus has the potential to be used as a reagent in the electron transfer dissociation reaction. In addition, we have also identified several compounds that form even-electron species that, when reacted with multiply charged peptides, transfer an electron and perform ETD. Thus, formation of a radical anion, is not the sole criteria for determination of whether an anion will have electron transfer capacity. Our original studies utilized anions derived from several compounds: FC-43 (perfluorotributylamine, PFTBA), sulfur hexafluoride ($SF_6$), perfluoro-1,3-dimethylcyclohexane (PDCH), hexaflourobenzene ($C_6F_6$). In this work ETD-type fragmentation were observed, but predominately the proton transfer reaction ocurred. Then we initiated the ability to isolate a specific anion species for reaction with a selected peptide ion. At that time, we discovered that background ions, not the above described species were responsible for the low-level ETD fragmentation. Isolation of the anions from both sulfur hexafloride and PDCH demonstrated that those anions solely induced proton transfer reactions and no detectable ETD was observed.

Aromatic species such as anthracene, which is converted to $C_{14}H_{10}^-$ were then investigated as the reagent. To minimize proton transfer to the anion, the use of 9,10-diphenylanthracene as a reagent can also be used. Additional aromatic compounds used as anions for promoting electron transfer dissociation include aromatic hydrocarbons (multi-cyclic aryls) and substituted aromatic hydrocarbons. In accordance with one embodiment a polyaromatic hydrocarbon having the general structure:

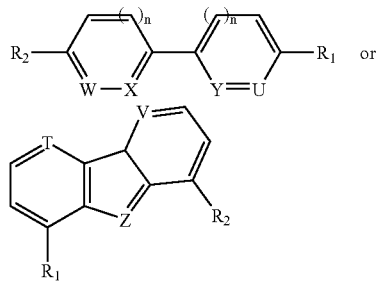

wherein n is 1 or 0;

X is selected from the group consisting of S, O, N, NH, $CR_5$, and $CHR_5$;

Y is selected from the group consisting of S, O, N, NH, $CR_6$, and $CHR_6$;

W is selected from the group consisting of S, O, N, NH, $CR_7$, and $CHR_7$;

U is selected from the group consisting of S, O, N, NH, $CR_8$, and $CHR_8$;

Z is selected from the group consisting of S, O, N, NH, $CR_3$, $CHR_3$ and —$CHR_8CHR_7$—, T and V are independently selected from the group consisting of S, O, N, NH, $CR_4$, and $CHR_4$; wherein $R_1$, $R_2$, $R_3$, $R_4$, $R_5$, $R_6$, $R_7$ and $R_8$ are independently selected from the group consisting of H, $C_5$-$C_6$ aryl, $C_5$-$C_6$ heteroaryl, halo, CN, $C_1$-$C_4$ alkyl, amino and hydroxy, or $R_1$ and $R_8$, and/or $R_2$ and $R_7$, together with the atoms to which they are bound form a $C_5$-$C_6$ aryl or $C_5$-$C_6$ heteroaryl ring or $R_7$ and $R_5$, and/or $R_6$ and $R_8$ together with the atoms to which they are bound form a $C_5$-$C_6$ aryl or $C_5$-$C_6$ heteroaryl ring or $R_2$ and $R_3$, together with the atoms to which they are bound form a $C_5$-$C_6$ aryl or $C_5$-$C_6$ heteroaryl ring.

In accordance with one embodiment, n is 1, X and Y are independently selected from the group consisting of S, O, N, NH, CH, and $CH_2$; W is $CR_7$, or $CHR_7$ and U is $CR_8$, and $CHR_8$, wherein $R_1$, $R_2$, $R_7$ and $R_8$ are independently selected from the group consisting of H, $C_5$-$C_6$ aryl, $C_5$-$C_6$ heteroaryl or $R_1$ and $R_8$, together with the atoms to which they are bound form a $C_5$-$C_6$ aryl or $C_5$-$C_6$ heteroaryl ring, and $R_2$ and $R_7$, together with the atoms to which they are bound form a $C_5$-$C_6$ aryl or $C_5$-$C_6$ heteroaryl ring. In one embodiment n is 1, X and Y are independently selected from the group consisting of S, O, N, NH, CH, and $CH_2$; W is $CR_7$, or $CHR_7$ and U is $CR_8$, and $CHR_8$, wherein $R_1$, $R_2$, $R_7$ and $R_8$ are each H, or $R_1$ and $R_8$, together with the atoms to which they are bound form a $C_5$-$C_6$ aryl or $C_5$-$C_6$ heteroaryl ring, and $R_2$ and $R_7$, together with the atoms to which they are bound form a $C_5$-$C_6$ aryl or $C_5$-$C_6$ heteroaryl ring. In another embodiment T and V are independently selected from the group consisting of S, O, N, NH, $CH_2$, and CH, Z is selected from the group consisting of S, O, N, NH, CH and $CH_2$ and $R_1$ and $R_2$ are independently selected from the group consisting of H, $C_5$-$C_6$ aryl, $C_5$-$C_6$ heteroaryl, halo, CN, $C_1$-$C_4$ alkyl, amino and hydroxyl. In another embodiment T and V are independently selected from the group consisting of S, O, N, NH, $CH_2$, and CH, $R_1$ is H, and Z is $CHR_3$, wherein $R_2$ and $R_3$, together with the atoms to which they are bound form a $C_5$-$C_6$ aryl or $C_5$-$C_6$ heteroaryl ring. In another embodiment, T and V are independently selected from the group consisting of S, O, N, NH, $CH_2$, and CH, and Z is —$CHR_8CHR_7$—, wherein $R_1$ and $R_8$, together with the atoms to which they are bound form a $C_5$-$C_6$ aryl or $C_5$-$C_6$ heteroaryl ring, and $R_2$ and $R_7$, together with the atoms to which they are bound form a $C_5$-$C_6$ aryl or $C_5$-$C_6$ heteroaryl ring. In another embodiment, T and V are each CH, $R_1$ is H, and Z is $CHR_3$, wherein $R_2$ and $R_3$, together with the atoms to which they are bound form a $C_5$-$C_6$ aryl or $C_5$-$C_6$ heteroaryl ring.

All aromatic hydrocarbons tested have some ability to induce electron transfer dissociation when reacted with multiply charged peptides. Tested anions include napthalene, fluorene, phenanthrene, pyrene, fluoranthene, chrysene, triphenylene, perylene, acridine, 2,2' dipyridyl, 2,2' biquinoline, 9-anthracenecarbonitrile, dibenzothiophene, 1,10'-phenanthroline, 9' anthracenecarbonitrile, and anthraquinone. Anions derived from all of these compounds induced electron transfer dissociation to some extent. While all of these aromatic hydrocarbons promote electron transfer, fluoranthene and 2,2' biquinoline work particularly well. The chemical structures of several of the compounds tested for their ETD-inducing ability are as follows:

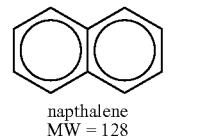

napthalene
MW = 128

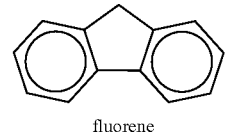

fluorene
MW = 166

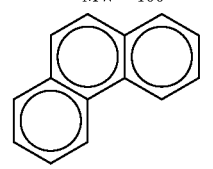

phenanthrene
MW = 178

-continued

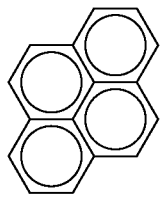
pyrene
MW = 202

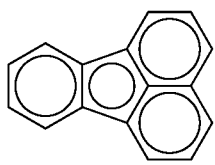
fluoranthene
MW = 202

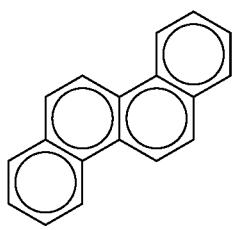
chrysene
MW = 228

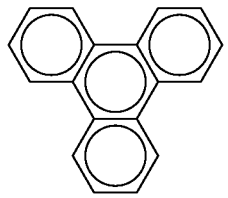
triphenylene
MW = 228

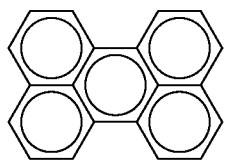
perylene
MW = 252

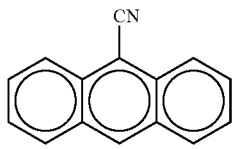
9' anthracenecarbonitrile
MW = 203

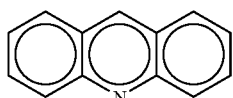
acridine
MW = 179

-continued

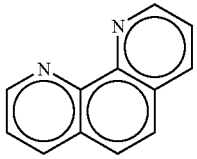
1,10' phenanthroline
MW = 180

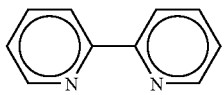
2,2' dipyridyl
MW = 156

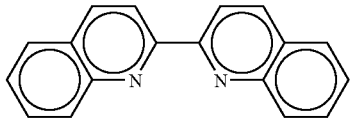
2,2' biquinoyline
MW = 256

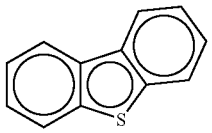
dibenzothiophene
MW = 184

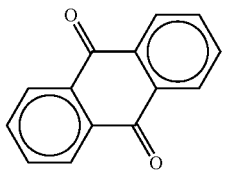
anthraquinone
MW = 208

Therefore, aromatic hydrocarbon compounds when converted to their respective anions, represent one general class of compounds that will transfer electrons to a multiply charged cation. Further, modification of these compounds to include atom(s) of sulfur, oxygen, or nitrogen (heterocyclics) should not alter their electron transfer capability and are therefore are to be included in this group electron transfer promoting compounds. Accordingly, in one embodiment of the present invention, multi-cyclic aryl and heteraryl compounds are used as anions for promoting electron transfer dissociation of polypeptides in accordace with the present invention. Table 1 presents the compound, molecular weight, and the observed m/z of its corresponding anion(s).

TABLE 1

| compound | molecular weight (Daltons) | anion m/z (Daltons/charge) |
|---|---|---|
| napthalene | 128 | 127, 128, 129 |
| fluorene | 166 | 165, 166, 180 |
| phenanthrene | 202 | 177, 178 |
| pyrene | 202 | 201, 202 |
| fluoranthene | 202 | 202 |
| chrysene | 228 | 227, 228, 229 |
| triphenylene | 228 | 227, 228, 229 |
| perylene | 252 | 252 |
| 9' anthracenecarbonitrile | 203 | 202, 203 |
| acridine | 179 | 178, 179 |

TABLE 1-continued

| compound | molecular weight (Daltons) | anion m/z (Daltons/charge) |
| --- | --- | --- |
| 1,10' phenanthroline | 180 | 179, 180 |
| 2,2' dipyridyl | 156 | 155, 156 |
| 2,2' biquinoyline | 256 | 256 |
| dibenzothiophene | 184 | 183, 184 |
| anthraquinone | 208 | 207, 208 |

Instrumentation

In accordance with one embodiment the instrument used to perform these experiments is a commercially available system that is modified to perform the steps required for an improved method of fragmenting peptides in a 2-D-multipole ion trap, a modified Finnigan LTQ (Thermo Electron Corp.). Other alternative apparatus configurations may be used incorporating other commercially available or custom-made components. The ion path mechanics or applied voltages for the ion path components between the ESI source to the RF QLT were not altered. FIG. 2 shows schematically the modifications made to the instrument.

Briefly, the Finnigan LTQ 2-D-multipole ion trap was modified as follows. A fifth differentially pumped vacuum region was attached to the rear vacuum flange of the instrument to accommodate a Finnigan MAT 4500 ion source. This region is pumped with the high vacuum stage of a dual stage turbo-molecular pump, Pfeiffer model TMH 230-160 backed Alcatel 2008A-rotary vane mechanical pump. Two RF octopole ion guides, labeled Rear Octopole #1 and Rear Octopole #2, were used to transport ions emanating from the Finnigan MAT 4500 ion source. The aperture of the plate lens (Rear Inter-Octopole Lens) which separates the two RF octopole ion guides, serves as the differential pumping conductance limit between the added vacuum stage, Vacuum region #5 and the vacuum region of the LTQ containing the RF linear quadrupole ion trap, QLT. Rear Octopole #1 is composed of a pair of 2 inch long octopole electrode assemblies ($r_0$=0.108 in.), from a Finnigan LCQ placed end to end and electrically connected as one unit. Rear Octopole #2 is simply a single LCQ octopole electrode assembly. The RF QLT assembly was not mechanically modified. However the electrical connections of the Front Lens and Back Lens electrodes have been changed to enable superposition of a RF voltage on to the DC bias voltages for theses lenses provided by the standard electronics.

The ion source lens voltages are supplied by a Finnigan MAT 4500 PPNICI Control Module and the filament power and emission control is supplied by a Finnigan MAT 4600 Quadrupole Electronics Module (QEM). Source heater power and regulation is provided by a home built unit based on a Omega Model CN9000A temperature controller and a 1.5 A 24VAC transformer. The source calibration gas solenoid valve is operated by another homebuilt unit. The source's standard probe vacuum interlock bellows valve has been replaced with a ball valve [A and N Corporation]. Provision is made for the rough evacuation of the probe interlock and the calibration gas inlet with a set of toggle valves and Alcatel Model 2012 mechanical pump.

The rear octopole RF and DC voltages as well as the RF voltage for the QLT end lenses are provided by home build electronics modules which use modified circuitry from Finnigan LCQ and TSQ 7000 instruments. Both octopoles are driven with the same RF voltages though they have separate DC bias voltages. Similarly the QLT end lenses receive the same secondary RF voltage but have separate DC bias voltages. Two frequency synthesizers, Wavetek/Rockland Model 5100 and Stanford Research Systems Model_DS340, provide, respectively, the reference frequencies for the octopole and end lens RF electronics. The amplitudes of both the rear octopole and end lens RF voltages are controlled by spare DACs (Digital to Analog Converters) in the LTQ electronics. The instrument's embedded computer control system was reconfigured to enable control of these voltages during the execution of mass spectral experiments (scan functions).

When operated in the negative chemical ionization mode, the ion source lenses, L1, L2 and L3 (where L1 is the lens closest to the ion volume and L3 is the farthest) have DC bias voltages of +10V, +70V and +23V respectively. For transmission of anions to the QLT, the RF voltage between adjacent rods is typically about 300 Volts zero-to-peak at a frequency of about 2.2 MHz. The rear octopole RF amplitude is made zero when the anion transmission to the QLT is to be interrupted (gated off).

The standard nano-flow ESI source was used for the instrument. For most of the work, mixtures of standard peptides in 40% aqueous acetonitrile w/0.1% acetic acid were infused at 100 nl/min. The source was used without modification. For the LC/MS experiments, the source had to modified to appropriately mount and electrically connect to the homemade packed capillary HPLC columns with integral laser pulled electrospray emitters that we use in our laboratory.

The computer programs that govern the control of mass spectrometer to perform the ETD MS/MS experiment were modified. The operation of radial ejection RF quadrupole linear traps has been described in detail in Schwartz et. al. (J. Am. Soc. Mass Spectrom. 2002, 13, 659-669). The instrument described in that article is the direct precursor to the Finnigan LTQ. Basic steps of the operation of the device are shown in FIGS. 5A-5H and discussed in detail below.

Operating Procedure

Multiply charged peptide cations were generated by electrospray ionization (ESI). A 40% aqueous acetonitrile solution (with 0.1% acetic acid), containing peptides at 1 pmol/μL, was infused into a SilicaTip™ fused silica emitter (30 μm tip, New Objective, Woburn, Mass., USA). Peptides studied include adrenocorticotropic hormone fragment 1-24 (ATCH hormone, Sigma-Aldrich, St. Louis, Mo., USA), and an in-house synthesized phosphopeptide. Negative chemical ionization, with methane buffer gas (MG Industries, Malvern, Pa., USA), was used to produce anions of $SF_6$ (MG Industries, Malvern, Pa., USA) and PDCH (Sigma-Aldrich, St. Louis, Mo., USA). A Finnigan LTQ linear ion trap mass spectrometer (ThermoElectron, San Jose, Calif., USA) was adapted to accept a Finnigan 4500 chemical ionization source (Finnigan, Sunnyvale, Calif., USA), which was mounted on the rear side of the device—opposing the factory nanospray source. The sequence of scan events includes: precursor ion isolation (within the linear quadrupole ion trap), introduction of anions for ion/ion reactions, and finally mass analysis of the product ions as describe in more detail as follows:

1. Injection of cations generated by the ESI source into the QLT where they are collisionally stabilized and trapped. FIG. 5A The injection of cation into the ion trap is depicted in FIG. 5A. The skimmer electrode of the atmospheric pressure interface is maintained at ground potential, 0 volts, thus the cations entering the QLT have essentially zero kinetic energy at 0 volts. Hence biasing the Back Lens electrodes at ground potential, raises that DC axis potential so that injected ions which have undergone a few dissipative collisions with the background are reflected back toward the front of the device. Injected ions undergo many further momentum depleting collisions with the Helium (about 3 mTorr) atoms efficiently damping their axial motion and causing them to be trapped in the axial DC well created by the low bias potential of the Center Section of the device. These collisions also damp the radial motion of the ions such that ions, under the influence of the radial strong focusing effect of the RF quadrupole field, relax to the vicinity of the central axis of the device. Unless subjected to further kinetic excitation, collisions with Helium will reduce the kinetic and internal energies of the trapped cations to near thermal levels within about 1-2 msec. Without further kinetic excitation ion energies will be well below 1 eV. Fully collisionally relaxed trapped ions will remain confined to within about 1.0 mm of the central axis.

Generally, to avoid space charge effects that interfere with the proper performance of the QLT, it is desirable to prevent accumulation of ions of mass-to-charge ratios other than those within the desired precursor m/z range. This is accomplished by superposing a supplementary dipolar broadband AC field on to the RF quadrupole trapping field to resonantly eject ions of which have characteristic frequencies of motion in the quadrupole field (motion transverse to the device's axis) that deviate from those of ions within the precursor m/z window. The optimal intensity of the RF quadrupole field for the injection and accumulation of precursor ions does not allow efficient accumulation of precursor ions and achievement of a m/z isolation band of about 3 Th (Daltons/unit charge) or less that is generally required. So "injection waveform" isolations are, by necessity, rather coarse, typically, only preventing the accumulation of ions with m/z ratios outside of about ±2-10% of the precursor m/z ratio.

2. Precursor m/z isolation. FIG. 5B

Within a few milliseconds after termination of cation injection and cessation of any application of an "injection waveform" field, the intensity of the RF quadrupole trapping field may be increased such that ion isolation may be effected with the desired m/z resolution and high efficiency (lowest loss of precursor ions). A higher resolution "waveform" field is applied so that all cations outside of the desired precursor m/z window are resonantly ejected from the QLT. Normally more than 90% of the precursor ions are retained. During m/z isolation, the DC bias potentials of the Front Section and Back Section of the QLT are maintained at about +12 volts relative to the Center section to confine the cations within the Center Section of the device.

3. Relocation of precursor cations to the Front Section of the QLT. FIG. 5C

After precursor m/z isolation is complete, the DC bias potential of the Front Section is reduced to 1 volt below that of the Center Section. The Front lens DC bias is maintained above both those of the Center Section and Front Section to maintain axial confinement of the Cations. Within a few milliseconds, all of precursor ions initially in the Center Section diffuse to the Front Section, where again, damping collisions with Helium atoms cause them to remain.

4. Injection of anions generated by the NICI source into the QLT where they are collisionally stabilized and trapped in the Center Section of the device FIG. 5D.

Once the precursor ions have been moved to the Front Section, the DC bias potentials of the Center Section, Back Section and Back Lens are elevated above "ground" potential to permit injection and trapping of the anions. The NICI source is biased at 0 volts so maintaining the Front Section at a negative DC bias voltage both maintains trapping of the precursor cations, and creates an axial potential barrier at the front of the device for the negative ions. The DC bias of the Center Section is made more positive then that of the Rear Section so that in the anions accumulate in this section of the device. This step corresponds to the injection and accumulation of cations in Step 1, except that the anions are injected from the back end of the device and, because anions are by definition negatively charged, the DC bias potentials have opposite signs.

During anion injection it is technically feasible to apply an "injection waveform" to resonantly eject anions which have neither m/z ratios close to that of the desired reagent anions nor m/z ratios close to those of the previously selected precursor cations. However, we suspect that the kinds of anions that are most likely to promote ECD will readily undergo electron detachment if they are subjected to even modestly energetic collisions. Thus any extra kinetic excitation of the reagent anions beyond that associated with ion injection might cause loss of the very anions that we wish to isolate. So reagent anion isolation during injection may be undesirable. The typical duration for anion injection is anywhere from 1 ms to 1 sec. (ideally just a few milli-seconds) depending upon the anion current provided by the NICI source.

5. Reagent anion m/z isolation or m/z elimination. FIG. 5E

Within a few milliseconds after termination of anion injection, the intensity of the RF quadrupole trapping field may be adjusted such that isolation of the precursor may be effected with the best attainable m/z resolution and efficiency. Such Reagent anion m/z isolation is depicted in FIG. 5E. As mentioned above, the anion isolation "waveform" must resonantly eject anions which have neither m/z ratios close to those of the desired reagent anions nor close to the m/z rations of the previously selected precursor cations. Thus undesired anions of m/z ratios close to that of the selected precursor m/z window will not be ejected. This arrangement is not ideal. However it will require substantial changes in the design of the QLT and/or the voltages that drive it to circumvent this problem. The current implementation does insure that most undesired anions are eliminated from the trap prior to the initiation of cation-anion reactions.

A fundamental attribute of ion motion in an RF-only quadrupole trapping field is that at any particular intensity of the RF quadrupole trapping field, there is a corresponding threshold m/z ratio (which is proportional to the intensity of the field) for ion trapping. Only ions with m/z ratios above this threshold m/z ratio may be trapped. Ions with m/z ratios below this threshold are radially ejected. We have often used the simple manipulation of the magnitude of the RF voltage applied to the QLT electrode to eliminate undesired anions species below the m/z of the reagent anions of interest.

A simple method of determining which anions promote ECD is to resonantly eject a relatively narrow window of m/z, corresponding to a targeted anion species, using a single frequency "waveform" prior to or during the ion-ion reaction step. Such an approach should cause less kinetic activation of the anions retained in the trap thus reducing the probability of anion loss due to electron detachment.

6. Mixing of precursor cations and reagent anions to cause cation-anion reactions and the production of ETD product ions. FIG. 5F

Once the desired trapped precursor cation and reagent anion populations have been established and have been allowed to collisionally relax, a secondary RF voltage is applied to both the end lens plates of the QLT (According to our nomenclature the RF voltages applied to the QLT electrodes to effect radial containment are primary RF voltages). The effect of this secondary RF potential is to repel both positive and negative ions. For any given m/z this repulsive effect can be modeled as repulsive potential that varies inversely with m/z. and is referred to in the literature as a pseudo-potential or effective potential. To effect simultaneous trapping of both anions and cations in the same region of the QLT, and thus permit cation-anion reactions to occur, the DC bias voltages applied to the trap segments and end lenses are made equal (nominally 0.000 volts). The pseudo-potentials established by the secondary RF voltages applied to the end lenses provide the necessary axial trapping for both the cations and anions. This is depicted in FIG. 5F.

In all of the work presented here, a secondary RF voltage with an amplitude, $V_2$, of 100 V (0-peak) and a frequency, $f_2$, of about 600 kHz (½ the frequency of the quadrupole field, $f_1$) is applied to both end lenses during the cation-anion reaction interval. It provides efficient simultaneous trapping of ions of both polarities with m/z ratios ranging from below 100 u to beyond 2000 u. The axial pseudo-potentials only have significant action in the close vicinity of the end lenses; so both the anions and cations diffuse throughout all three sections of the device and are free to react. Presently, we are only able set the DC biases of the three sections of the QLT to be equal to within about ±0.030 volts. A single increment of the DACs which control these bias voltages corresponds to a about 0.063 volt change in bias voltage. Since the mean thermal kinetic energy of an ion at 300° C. is about 0.030 eV, these small differences in bias potentials could be causing some axial segregation of the trapped anions and cations. However, as we observe abundant cation-anion reaction products, this doesn't appear to be happening in a gross sense. The trapped ion populations are probably sufficiently high to create a compensating space charge potential in every segment. The ions should distribute themselves to provide a uniform axis potential, thus allowing free movement of ions along the device axis. It is conceivable that the axial mobility of ions could be m/z dependent as lower m/z ions are generally confined closer to the central axis. This could possibly be the origin of the observed dependence of the production of ETD product ions on precursor m/z. Therefore it would be preferred if the DC bias potentials of the three segments match within about ±0.001 volts during the cation-anion reaction period. Such bias differences should have negligible anion-cation segregation at laboratory temperature. It may be possible to avoid cation-anion segregation by alternating the sign of the bias differences repetitively so that the trapped ions are constantly forced to axially redistribute and therefore stay mixed.

The larger the reagent anion population, the more rapid the conversion of precursor ions to product ions. With suitably large reagent anion populations, ion-ion reaction periods of 30-100 ms are typically adequate to react most of the precursor cations. For the results shown herein, about 3,000-30,000 precursor ions were typically isolated (this assumes that the precursor species was triply charged, and corresponds to AGC MS$^n$ target values of 10,000-100,000). The initial number of reagent anions available for ion-ion reaction was probably a least about 3-10 fold greater than the initial population of precursor ions. As discussed earlier, the initial number of the reagent anions of types which promote ETD probably varied by orders of magnitude depending upon the compounds that were introduced to the NICI ion source.

The ETD and proton transfer product ions potentially can undergo further reactions with reagent anions. Such secondary reactions will cause neutralization and therefore loss of any singly charged cation products. It also will likely produce second generation product ions which contain neither the N nor the C terminus of the originating precursor peptide cation. Such "internal fragment" product ions are undesirable as they complicate interpretation of the resulting product ion mass spectrum. Methods have been developed for charge reduction (proton transfer) ion-ion experiments in 3D RF quadrupole ion traps to inhibit such secondary reactions [see U.S. Patent Application Publications Nos. US 2002/0092980 and US 2002/0166958, the disclosures of which are incorporated herein]. It is anticipated that these methods can be adapted to inhibit secondary reactions between reagent anions and ETD product cations in 2D RF quadrupole ion traps.

While perhaps undesirable in terms requiring longer reaction times, longer ion accumulation times, and perhaps higher minimum sample levels, using a large ratio of precursor cations to reagent anions would produce fewer secondary product ions. Since the precursor cation population would always be much larger than the product cation population, anions would be much more likely to react with precursor ions than with product ions. It is conceivable that the ratio of precursor ions to reagent ions could be adjusted automatically depending upon the accumulation rate of the precursor (rate of production of precursor ions from the ESI source) thereby reducing the production of secondary product ions when precursor ions are plentiful.

In our present experiments, proton transfer generally produces large numbers of primary and secondary product ions. For example, a quadruply charged precursor ion, $[M+4H]^{4+}$, through a succession of proton transfer reactions, produces triply charged primary product ion, $[M+3H]^{3+}$, as well as doubly charged, $[M+2H]^{2+}$, and singly charged, $[M+H]^+$, secondary product ions. The secondary product ions may have the same m/z ratios as ETD product ions thus interfering with their observation. Continuous resonant ejection of the primary proton transfer product ions during the cation-anion reactions eliminates the production of such interfering secondary proton transfer product ions. This also prevents the production and observation of secondary ETD product ions from primary and secondary proton transfer products. We have successfully demonstrated this procedure though it was not used for the collection of the data shown herein.

7. Termination of ion-ion reactions and preparation for mass analysis of product ion. FIGS. 5G and 5H.

To end the cation-anion reactions, the DC bias voltage of the Center Section is lowered relative to the DC biases of the end sections and the end lenses. Within a couple of milliseconds, all of the cations migrate to the center section and all of the anions migrate to the end sections of the QLT. Then the axial trapping RF voltages (Secondary RF voltage) applied to end lens plates is turned off releasing the anions. This is depicted in FIG. 5G. For diagnostic purposes it is often useful to obtain a m/z spectrum of the unreacted reagent anions. This can be readily accomplished by terminating the cation-anion reactions by razing the relative DC bias of the Center Section instead of lowering it as described above. This retains the anions in the Center Section and axially extracts the cations. This is depicted in FIG. 5H.

Prior to mass analyzing the product cations, it may be desirable to eliminate by resonant ejection cations with specific m/z ratios. Likely candidates for elimination would be unreacted precursor ions and proton transfer product ions (charge reduced product ions). Given the currently attainable precursor to ETD product efficiencies of ca 10-20%, a reasonable strategy for obtaining suitable numbers of ETD product ions is to isolate a substantial excess (about 5-10 fold) of the quantity of precursor cations that could be directly m/z analyzed and meet the instrument specifications for m/z assignment accuracy and resolution (spectral space charge limit [25]). However after the cation-anion reaction step, the total number of retained ETD product ions (and more specifically, the total charge of the retained ETD product ions) is within the spectral space charge limit.

Eliminating the excess charge associated with retained unreacted precursor ions and any retained proton transfer product ions enables mass analysis of the ETD product ions with good m/z accuracy, resolution. Since the total charge of the retained ETD product ions is near the spectral space charge limit, the dynamic range of the product ion spectrum the highest that the instrument can provide. This will improve the observation of minor component ETD product ions (ie. small ETD peaks).

8. Mass analysis of final population of ions

A m/z spectrum of the final population of ions of either chosen polarity is obtained in the conventional manner [Bier-Syka, Schwartz et al.]. The ions are m/z sequentially resonantly ejected though slots in the rod electrodes to an ion detector.

Of the eight steps to the experiment enumerated and discussed above, steps 1, 2, and 8 are essentially unchanged from the standard QLT MS/MS experiment using CAD. It should be understood that the above procedure is generally performed as part of a greater sequence of experiments. Cation injection times would normally be determined from a prior experiment (or experiments) which allow estimation of the rate of accumulation of precursor cations in the trap during the cation injection step, 1, and a predetermined target amount of total precursor cation charge to be used in the experiment. This approach to the regulation of stored ion charge (space charge) in RF quadrupole ion trap mass spectrometers is known in the art as Automatic Gain Control (AGC). It is anticipated that an appropriate AGC scheme could also be used provide control of reagent ion population used for the cation-anion reactions. In the data presented herein the standard MS/MS LTQ AGC prescan was used to provide regulation of the precursor cation charge after the precursor isolation step. No automated regulation scheme has yet been implemented for the selected reagent anions.

Implicit in the ordering of the events of the above procedure is the assumption that m/z of the cation precursor is greater than that of the reagent anions. If the reagent anions are to be m/z isolated and have m/z ratios much greater than the specified precursor m/z window it may be desirable to reverse the sequence of cation and anion injection and isolation. The trapping conditions for optimal isolation of the reagent anions may be incompatible with trapping of the lower m/z cations. In this case the anions would be injected first and collected in the Center Section. The reagent anions would be m/z isolated and then relocated the Back Section. Then the cations would be in injected and trapped in the Center Section and the precursor cations would be m/z isolated without causing resonant ejection of the reagent anions. The rest of the experiment would be the same as described above.

The above discussion has focused on implementation of ETD on a RF QLT mass spectrometer. Various mass spectrometer systems which utilize charge sign independent ion trapping in RF multipole linear ion traps for ion-ion type experiments are suited to performing ETD MS/MS experiments. In one embodiment an RF trap apparatus suitable for performing precursor cation and reagent anion isolations as well as for performing the charge sign independent trapping for the ETD process would be the 6 segment trap. This device would essentially constitute a QLT constructed from a pair of three segment traps (like LTQ device) placed end on end. Such a "dual" three segment trap would allow independent m/z isolation of both the precursor cations and reagent anions. Obviously one of the halves of this "dual" trap could also serve as the scanning m/z analyzer. If m/z selection of the precursor cations and anions is done prior to their injection into the RF quadrupole linear trap, then 2 or 4 segment (depending on if the Secondary RF voltages for axial trapping are applied to the end plate lenses or as dipolar voltages between apposing rods in the end sections) would be quite satisfactory.

Using the procedures of the present invention in combination with the isolation of single anions for reactions with multiply charged peptide cations will significantly impact the application of mass spectrometry to proteomics. For example, the entire collection of proton transfer experiments defined by McLuckey et al. (e.g., charge-state reduction, gas-phase concentration, ion parking, etc.) is now available in tandem with ETD, and CAD on the same mass spectrometer with a time-scale permitting data-dependent operation and chromatography. Examples of such experiments include conversion of multiply charged cations to a selected charge-state via proton transfer reactions (Ion Parking). After the signal has been concentrated into one charge-state, the cations are then subjected to an anion that induces electron transfer to generate ETD product ions. If the selected cation was highly charged, an additional step of charge-state reduction could be performed simply by the injection of the proton transfer anion. The net result is a mass spectrum comprising singly or doubly charged c and z products (within the resolving power of the linear ion trap) derived from the prior concentration of various multiply charged precursors. Obviously, charge-state reduction of ETD product ions is easily performed without an initial step of ion parking, as described above.

In some cases, especially with proteins or large peptides, the mass spectrometer could be operated in the following sequence: (1) gas-phase concentration (ion-parking), (2) ETD of the intact precursor, (3) CID of intact precursor to produce a number of multiply charged fragment ions, which are then sequentially exposed to (4) ETD. The resultant ETD spectra (those formed from step 4) would represent sequence information derived from the precursor b or y ion. Such a strategy would combine the strengths of the increasingly popular "top-down" protein sequencing method (step 2), with those of the more conventional "bottom-up" approach (steps 3 and 4). To a certain extent, step 3 (CID is known to favor certain cleavages, e.g., N-terminal side of Pro and C terminal to His) is analogous to enzymatic digestion used in conventional "bottom-up" proteomics, but for a few differences. Namely, acquisition of MS3 spectra from each b, y product (e.g., peptide MS/MS spectra) generates sequence information from which the protein molecular mass and ETD product spectra are known.

EXAMPLE 1

Use of Anions for Electron Transfer Dissociation of Polypeptides

In accordance with one embodiment FC-43 (perfluorotributylamine, PFTBA), sulfur hexafluoride ($SF_6$), perfluoro-1,3-dimethylcyclohexane (PDCH), hexafluorobenzene ($C_6F_6$), and anthracene were introduced into the NICI (negative ion chemical ionization) source to produce anions for the experiment. In all cases, anions created in the source have produced at least some ETD products when reacted with a standard peptide precursor ion. When FC-43, the standard m/z calibrant used for mass spectrometers with electron impact ionization sources, was introduced to the source a few c and z ions were produced with very low precursor to ETD product conversion efficiency. In subsequent experiments, the above mentioned molecules were introduced into the ion source separately and all produced extensive c and z type fragmentation of our standard precursor ion, the triply charged phosphopeptide (LPISASHpSpSKTR)$^{+3}$; SEQ ID NO: 1. Precursor to ETD product conversion efficiencies ranged from about 0.1-1% for $SF_6$ and PDCH, about 0.5-5% for ($C_6F_6$) and about 5-20% for anthracene and 9,10 diphenyl-anthracene.

The other source of anions that has produced precursor to ETD product conversion efficiencies nearly as high as those observed with anions derived from anthracene, was the "residual" or "background" gases in the CI ion source. Prior to this experiment increasing the number of precursor ions present when the ion-ion reactions were initiated did not increase the number of ETD product ions (in absolute numbers). This was curious since it was believed that throughout the ion-ion reaction period many more anions were present in the ion trap than there were precursor cations. Furthermore, it was verified at the end of the ion-ion reaction period the anion population was not depleted. Under these conditions, the number of ETD products generated should be nearly proportional to the initial number of precursor cations (first order kinetic theory should apply). Indeed, proton transfer products appeared to be produced in approximate proportion to the initial number of precursor ions. If ETD products were being produced by reactions with a minor component (or components) of the mixture of anions and the minor component of anion was being depleted during the ion-ion reaction period the observations could be explained.

One possibility was that the hypothesized minor component anions were derived from residual background gases (contamination) in the ion source that was responsible for the production of the ETD product ions. In this experiment there were residual amounts of FC-43, $SF_6$, PDCH, and $C_6F_6$ as well as various unknown background compounds which produced ions by electron capture in the CI ion source and were used as the reagent anions. When an abundant reagent anion population derived from "background" compounds was used, the number of ETD product ions produced became proportional to the initial number of reagent ions. The precursor to ETD product efficiency of the experiment also improved substantially.

The procedure was modified to allow for the ability to resonantly eject a selected narrow m/z range of ions from the ion trap, and thus include or exclude a specific reagent ion species from being present during the ion-ion reaction period. The facility of prominent reagent anions derived from ion source "background" compounds to produce ETD products was probed in this manner. The exclusion of a reagent anion species having m/z 181 (mono-isotopic m/z) during the ion-ion reaction period reduced the production of ETD products by a factor of about 3-5 relative to that of the proton transfer products which were not substantially reduced. This species is believed to be $C_6F_5CH_2^-$, formed by an ion molecule reaction between $C_6F_6.^-$ and methane, $CH_4$, in the NICI ion source. In addition the reagent anions derived from anthracene (via ion molecule reactions of $C_{14}H_{10}.^-$ and $CH_4$), also promote ETD. When anthracene is introduced to the NICI source to produce these reagent anions, ETD product ions are produced in proportion to the initial number of precursor cations. Variations in the ratio of proton transfer to ETD products, with changes in the RF voltages applied to QLT during the ion-ion reaction period, was also observed.

EXAMPLE 2

Figure 3:
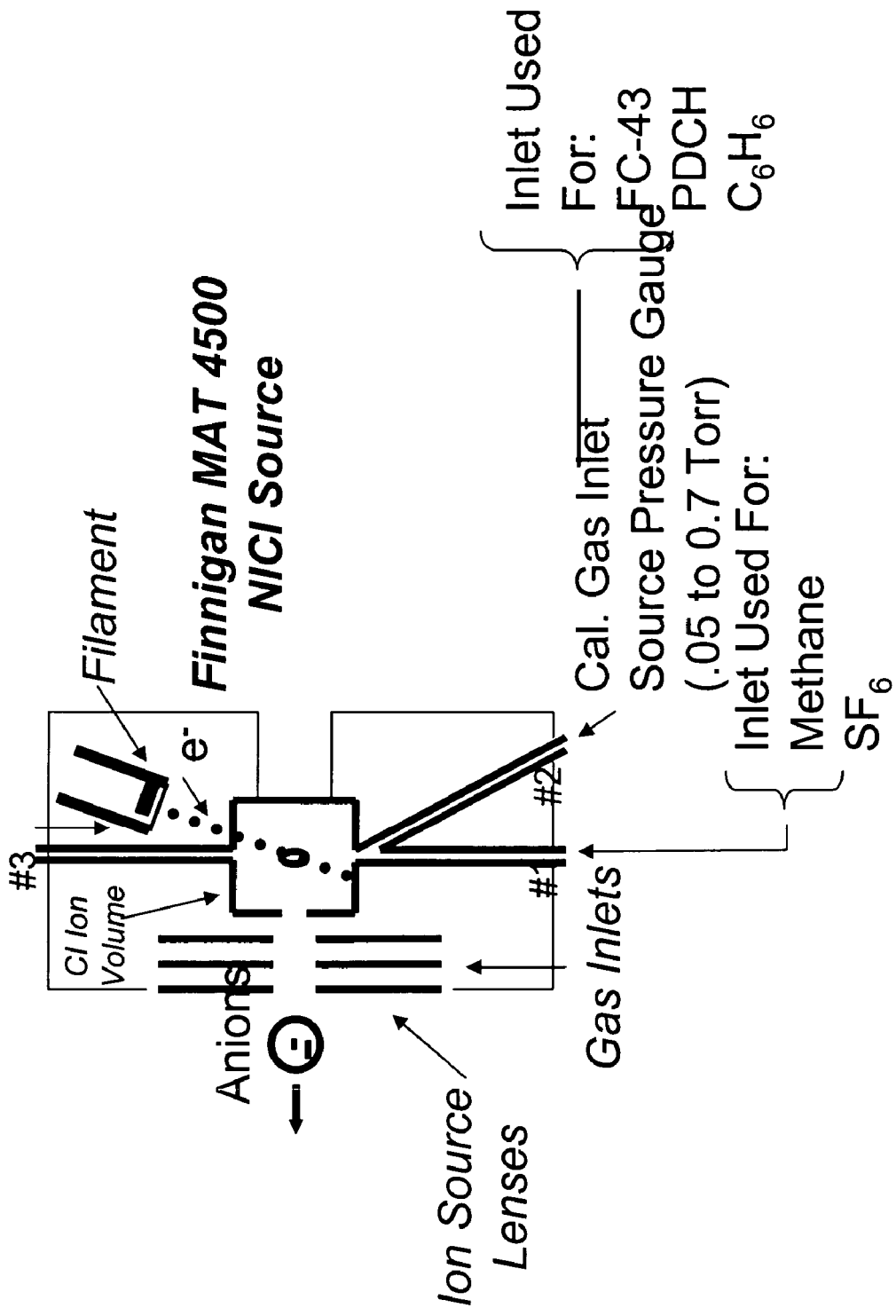
FIG. 3 is a schematic representation of the Finnigan MAT 4500 NICI source.
Figure 4:
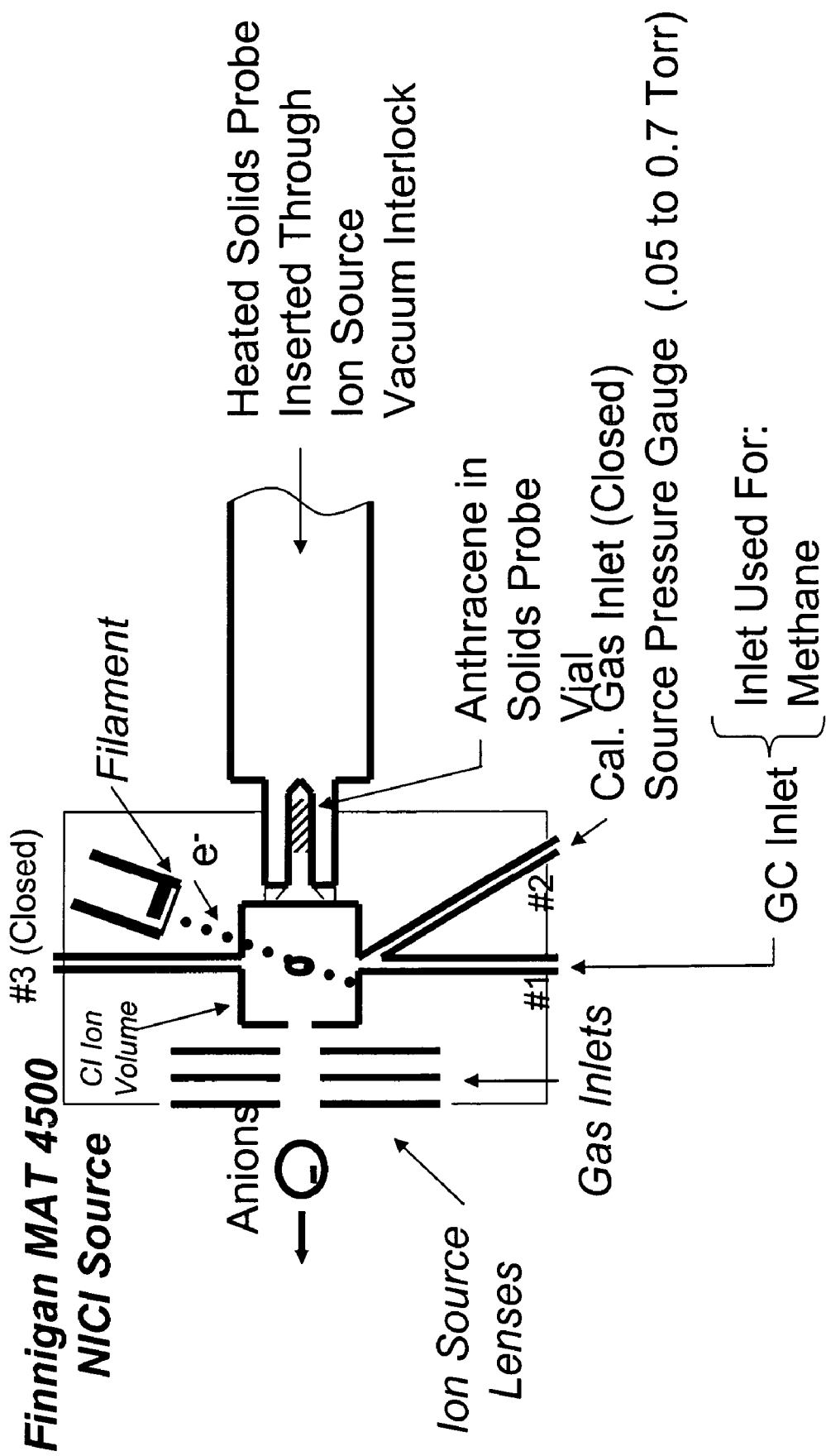
FIG. 4 is a schematic representation of the Finnigan MAT 4500 NICI source showing how (in initial experiments) anthracene was introduced with a solids probe vial.

Polypeptide Sequence Analysis by Electron Transfer Dissociation Mass Spectrometry Instrument Modification and Operation All experiments were performed with a commercial QLT, the Finnigan LTQ mass spectrometer (Thermo Electron, Waltham, Mass.) equipped with a modified nanoflow electrospray ionization (ESI) source (See FIG. 2-4). The LTQ was modified to accommodate a Finnigan 4500 CI source (Thermo Electron) placed at the rear of the instrument. The anion beam was gated by on/off control of the RF voltages applied to the octopole ion guides, which transport the anions from the CI source to the QLT. FIGS. 5A-5H display schematics of the linear ion trap with ESI and CI sources located at either end of the three-segment device. To generate and analyze the products of ion/ion reactions, instrument control software (ITCL code) was modified to incorporate the scan events diagrammed in FIGS. 5A-5H into the standard QLT MSn scan function.

Sample Introduction.

Multiply charged (protonated) peptides were generated by ESI. A 40% aqueous acetonitrile solution (with 0.1% acetic acid), containing peptides at 1 pmol/μl, was infused from a SilicaTip fused silica emitter (30-μm tip, New Objective, Woburn, Mass.). Samples included angiotensin I (DRVYIH-PFHL; SEQ ID NO: 2, Sigma-Aldrich) and the in-house-synthesized phosphopeptides: LPISASHpSpSKTR (SEQ ID NO: 1), APVAPRPAApTPNLSK (SEQ ID NO: 3), and DRpSPIRGpSPR (SEQ ID NO: 4). Negative CI, with methane buffer gas (MG Industries, Malvern, Pa.), was used to produce negative ions of anthracene (Aldrich). Anthracene was introduced to the CI source through an improvised heated-batch inlet consisting of a gas chromatograph oven and a heated transferline assembly (Thermo Electron) connected to a fused silica restrictor column (see FIG. 4). Helium is used as a carrier gas to sweep the volatilized reagent molecules through the heated capillary restrictor into the CI source.

Chromatography.

An Agilent (Palo Alto, Calif.) 1100 series binary HPLC system was interfaced with the QLT mass spectrometer for online peptide separation and analysis by nHPLC-micro-ESI-MS (nHPLC-μESI-MS/MS).

Synthetic Peptide Analysis.

A mixture of 10 synthetic peptides (1-100 fmol) was loaded onto a polyimide-coated, fused-silica microcapillary "precolumn" (360 μm o.d.×75 μm i.d.; Polymi-cro Technologies, Phoenix) that was butt-connected with polytetrafluoroethylene tubing [0.06 in o.d.×0.012 in i.d. (1 in=2.54 cm), Zeus Industrial Products, Orangeburg, S.C.] to an analytical column. This column (360 μm o.d.×50 μm i.d.) was made with 5 cm of 5-μm C18 reverse-phase packing material (YMC, Kyoto) and equipped with an integrated, laser-pulled, electrospray emitter tip (Martin et al., (2000) Anal chem. 72: 4266-4274). Peptides were eluted at a flow rate of 60 nl/min with the following gradient: 0-100% B in 17 min, 100-0% B in 18 min [A, 100 mM aqueous acetic acid (Sigma-Aldrich); B, 100 mM acetic acid in 70:30 acetonitrile (Mallinckrodt)/water]. Spectra were recorded under data-dependent settings. The instrument cycled through acquisition of a full-scan mass spectrum (300-600 m/z) and three ETD MS/MS spectra recorded on the three most abundant ions in the full-scan mass spectrum (1 sec per cycle).

Complex Mixture Analysis.

A 300-μg aliquot of purified nuclear proteins was digested with trypsin (Promega; 1:20, enzyme/substrate) in 100 mM $NH_4HCO_3$ (pH 8.5) overnight at 37° C. The solution was acidified with acetic acid and taken to dryness. Peptides were converted to methyl esters (Ficarro et al., (2002) Nat. Biotechnol. 20, 301-305). Reagents were removed by lyophilization, and the sample was reconstituted in a mixture containing equal parts MeOH, MeCN, and 0.01% acetic acid. Enrichment of phosphopeptides was performed by loading half of the sample onto an $Fe^{3+}$-activated immobilized metal affinity chromatography column (360 μm o.d.×100 μm i.d.) packed with 6 cm of POROS 20 MC metal chelate affinity-chromatography packing material (Per-Septive Biosystems, Framingham, Mass.). Phosphopeptides were eluted onto a C18 microcapillary precolumn (described above) by using 15 μl of 250 mM ascorbic acid (Sigma). The precolumn was butt-connected to an analytical column (described above), and phosphopeptides were eluted with the following gradient: 0-60% B in 60 min; 60-100% B in 70 min. Spectra were recorded as described above except that the top five most abundant ions in the full-scan MS were selected for MS/MS (ETD; cycle time, 1.5 sec).

Results

Figure 6:
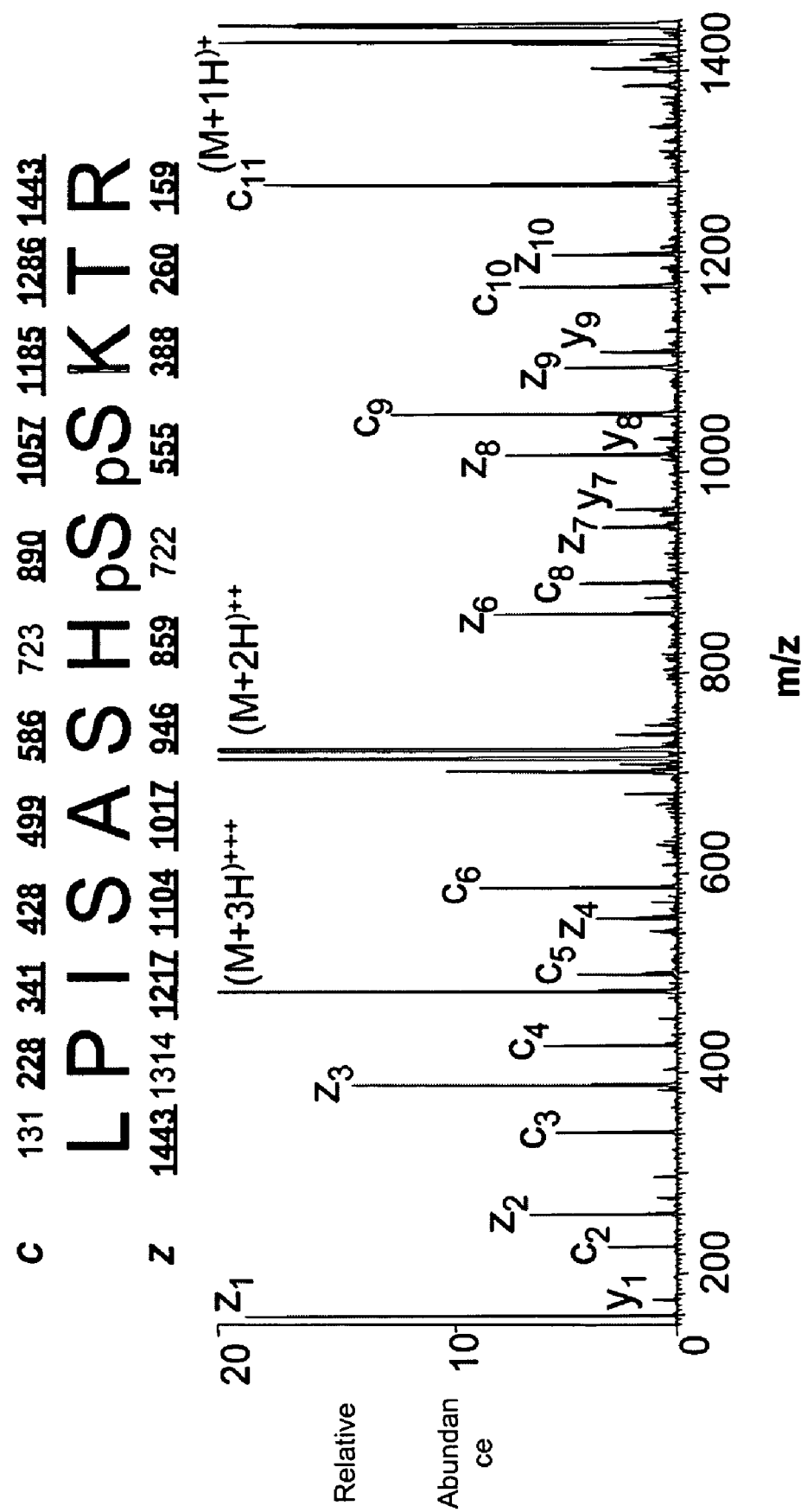
FIG. 6 represents data from a single-scan ETD MS/MS spectrum resulting from a 50-msec reaction of the triply charged phosphopeptide, LPISASHpSpSKTR (SEQ ID NO: 1), at m/z 482, with anthracene anions. Predicted m/z values for fragment ions of types c and z are shown above and below the sequence, respectively. Those observed are underlined. Note that both z5 and c7 have m/z values that overlap with the ion cluster containing the product of proton abstraction, the $(M+2H)+2$ ion at m/z 722. All other possible ions of types c and z appear in the spectrum. The total experiment time was 300 msec.

Shown in FIG. 6 is a single-scan ETD mass spectrum recorded on $(M+3H)^{+3}$ ions from the doubly phosphorylated, synthetic peptide LPISASHpSpSKTR (SEQ ID NO: 1). Total acquisition time for this spectrum was 300 msec. Positive ions to be dissociated were generated at the front end of the QLT by ESI of an infused solution containing the sample at the 1 pmol/μl level. The resulting full-scan spectrum contained a mixture of $(M+3H)^{+3}$ and $(M+2H)^{+2}$ ions at m/z 482 and 722, respectively Reagent anions for the electron transfer reaction were generated in a CI source attached to the back of the QLT. Bombardment of methane gas at 1 torr (1 torr=133 Pa) pressure with 70-eV electrons generates positively charged reagent ions, $CH_5^+$ and $C_2H_5^+$, plus a population of thermal or near-thermal electrons. When anthracene, $C_{14}H_{10}$, is volatilized into the CI source, the major anions produced are even-electron species, m/z 177 and 179, having the formulas $C_{14}H_9^-$ and $C_{14}H_{11}^-$, respectively.

When $C_{14}H_9^-$ and $C_{14}H_{11}^-$ are reacted (for approximately 50 msec) with (M+3H)+3 ions from LPISASHpSpSKTR, they function both as bases and as one-electron reducing agents. Proton abstraction generates the (M+2H)+2 and (M+H)+ products observed in the ion clusters centered at m/z 722 and 1443, respectively. Also present in these clusters is a population of ions having compositions corresponding to (M+3H)+2 and (M+3H)+, respectively. Isolation and collision activation of these ion clusters yields a mixture of c- and z-type fragment ions from the odd-electron ion components and b- and y-type fragment ions from the even-electron ion components (data not shown). From the isotopic distribution we estimate that 30-50% of the charge-transfer product ions are noncovalently bound yet dissociated precursor ions. These are easily dissociated by CAD.

Electron transfer also leads to the direct generation of c- and z-type fragment ions. In FIG. 6, m/z values for predicted c- and z-type product ions derived from this sample are shown above and below the peptide sequence. Those observed are underlined and account for 31% of the total product-ion current. Note that only four members of c- and z-type ion series are missing. Two of these occur at m/z values that overlap with the ion cluster corresponding to the abundant (M+2H)+2 species. The other two c- and z-type fragment ions are not produced because their formation involves cleavage of the N—CH bond in the ring system of Pro. When this bond is broken, the new fragments remain attached through the other atoms in the ring. Accordingly, formation of c- and z-type product ions containing the N and C termini of Pro, respectively, are not observed in either ECD or ETD spectra.

Figure 7A:
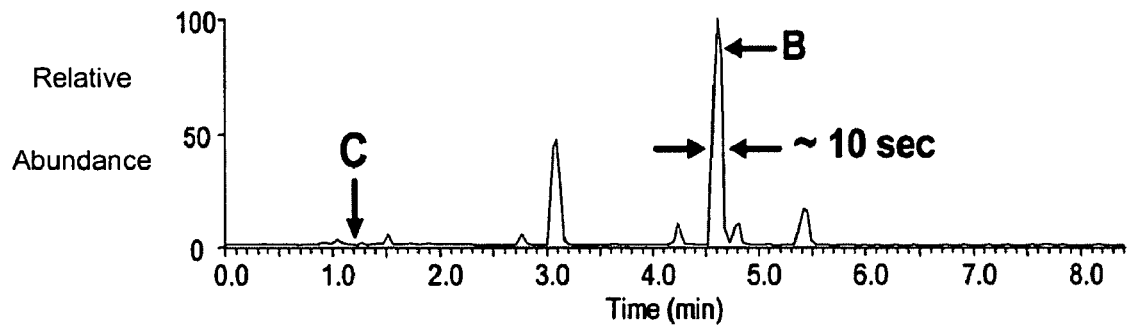
FIGS. 7A-7C represents data-dependent analysis of a peptide mixture by using a combination of nHPLC-µESI and ETD-MS/MS.
Figure 7B:
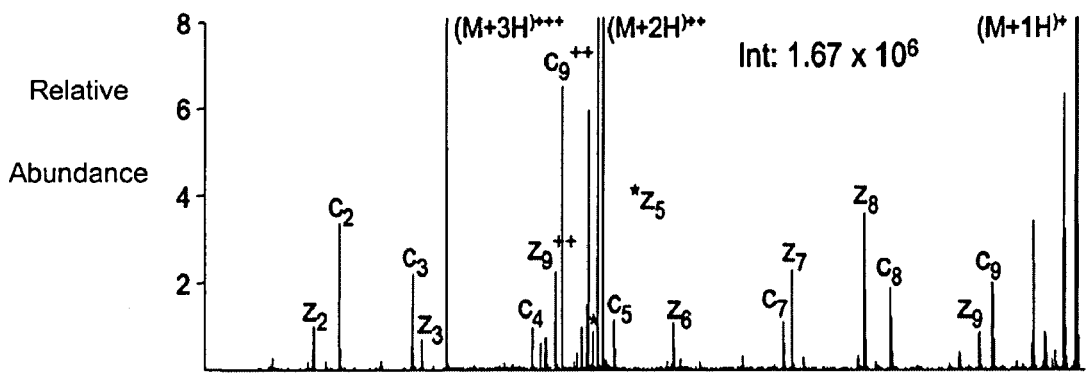
Figure 7C:
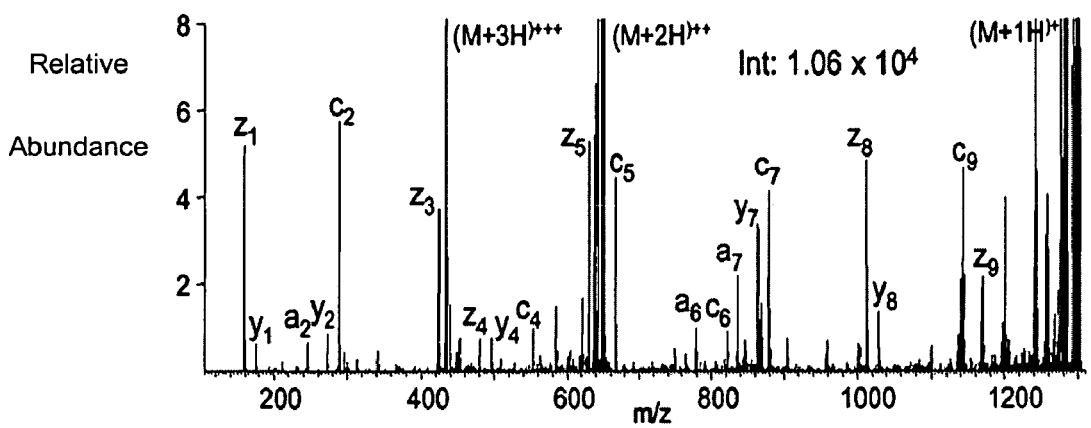

To demonstrate the feasibility of generating ETD spectra on a chromatographic time scale, we analyzed a mixture containing 10 synthetic peptides at the 1- to 100-fmol level by nHPLC-μESI-MS/MS. Shown in FIG. 7A is an ion chromatogram containing signals corresponding to (M+3H)+3 ions at m/z 433, 524, and 434 for DRVYIHPFHL (SEQ ID NO: 2; 100 fmol), APVAPR-PAApTPNLSK (SEQ ID NO: 3; 10 fmol), and DRpSPIRGpSPR (SEQ ID NO: 4; 1 fmol), respectively. Peak widths are in the range of 10-14 sec. With the instrument operating in the data-dependent mode, multiple single-scan ETD spectra (in this case 500-600 msec per spectrum) were recorded for each sample. Single-scan ETD spectra for two of the peptides, DRVYIHPFHL (SEQ ID NO: 2) and DRpSPIR-GpSPR (SEQ ID NO: 4), are shown in FIGS. 7B and 7C, respectively. For angiotensin, DRVYIHPFHL (SEQ ID NO: 2), 14 of 18 possible c- and z-type product ions are present in the ETD spectrum (FIG. 7B). Those that are absent either occur at very low m/z values or cannot be observed because they are formed by cleavage of the Pro ring system. The single-scan ETD spectrum recorded on 1 fmol of the doubly phosphorylated peptide, DRpSPIRGpSPR (SEQ ID NO: 4), is displayed in FIG. 7C. Even at this sample level the spectrum contains 12 of 18 possible c- and z-type fragment ions. Four of the six missing are involved in the cleavage of the five-membered ring systems of the two Pro residues. Both of the above peptides are easily sequenced from the observed fragment ions.

Figure 8A:
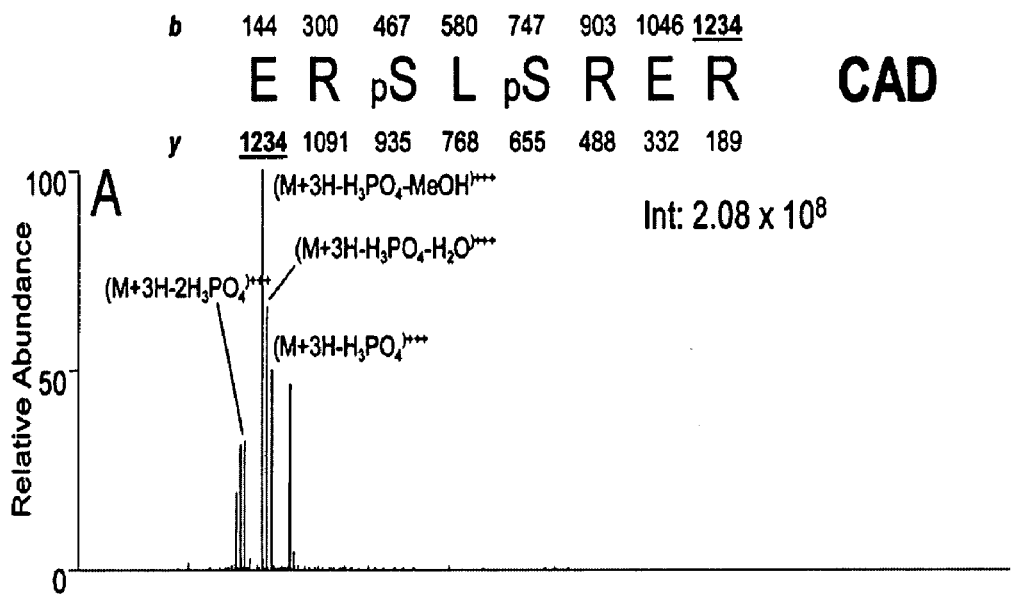
FIGS. 8A and 8B represents a comparison of single-scan (500- to 600-msec) CAD and ETD mass spectra recorded during data-dependent analyses (nHPLC-µESI-MS/MS) of phosphopeptides generated in a tryptic digest of human nuclear proteins. All peptides were converted to methyl esters and subjected to immobilized metal affinity chromatography before analysis by MS.
Figure 8B:
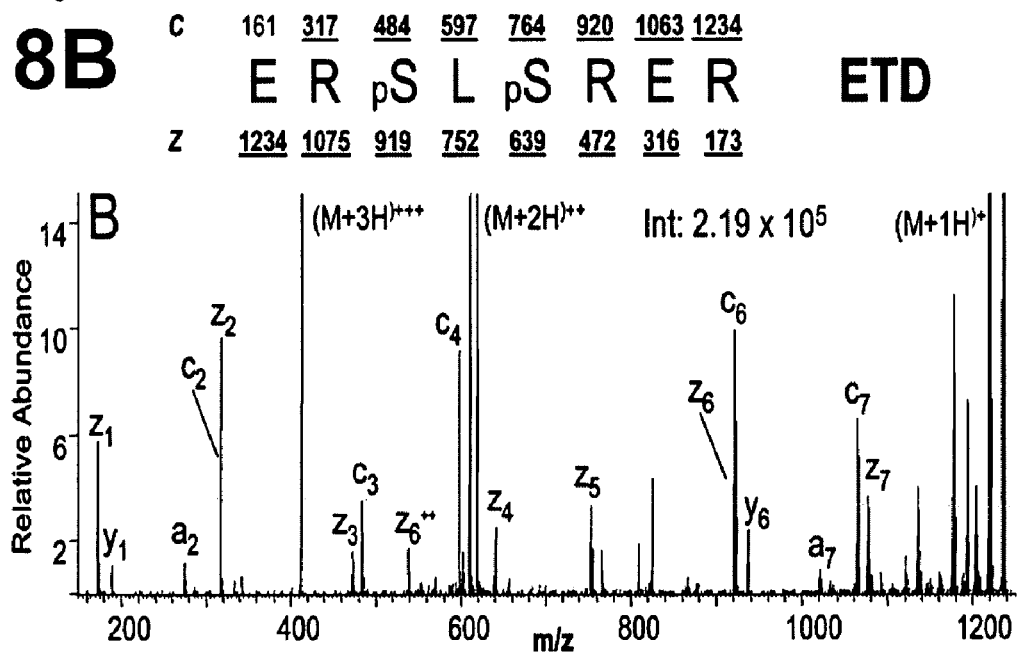

Displayed in FIG. 8 are the conventional CAD and ETD MS/MS spectra generated from (M+3H)+3 ions (m/z 412) of doubly phosphorylated peptide ERpSLpSRER (SEQ ID NO: 5). Both spectra were acquired during nHPLC analyses of phosphopeptides generated in a tryptic digest of human nuclear proteins. All peptides were converted to methyl esters and subjected to immobilized metal affinity chromatography before analysis by MS. Fragmentation observed in the low-energy CAD spectrum (FIG. 8A) is dominated by ions corresponding to the loss of one and two molecules of phosphoric acid from the side chains of Ser residues. Abundant ions, formed by the additional loss of water or methanol, are also observed. Fragment ions derived from cleavage of the peptide backbone are either absent or present at <2% relative ion abundance. Sequence analysis, therefore, is impossible.

The information content of the ETD spectrum (FIG. 8B) is dramatically different from that observed in the low-energy CAD spectrum. Ions produced by loss of phosphoric acid are absent, and fragmentation occurs predominately along the peptide backbone. Of 14 possible c- and z-type product ions, 13 are found in the spectrum. These are more than sufficient to define the sequence ERpSLpSRER (SEQ ID NO: 5).

Discussion

Both the quality and extent of fragmentation shown in FIGS. 6, 7, 8 and the sample level detected (FIG. 7C) are typical of that observed for spectra recorded to date on hundreds of peptides, including those with PTMs (data not shown). These spectra can be interpreted manually (de novo)

or used to search databases, with an algorithm such as SEQUEST, to generate peptide sequences (Eng et al., (1994) *J. Am. Soc. Mass Spectrom.* 5, 976-989). Typically, CAD tandem mass spectra of non-phosphorylated tryptic peptides generate crosscorrelation scores of 2.0-4.0. With ETD, tandem mass spectra of tryptic peptides with or without PTMs produce crosscorrelation scores ranging from 3.0 to 6.5. Further enhancement of these scores is likely once SEQUEST is adapted to consider features that are uniquely characteristic of ETD fragmentation (e.g., absence of c- and z-type fragments adjacent to Pro).

A by-product of this investigation is the development of an ion/ion instrument based on a radial ejection QLT mass spectrometer. Conventional QLT devices use dc potentials to provide axial ion containment. Consequently, only ions of a single polarity can be confined within any given region or segment of the trap, which precludes use of the commercial QLT for ion/ion experiments. In the modified QLT described herein, co-trapping of cations and anions is accomplished entirely by RF confinement fields. Secondary RF fields, imposed by superposition of RF voltages to the end lenses of the QLT, provided the required charge-sign-independent axial trapping.

The QLT instrument has several unique advantages over QIT instruments for performing ion/ion experiments, including greater ion capacity (30-fold) and higher ion-injection efficiency (10- to 30-fold) (39). As illustrated in FIGS. 5A-5H, manipulation of the dc bias potentials, applied to the QLT's segments and end lenses, permits axial segregation of precursor cations and reagent anions during anion injection and isolation. Initiation and termination of the ion/ion reaction is controlled by adjustment of these dc bias potentials. The physical geometry of the apparatus is also advantageous, because different types of ions may be injected from either end of the device by using two different ion sources: Furthermore, because anions are injected along the null axis of the RF quadrupole field, they suffer a minimal kinetic excitation. Anions injected in this manner are less likely to undergo electron detachment during stabilizing collisions with the helium buffer gas. "Soft" injection of anions was a key consideration in choosing a QLT for this work, because it was anticipated that the best anion electron donors might also be susceptible to premature electron detachment.

The commercial QLT instrument, modified for this research, was not engineered for experiments involving ion/ion reactions. Future linear trap instruments designed for this purpose will undoubtedly contain additional segments plus controls for superposition of multiple RF, ac, and dc fields. These features will allow implementation of even more extensive ion/ion manipulations, which almost certainly will include fully independent isolation of precursor and reagent ion clusters. Additionally, we envision implementing techniques that prevent ETD products from undergoing subsequent ion/ion reactions that lead to either neutralization of charge or formation of additional fragments.

Because the time scales for performing CAD, ETD, and proton transfer (charge reduction) in the QLT are short (tens of milliseconds), multiple ion-reaction steps can be incorporated into individual MS/MS or MS$^n$ experiments. In the context of "bottom-up" proteomics-type experiments (data-dependent HPLC MS/MS analyses of peptides generated by enzymatic digestion of protein mixtures), we expect ETD to promote the use of proteolytic enzymes such as Lys-C or Asp-N, which generate peptides having an average length of 20-25 residues. With ESI, such peptides are converted to precursor ions having three to six charges and thus are ideal candidates for ETD. Following ETD, we foresee use of an ion/ion, proton-abstraction reaction (charge reduction) to ensure that c- and z-type fragment ions are predominately in the +1 charge state before mass analysis.

Based on preliminary results, we believe that a protocol using MS$^3$ experiments could be ideal for generating sequence information from small proteins or large peptides. A typical MS$^3$ experiment might include the following steps: (i) gas-phase concentration (charge reduction by proton transfer with "ion parking") to convert the initial heterogeneous mixture of charge states observed for proteins ionized by ESI to a single charge state (precursor ion m/z); (ii) m/z isolation and CAD of the precursor ions to create a limited set of large product ions [either b-type ions produced by cleavage C-terminal to Asp residues or y-type ions formed by cleavage N-terminal to Pro residues]; (iii) m/z isolation and ETD of a single CAD product ion; and (iv) m/z analysis of the second-generation product ions. The resultant ETD MS$^3$ spectrum would yield sequence information derived from a single b- or y-type intermediate product ion (MS$^2$ product ion). A series of such MS$^3$ experiments would generate sequence information for all the major intermediate product ions.

In the protocol described above, the first dissociation step (CAD) is analogous to the enzymatic digestion step in the conventional bottom-up proteomics analyses. The MS$^3$ spectra correspond to the MS$^2$ spectra obtained from tryptic peptides. However, in the proposed MS$^3$ protocol, each MS$^3$ spectrum of a b- or y-type product ion provides sequence information for a portion of a protein for which the molecular mass is known.

EXAMPLE 3

Phosphoproteome Analysis with Electron Transfer Dissociation Mass Spectrometry

Phosphorylation forms the foundation of intracellular signaling networks, yet large-scale analysis of protein phosphorylation remains challenging because it occurs at low levels and phosphorylated peptides are difficult to sequence using conventional collision-activated dissociation (CAD) MS/MS. Described herein is a protocol that uses: (1) Lys-C to generate a mixture of large (~15-30 residues), multiply charged peptides, (2) immobilized metal affinity chromatography (IMAC) for phosphopeptide enrichment, (3) electron transfer dissociation for phosphopeptide fragmentation (without loss of phosphate), and (4) a new software algorithm (OMSSA) to facilitate database searches. The utility of this approach is demonstrated for the analysis of a whole yeast lysate and for displaying differential expression (phosphoprofiling) of phosphoproteins in two different cell systems.

Methods

Proteins from *S. cerevisiae* were extracted with Trizol, digested with Lys-C or trypsin, and the resulting peptides were converted to methyl esters with methanolic-HCl. For differential display experiments peptides from two samples were converted to $d_0$- and $d_3$-methyl esters, respectively, and then mixed together prior to analysis. Next, phosphopeptides were enriched by IMAC and analyzed by nRP-HPLC-µESI-MS/MS on a modified Finnigan LTQ (adapted to accept an additional ion source for ion/ion reactions). The instrument was operated under data-dependent mode allowing acquisition of either ETD spectra or sequential CAD/ETD spectra. ETD spectra were generated by injection of phosphopeptide cations into the linear ion trap from the front followed by a brief reaction (~65 ms) with fluoranthene anions injected from the rear CI source.

Results

ETD promotes fragmentation of the peptide backbone to form c/z ion pairs and leaves posttranslational modifications intact. Database searching with ETD spectra is being optimized in our laboratory, particularly for phosphopeptides, by using a new probability-based program—open mass spectrometry search algorithm (OMSSA).

To date, using the IMAC enrichment strategy on a yeast whole cell lysate, nearly 1,000 phosphopeptides were identified with high confidence from a single 90 minute experiment followed by a 1 hour database search. This preliminary data is in good agreement with the results obtained from an earlier study on yeast where ~1000 phosphopeptides were observed (signature phosphate neutral loss upon CAD MS)) following collision activated dissociation, but only 216 peptides could be identified by SEQUEST and/or verified through manual interpretation.

EXAMPLE 4

Sequential Ion/Ion Reactions

As described above, certain anions act primarily as either ETD or PTR reagents. By exposing cations to anions from either category, these discrete reactions can be performed seperately and sucessively. For example, highly charged peptide precursor ions (e.g., z>4) can be dissociated using ETD-inducing anions followed by removal of those reagents and introduction of a second, PTR-inducing anion type. The duration of this second reaction can be adjusted so that charge-states of the product species are reduced in a controlled manner. That is, a +10 precursor peptide could be dissociated via ETD to yield fragments having charges ranging from +1-+9. Of course, m/z resolution of isotopic peaks of such highly charged products can be problematic; therefore, the second PTR reaction duration can be adjusted so that the ETD products are converted to primarily the +1 charge-state. The net effect is to convert ETD fragments, initially produced in a variety of charge states, to lower charge states and, thus, simplifying spectral interpretation.

Obviously, other sequences or sucessions of ETD and PTR have utility, either alone or in tandem, with other ion manipulation methods (e.g., activation or m/z selection). In some instances it may be advantageous to charge reduce cation precursors prior to ETD or other ion manipulation techniques.

Methods

A Finnigan LTQ linear ion trap mass spectrometer was adapted to accept a chemical ionization source mounted on the rear side of the device, opposing a factory nanospray source peptide ion production. Negative chemical ionization (methane buffer) was used to produce anions of fluoranthene, benzoic acid, and sulfur hexafluoride. Introduction of fluoranthene and benzoic acid was accomplished via a batch inlet consisting of a gas chromatograph oven and a heated transfer line. Sulfur hexafluoride was introduced through a leak valve directly into the source (it is a gas). For charge-sign-independent trapping the LTQ electronics were modified to allow superposition of a secondary RF trapping voltage to the end lenses of the QLT.

Results

Figure 9:
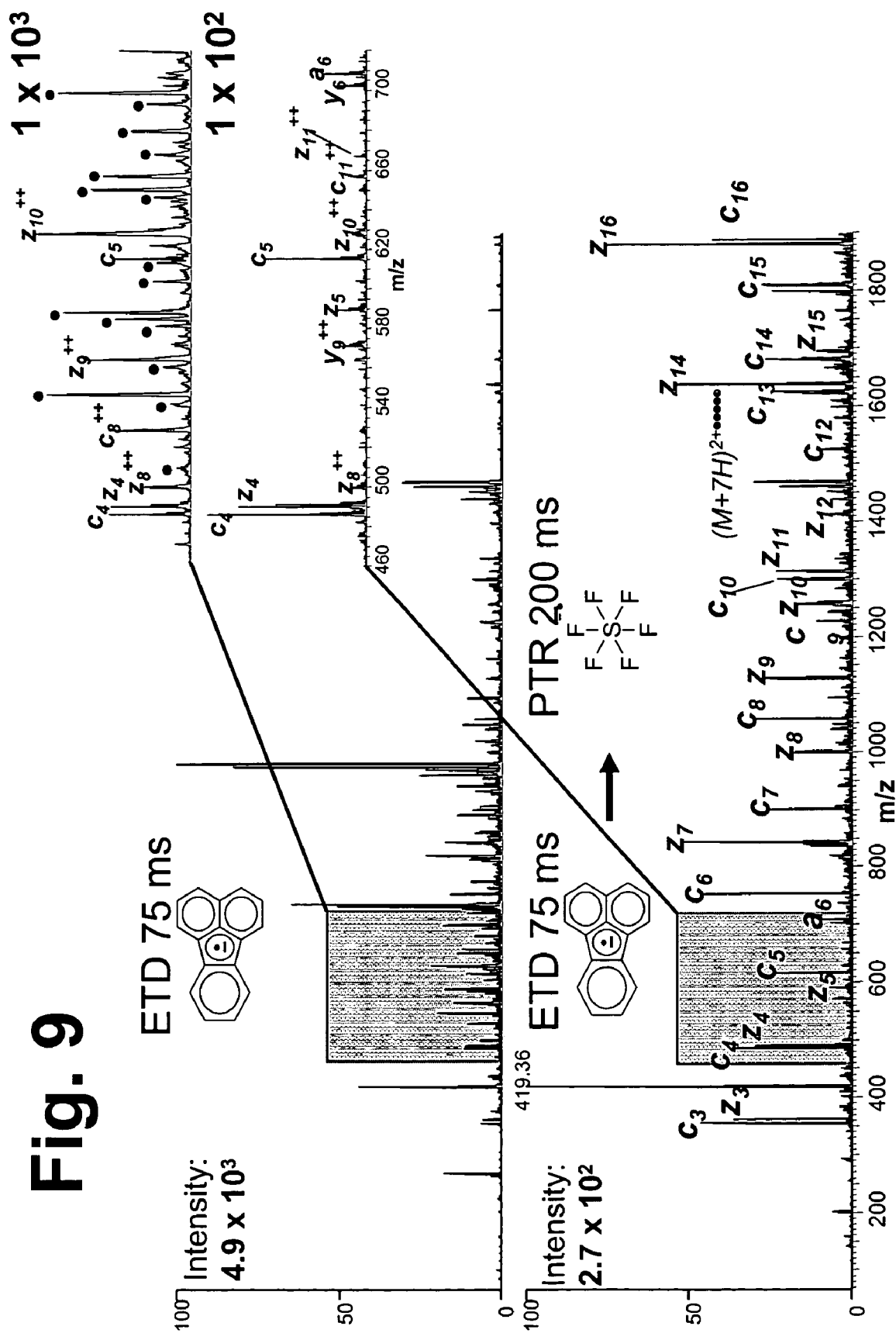
FIG. 9 shows a comparison of MS/MS spectra of the same +7 ACTH peptide (SYSMEHFRWGKPVGKKRRPVRVYP[7+]; SEQ ID NO: 72) (m/z 420) reacted with the anion of flouranthene for a duration of ~75 ms (FIG. 9, top panel), and reacted with the anion of flouranthene followed by reacting the resulting multiply charged product ions with even anions of sulfur hexafluoride for about 200 ms (FIG. 9, lower panel).

Using a modified linear ion trap mass spectrometer, we demonstrate direct interogation of highly charged peptides using sequential ion/ion reactions. Here the +7 ACTH peptide (SYSMEHFRWGKPVGKKRRPVRVYP$^{7+}$; SEQ ID NO: 72) (m/z 420) was first isolated and then reacted with the anion of flouranthene for a duration of ~75 ms (ETD). The spectrum produced following this reaction is shown in FIG. 9 (top panel). The peptide is dissociated at most all backbone bonds; however, many of the fragments have charges that are beyond the resolving power of the mass spectrometer used here (see inset, m/z's marked with a dot). To avoid this problem, we have implemented a sequential ion/ion reaction. In this experiment, following the ETD reaction, and the expulsion of excess flouranthene anions, the resulting multiply charged product ions are reacted with anions of sulfur hexafluoride (~200 ms). This second reaction (proton transfer, PTR) serves to simplify the product spectrum to contain only singly protonated fragment ions and to concentrate the various c and z-type product ion signals into one charge state. The net result is the production of a homologous series of singly charged c and z-type fragment ions characteristic of the N and C-terminal sequence of the precursor peptide (the linear trap has a limited m/z range of 2000). Note elimination of the multiply charged fragments denoted in the upper inset.

Figure 10:
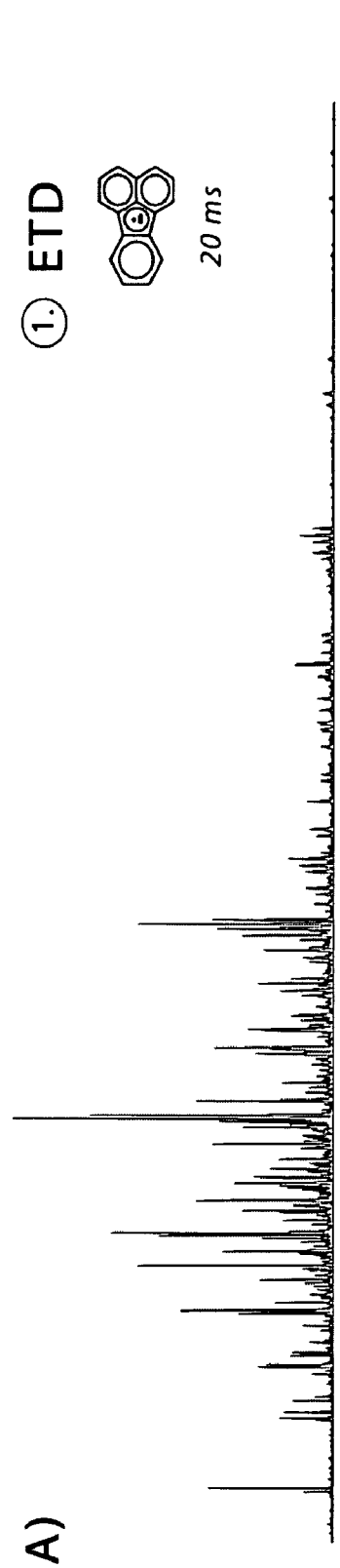
FIGS. 10A and 10B shows a comparison of MS/MS spectra of a +7 ACTH peptide (SYSMEHFRWGKPVGKKRRPVRVYP[7+]; SEQ ID NO: 72) (m/z 420) reacted with the anion of flouranthene for a duration of about 20 ms (FIG. 10A), and reacted with the anion of flouranthene followed by reacting the resulting multiply charged product ions with even anions of benzoic acid for about 150 ms (FIG. 10B).
Figure 10:
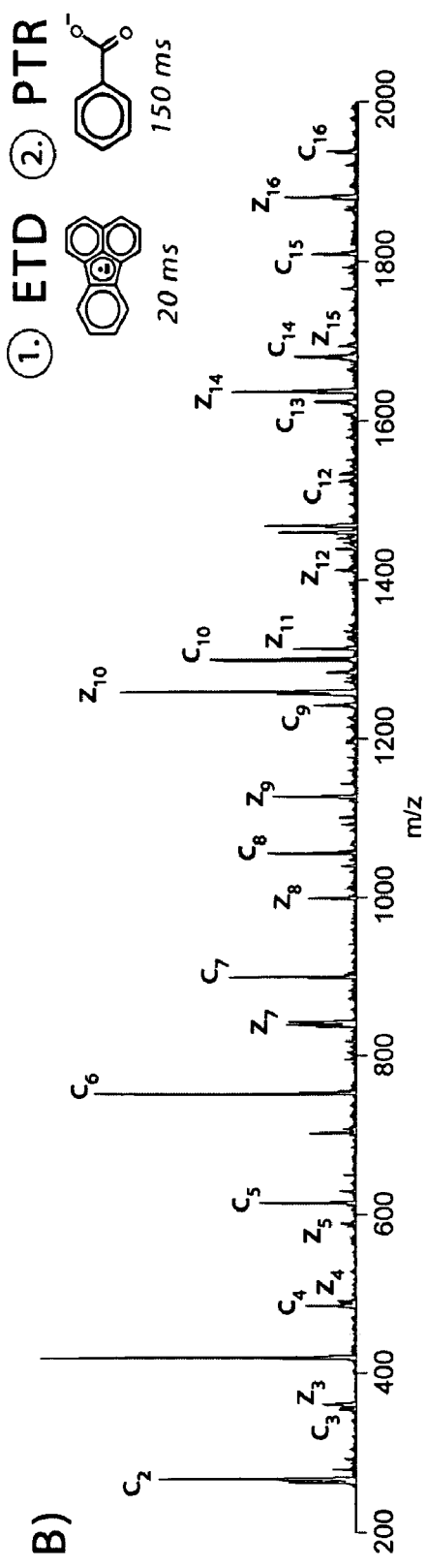

In FIGS. 10A and 10B, we have performed the same experiment, only this time utilizing benzoic acid as the PTR anion rather than sulfur hexafluoride. Note we have also reduced the duration of the intial ETD reaction. Again, the multiply charged fragment ions generated following the ETD experiment are charge reduced and concentrated to predominately the +1 charge state after the second PTR reaction. As the reaction period is extended, the higher-charged fragments are preferentially concentrated to lower charge states—predominately singly charged products in the case of the 150 ms reaction with benzoic acid (FIG. 10B). Obviously higher mass c and z-type fragment ions are produced following the ETD reaction, unfortunately the simplifying proton transfer reaction increases their m/z values beyond the instruments M/z range. Coverage can be extended by choosing a PTR reaction time to yield mostly doubly and singly charged fragment ions, which are compatible the upper limit of the instrument's m/z resolving power. The PTR reaction duration can be adjusted to produce product charge-states commensurate with the mass analyzer m/z resolving power. Alternatively, hybridization of this ion/ion device with other mass anzlyers will also extend this mass range limitation (e.g., TOF, ICR, orbitrap, etc.).

EXAMPLE 5

LTQ-ETD Instrument Modification, Conditions, and Operation

All experiments were performed with a commercial Finnigan LTQ mass spectrometer (Thermo Electron, San Jose, Calif.) equipped with a modified nanoflow electrospray ionization (ESI) source (see FIG. 2). The LTQ was modified to accommodate a Finnigan 4500 CI source (Thermo Electron) placed at the rear of the instrument. The anion beam was gated by on/off control of the RF voltages applied to the octopole ion guides, which transport the anions from the CI source to the QLT. To generate and analyze the products of ion/ion reactions, instrument control software (ITCL code) was modified to incorporate the desired scan events.

Synthetic Phosphopeptide Preparation

Phosphopeptide standards were selected from a variety of on-going, in-lab projects based on presence of the characteristic phosphoric acid loss upon collisional activation: RLPIFNRIPSVSE (SEQ ID NO: 6), pSRpSFDYNYR (SEQ ID NO: 7), RpSpSGLpSRHR (SEQ ID NO: 8), RSMpSLLGYR (SEQ ID NO: 9), GpSPHYFSPFRPY (SEQ ID NO: 10), DRpSPIRGpSPR (SEQ ID NO: 11), LPISASHpSpSKTR (SEQ ID NO: 1), RRpSPpSPYYSR (SEQ ID NO: 12), SRVpSVpSPGR (SEQ ID NO: 13), APVApSPRPAApTPNLSK (SEQ ID NO: 14) (where "p" precedes the site of phosphorylation). Synthesis was performed using standard Fmoc solid-phase chemistry (AMS 422 multiple peptide synthesizer, Gilson, Middleton, Wis.).

Human Nuclear Protein Purification and Digestion

HEK cells were grown to confluence in T-150 (150 $cm^2$) flasks and serum starved overnight. The cells were released with trypsin/EDTA, washed once in serum-free media, and split into two aliquots of 10 mL ($2\times10^6$ cells/mL). The first aliquot was incubated with 10 μM forskolin in DMSO for 5 min at 37° C. The control cells were treated the same except with 10 μL of DMSO only (0.1% final). The resuspended cells were pelleted and lysed by douncing in hypotonic buffer containing: 10 mM HEPES, pH 7.9, 10 mM KCl, 1.5 mM $MgCl_2$, 2 mM EDTA, 2 mM EGTA, 2 mM $Na_3VO_4$, 2.1 mg/mL NaF, 1 nM okadaic acid, 0.5 mM PMSF, 0.5 mM AEBSF, 2 μg/mL leupeptin, 2 μg/mL pepstatin A, 2 μg/mL aprotinin, 20 μg/mL benzamidine. The nuclear pellet was isolated by low speed centrifugation and resuspended in TRIzol® reagent (Invitrogen/Gibco, Carlsbad, Calif.). RNA and DNA fractions were discarded. The protein pellet was washed in guanidine:HCl/ethanol and resuspended by sonciation in 1% SDS. The suspension is dialyzed overnight against 2 L of 1% SDS in a 3500 MW Slide-A-Lyzer® cassette (Pierce, Rockford, Ill.). Concentration of the protein was ~6 mg/mL as determined by BCA assay (19, 20). An aliquot corresponding to ~300 μg of total protein from the control was diluted to 0.1% SDS with 100 mM $NH_4HCO_3$ and heated at 100° C. for 10 min. Proteins were digested with trypsin (1:20) at 37° C. overnight. Peptides were acidified to pH 3.5 with acetic acid. Protein from forskolin-treated cells was not analyzed.

Analysis of Human Nuclear Phosphopeptides—ETD

The human nuclear peptides were converted to methyl esters by performing the reaction twice. Additionally, the peptides were reconstituted in equal parts acetonitrile, methanol, and 0.01% aqueous acetic acid, and IMAC elution was with 250 mM ascorbic acid (Sigma, St. Louis, Mo.) with a final 2 h reversed-phase separation (described above). Fluoranthene was introduced to the CI source through an improvised, heated batch inlet consisting of a gas chromatograph oven (set to 120° C.) and a heated transfer line assembly (Thermo Electron, San Jose, Calif.) connected to a fused silica restrictor column. Negative CI, with methane buffer gas (MG Industries, Malvern, Pa.), was used to produce negative ions of fluoranthene (Aldrich, St. Louis, Mo.). Spectra were recorded under data-dependent settings using a method created through ITCL for the direct comparison of CAD and ETD fragmentation methods. The instrument was instructed to perform a full MS scan followed by alternating CAD and ETD of the top five most abundant m/z values. The automatic gain control target was set to 20,000 for CAD and 50,000 for ETD. Anions were injected for 25 ms and then allowed to react with the peptides for 55 ms before ejecting product ions.

Automated Peptide Identification

For CAD SEQUEST (9) [v.27, rev. 9 (c) 1993] and TurboSEQUEST [v.27, rev. 11 (c) 1999-2002] was used throughout the course of these experiments. For ETD data, the algorithm was modified to score c and z ions: (TurboSEQUEST v.27 rev. 11, (c) 1999-2003 "Sequest27_a_mod"). Presented sequences were validated by manual interpretation of the corresponding spectra.

Results

Human Nuclear Phosphopeptide Analysis—ETD

Figure 11A:
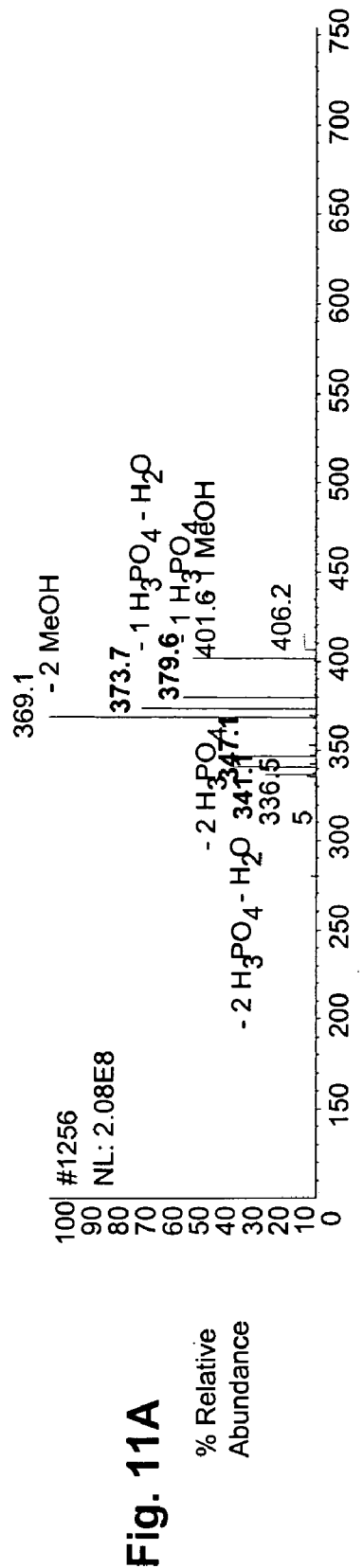
FIGS. 11A and 11B show a comparison of MS/MS spectra of the same human nuclear phospho-peptide ion with m/z 412.6 obtained utilizing a standard CAD procedure (FIG. 11A) with an MS/MS spectrum of the same phospho-peptide obtained utilizing ETD (FIG. 11B). The spectrum derived from the standard CAD protocol (FIG. 11A) provide enough structurally informative fragmentation information to identify the phosphopeptide. In contrast, MS/MS utilizing ETD (FIG. 11B) provides the nearly complete c and z ion series, enabling full structural identification of the precursor ion. Note, —OCH3 indicates C-terminal conversion to methyl ester, e indicates a glutamic acid methyl ester and NL means normalized intensity.
Figure 11B:
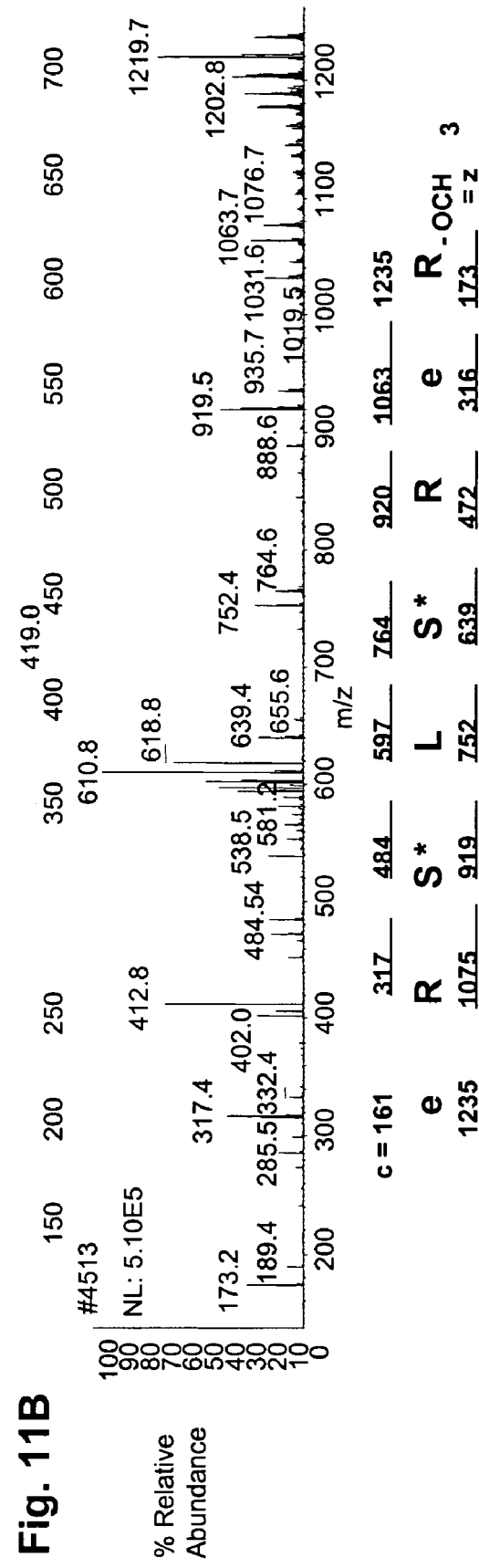

Our initial attempts to identify phosphopeptides from human nuclear extracts by CAD tandem MS resulted in the detection of several hundred phosphorylated peptides; however, inadequate peptide backbone fragmentation only allowed interpretation of approximately ten phosphopeptide sequences The most abundant phosphopeptide from the human nuclear extract was a doubly phosphorylated peptide (m/z 412.6) whose CAD spectrum was characterized by the neutral losses of phosphoric acid, water, and methanol (FIG. 11A). In a separate analysis, we utilized ETD tandem MS to analyze this same sample. The ETD spectrum acquired for this same peptide does not contain any of these neutral losses, but rather, reveals a complete c and z type ion series, enabling the identification of the phosphopeptide as eRpSLpSReR (SEQ. ID NO: 15) from the human nuclear splicing factor, arginine/serine-rich 3 protein. (FIG. 11B). Lower case "e" indicates methyl ester conversion of glutamic acid and "p" denotes a phosphorylated serine residue.

Figure 12A:
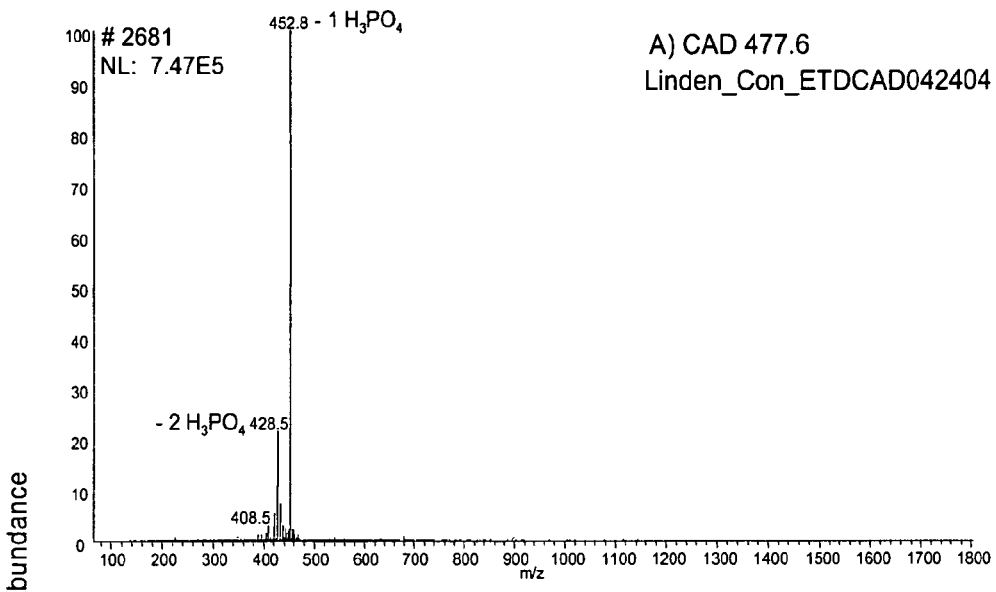
FIGS. 12A and 12B show a comparison of fragmentation patterns of a quadruply phosphorylated, human, nuclear peptide generated by CAD and ETD
Figure 12B:
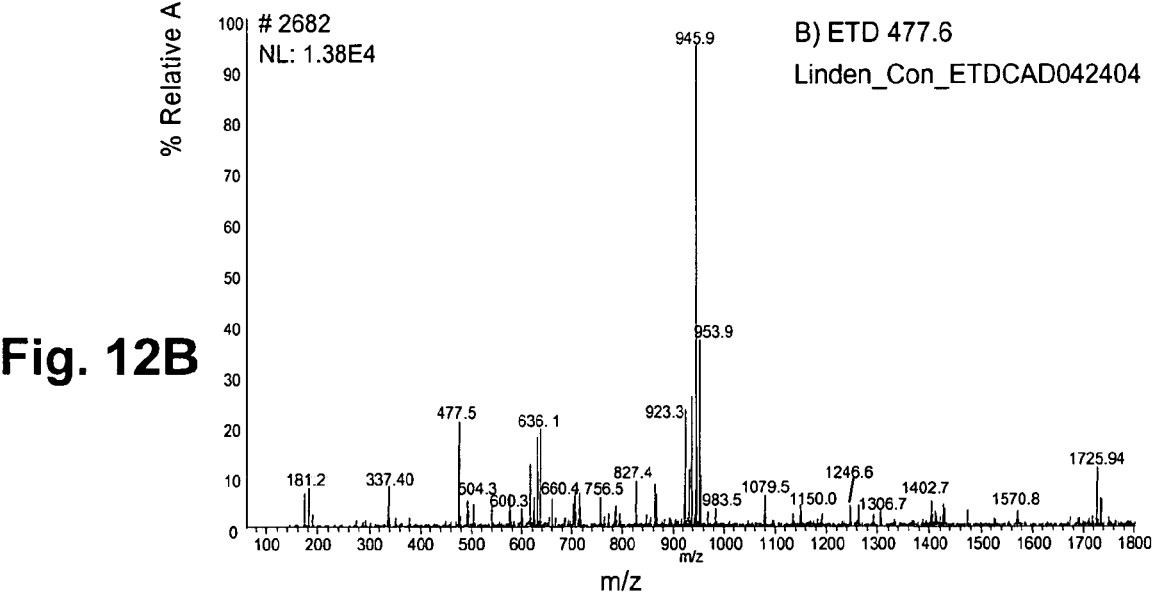

To provide a direct comparison of the two methods (CAD and ETD) we performed a third experiment that alternated CAD and ETD, consecutively, on the eluting phosphopeptides. This enabled the acquisition of the ETD spectrum immediately following the CAD spectrum to control for differences in peak intensity and experimental variation between separate samples. Similar CAD fragmentation patterns were again observed for m/z 412.6 (data not shown). Furthermore, FIG. 12A shows a CAD spectrum recorded from this experiment of a quadruply charged peptide with strong neutral losses (insufficient backbone fragmentation prohibited sequence analysis of this peptide). Interpretation of the corresponding ETD spectrum (subsequent scan) revealed it was a quadruply phosphorylated peptide (FIG. 12B). Every product ion with the exception of $z_3$ and $c_9$ were present. These ions are not detected because cleavage between the amide nitrogen and alpha carbon is never observed due to the ring system of the proline. These cleavages occur, though they are not detected due to the ring system of proline.

After reanalysis of the human nuclear phosphopeptides by ETD, over one-hundred phosphopeptides were identified. Table 2 is a partial list (over 50 new sequences) of these phosphopeptides sequences identified using ETD tandem MS and subsequent analysis with SEQUEST (a computer scoring algorithm). Manually verified peptides are checked.

TABLE 2

Human nuclear phosphopeptides detected with ETD
Analysis: Linden Con ETDCAD042604

| | Manually Confirmed | Protein name and peptides identified | Xcorr | Scan | Charge |
|---|---|---|---|---|---|
| 1 | | gi|7657864|AAF66079.1| | | | |
| | ✓ | RYRpSRpSRpSRpSPYRRI; SEQ ID NO: 16 | de novo | 2682 | 4 |
| 2 | | gi|9956070|gb|AAG02007.1| | | | |
| | | RSYpSPDGKEpSPSDKKS; SEQ ID NO: 17 | 4.16 | 4994 | 4 |
| | ✓ | RKRpSYpSPDGKE; SEQ ID NO: 18 | 2.77 | 2299 | 3 |
| 3 | | gi|4827040|ref|NP.005110.1| | | | |
| | | KTDSEKPFRGpSQpSPKRY; SEQ ID NO: 19 | 5.05 | 4326 | 4 |
| | ✓ | KSREpSVDpSRDpSpSHSRER; SEQ ID NO: 20 | 5.02 | 5107 | 4 |
| | | KSREpSVDpSRDpSpSHpSRERS; SEQ ID NO: 21 | 2.56 | 5349 | 4 |
| 4 | | gi|7706549|ref|NP.057591.1| | | | |
| | ✓ | RRRpSSpSPFLSKRS; SEQ ID NO: 22 | 4.78 | 4136 | 4 |
| | | RSGpSYpSGRpSPSPYGRR; SEQ ID NO: 23 | 3.41 | 5373 | 3 |
| | | RSGpSYpSGRSPpSPYGRR; SEQ ID NO: 24 | 3.38 | 5401 | 3 |
| 5 | | gi|9558733|ref|NP.037425.1| | | | |
| | ✓ | RpSRpSHpSPMSNRR; SEQ ID NO: 25 | 3.53 | 2753 | 3 |
| 6 | | gi|6002476|gb|AAF00003.1| | | | |
| | ✓ | RRpSRpSIpSLRRS; SEQ ID NO: 26 | 3.74 | 4194 | 3 |
| | ✓ | RpSRpSApSLRRS; SEQ ID NO:27 | 2.74 | 2126 | 3 |
| 7 | | gi|33356174|ref|NP.002678.2| | | | |
| | ✓ | RKRpSIpSESpSRpSRS; SEQ ID NO: 28 | 4.43 | 3527 | 3 |
| | ✓ | RSIpSESpSRSGKRS; SEQ ID NO: 29 | 3.19 | 2948 | 3 |
| 8 | | gi|29561827|emb|CAD87817.1| | | | |
| | ✓ | RRERpSLpSRDRN; SEQ ID NO: 30 | 3.06 | 2942 | 3 |
| | ✓ | RERpSLpSRDRN; SEQ ID NO: 31 | 2.91 | 3426 | 3 |
| 9 | | gi|21237808|ref|NP.620706.1| | | | |
| | ✓ | RKRpSPpSPSPTPEAKK; SEQ ID NO: 32 | 4.03 | 3382 | 3 |
| 10 | | gi|14603220|gb|AAH10074.1| | | | |
| | ✓ | RpSRpSRpSYERR; SEQ ID NO: 33 | 3.61 | 3424 | 3 |
| | | RRRpSPpSPAPPPRRR; SEQ ID NO: 34 | 3.69 | 2172 | 4 |
| | | KREpSPpSPAPKPRK; SEQ ID NO: 35 | 3.68 | 3281 | 3 |
| | | KRRpTApSPPPPPKRR; SEQ ID NO: 36 | 3.19 | 2836 | 4 |
| | | KRRpSPpSLSSKH; SEQ ID NO: 37 | 3.12 | 2042 | 3 |
| | + | RRRpTPpSPPPRR; SEQ ID NO: 38 | 3.07 | 3006 | 3 |
| | | RRRpSPSPPPpTRRR; SEQ ID NO: 39 | 2.97 | 2057 | 3 |
| | | RRPpSPRRRPpSPRRR; SEQ ID NO: 40 | 2.83 | 4411 | 4 |
| | | RSSApSLSGSSSSSSSRS; SEQ ID NO: 41 | 2.81 | 3547 | 3 |
| | | RRApSPSPPPKRR; SEQ ID NO: 42 | 2.49 | 2297 | 3 |
| | | RRVSHSPPPKQRSpSPVTKR; SEQ ID NO: 43 | 2.42 | 5151 | 3 |
| | | RRRpTPpTPPPRR; SEQ ID NO: 44 | 2.27 | 3116 | 3 |
| 15 | | gi|4759172|ref|NP.004710.1| | | | |
| | ✓ | RESRRpSEpSLpSPRRE; SEQ ID NO: 45 | 5.03 | 4356 | 4 |
| 16 | | gi|4506903|ref|NP.003760.1| | | | |
| | | RSRpSGpSRGRDpSPYQSRG; SEQ ID NO: 46 | 5.26 | 2588 | 4 |
| | | RpSRpSGSRGRDpSPYQSRG; SEQ ID NO: 47 | 4.90 | 3307 | 4 |
| 17 | | gi|4506901|ref|NP.003008.1| | | | |
| | | RRERpSLpSRERN; SEQ ID NO: 48 | 4.21 | 3833 | 4 |
| | ✓ | RERpSLpSRERN; SEQ ID NO: 49 | 3.84 | 4678 | 3 |
| | | RNHKpSpSRpSFpSRpSRS; SEQ ID NO: 50 | 2.73 | 2665 | 4 |
| 18 | | gi|26252134|gb|AAH40436.1| | | | |
| | ✓ | KRKLpSRpSPpSPSPRR; SEQ ID NO: 51 | 3.75 | 2381 | 3 |
| | | RKLpSRpSPpSPSPRR; SEQ ID NO: 52 | 3.64 | 2838 | 3 |
| | | RRpSRSApSRERR; SEQ ID NO: 53 | 2.42 | 3848 | 4 |
| | | RRSRSGTRpSPKK; SEQ ID NO: 54 | 2.07 | 2233 | 3 |
| 19 | | gi|23271009|gb|AAH34969.1| | | | |
| | ✓ | RGKKpSRpSPVDLRG; SEQ ID NO: 55 | 4.90 | 3285 | 3 |
| | | KRRpSLpSPKPRD; SEQ ID NO:56 | 3.33 | 2104 | 3 |
| 20 | | gi|21758154|dbj|BAC05256.1| | | | |
| | ✓ | RRRpSPpSPSPYYSRG; SEQ ID NO: 57 | 4.58 | 3743 | 3 |
| | | RRHpSHpSHpSPMSTRR; SEQ ID NO: 58 | 4.25 | 1756 | 3 |
| | | RpSRpSYpSRDYRR; SEQ ID NO: 59 | 2.77 | 5305 | 3 |
| 21 | | gi|20127499|ref|NP.006266.2| | | | |
| | ✓ | KARpSVpSPPPKRA; SEQ ID NO: 60 | 3.21 | 2412 | 3 |
| | | RSYpSGpSRpSRpSRS; SEQ ID NO: 61 | 2.44 | 2350 | 3 |
| 22 | | gi|1773227|gb|AAB48101.1| | | | |
| | | KRKpSLpSDSESDDSKSKK; SEQ ID NO: 62 | 6.00 | 4554 | 4 |
| | ✓ | KRKpSLpSDSESDDSKS; SEQ ID NO: 63 | 5.58 | 5582 | 3 |

TABLE 2-continued

Human nuclear phosphopeptides detected with ETD
Analysis: Linden_Con_ETDCAD042604

| | Manually Confirmed | Protein name and peptides identified | Xcorr | Scan | Charge |
|---|---|---|---|---|---|
| 23 | | gi\|16265859\|gb\|AAL16666.1\| | | | |
| | ✓ | RRpSRpSHpSDNDRFKH; SEQ ID NO: 64 | 6.37 | 3952 | 4 |
| | | RRpSRpSHSDNDRFKH; SEQ ID NO: 65 | 4.87 | 3217 | 4 |
| | | RpSRpSHpSDNDRFKH; SEQ ID NO: 66 | 2.74 | 5021 | 3 |
| 24 | | gi\|602021\|emb\|CAA29961.1\| | | | |
| | ✓ | RpSRpSRDKEERR; SEQ ID NO: 67 | 3.62 | 2269 | 3 |

+ found after removal of charge reduced parents from the DTA file
1. gi|7657864|gb|AAF66079.1| match to nuclear protein, NP220
2. gi|9956070|gb|AAG02007.1| similar to Homo sapiens mRNA for KIAA0723 protein
3. gi|4827040|ref|NP_005110.1| thyroid hormone receptor associated protein 3
4. gi|7706549|ref|NP_057591.1| CDC2-related protein kinese 7
5. gi|9558733|ref|NP_037425.1| transformer-2 alpha; htra-2 alpha; putative MAPK activating protein PM24
6. gi|6002476|gb|AAF00003.1| heat-shock suppressed protein 1
7. gi|33356174|ref|NP_002678.2| pinin, desmosome associated protein
8. gi|29561827|emb|CAD87817.1| SI:zC263A23.9.1 (novel protein similar to human splicing factor, arginine/serine-rich 3
9. gi|21237808|ref|NP_620706.1| SWI/SNF-related matrix-associated actin-dependent regulator of chromatin c2 isoform b
10. gi|4603220|gb|AAH10074.1| FUSIP1 protein
11. gi|6649242|gb|AAF21439.1| AF201422_1 splicing coactivator subunit SRm300
12. gi|5902076|ref|NP_008855.1| splicing factor, arginine/serine-rich 1
13. gi|5821151|dbj|BAA83717.1| RNA binding protein
14. gi|42542379|ref|NP_005830.2| serine/arginine repetitive matrix 1
15. gi|4759172|ref|NP_004710.1| splicing factor, arginine/serine-rich 2
16. gi|4506903|ref|NP_003760.1| splicing factor, arginine/serine-rich 9
17. gi|4506901|ref|NP_003008.1| splicing factor, arginine/serine-rich 3
18. gi|26252134|gb|AAH40436.1| Splicing factor p54
19. gi|23271009|gb|AAH34969.1| Serine/threonine-protein kinase PRP4K
20. gi|21758154|dbj|BAC05256.1| unnamed protein product
21. gi|20127499|ref|NP_006266.2| arginine/serine-rich splicing factor 6
22. gi|1773227|gb|AAB48101.1| HP1Hs-gamma
23. gi|16265859|gb|AAL16666.1|AF419332_1 TLS-associated protein TASR-2
24. gi|602021|emb|CAA29961.1| unnamed protein product
A4-2. Names of confirmed human nuclear phosphoproteins detected with ETD

EXAMPLE 6

Use of Aromatic Hydrocarbon Anions to Promote Electron Transfer Dissociation Anions that promote electron transfer dissociation have been investigated. Many of these anions belong to a class of compounds referred to as aromatic hydrocarbons. Our results demonstrate virtually all aromatic hydrocarbons tested have some ability to induce electron transfer dissociation when reacted with multiply charged peptides. The anions tested include napthalene, fluorene, phenanthrene, pyrene, fluoranthene, chrysene, triphenylene, perylene, acridine, 2,2' dipyridyl, 2,2' biquinoyline, 9' anthracenecarbonitrile, dibenzothiophene, 1, 10' phenanthroline, and anthraquinone. While all of these aromatic hydrocarbons promote electron transfer, both fluoranthene and 2,2' biquinoyline work particularly well.

Figure 13:
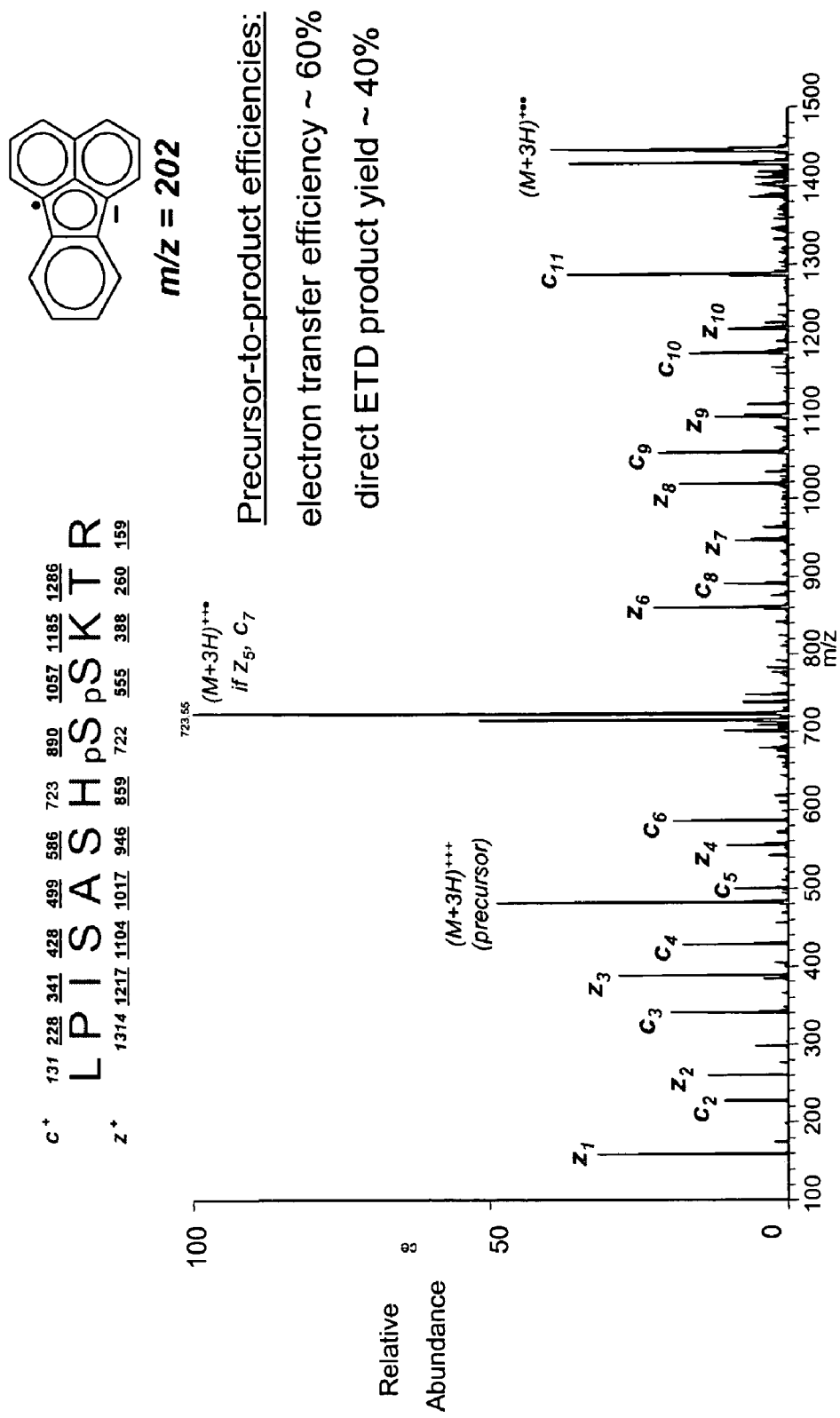
FIG. 13 represents a single-scan ETD-MS/MS spectrum resulting from the 50 ms reaction of m/z 202, from the radical anion of fluoranthene, with m/z 482 (triply protonated phosphopeptide, LPISASHpSpSKTR; SEQ ID NO: 1).

FIG. 13 represents a single-scan ETD-MS/MS spectrum resulting from the 50 ms reaction of m/z 202, from the radical anion of fluoranthene, with m/z 482 (triply protonated phosphopeptide, LPISASHpSpSKTR; SEQ ID NO: 1). Here only products of electron transfer are observed. Of the observed products, two-thirds correspond to products of direct electron transfer dissociation. And approximatley ⅓ of the products are the result of electron transfer without dissociation. These products can, however, be collisionally activated to generate products ions of type c and z (see section on low-energy activation). This indicates the initial electron tranfer event induces dissociation of the peptide backbone; however, the precursor peptide ion can remain intact through other non-covalent interactions. On the other hand, the low-energy activation could actually trigger or complete an ETD-like fragmentation pathway. In any event, the radical anion of fluoranthene induces electron transfer with high efficiency.

A plot of electron transfer dissociation efficiency vs. reaction q (q is a reduced parameter and affects ion motion, among other things, in the ion trap) was prepared. From this plot ~1300 counts (arbitrary units) are produced for products derived from electron transfer (q value~0.33). With no reaction the precursor intensity is ~3000 counts. We estimate with 100% electron transfer efficiency we would produce ~2000 counts (detector will produce ~⅔ the response for a +2 ion as compared to a +3). From this plot we estimate electron transfer efficiency to be 60%. Direct dissociation via electron transfer accounts for two-thirds of this value, or ~40%.

All of the aromatic hydrocarbons tested here induced electron transfer, with varying degrees of efficiency. Based on these results, we propose other aromatic hydrocarbons, not tested here, will behave similarly. Therefore, aromatic hydrocarbon compounds, in general, represent a preferred class of electron transfer inducing compounds when reacted with multiply charged cations. Further, modification of these compounds to include atom(s) of sulfur, oxygen, or nitrogen (heterocyclics) should not alter their electron transfer capability and are therefore are to be included in this group electron transfer promoting compounds. The table presents the compound, molecular weight, and the observed m/z of its corresponding anion(s). Other tested compounds include: acridine; 2,2' dipyridyl; 2,2' biquinoline; 9-anthracenecarbonitrile; dibenzothiophene; 1,10'-phenanthroline; 9' anthracenecarbonitrile; and anthraquinone. Anions derived from all of these compounds induced electron transfer dissociation to some extent.

EXAMPLE 7

Labile Post-Translational Modifications Identified with ETD Mass Spectrometry

Besides phosphorylation, many other protein post-translational modifications are CAD-labile and, therefore, difficult to sequence via CAD tandem MS. Here we provide examples of ETD tandem MS of the three most common and problematic modifications: phosphorylation, glycosylation, and sulfonation.

Figure 14A:
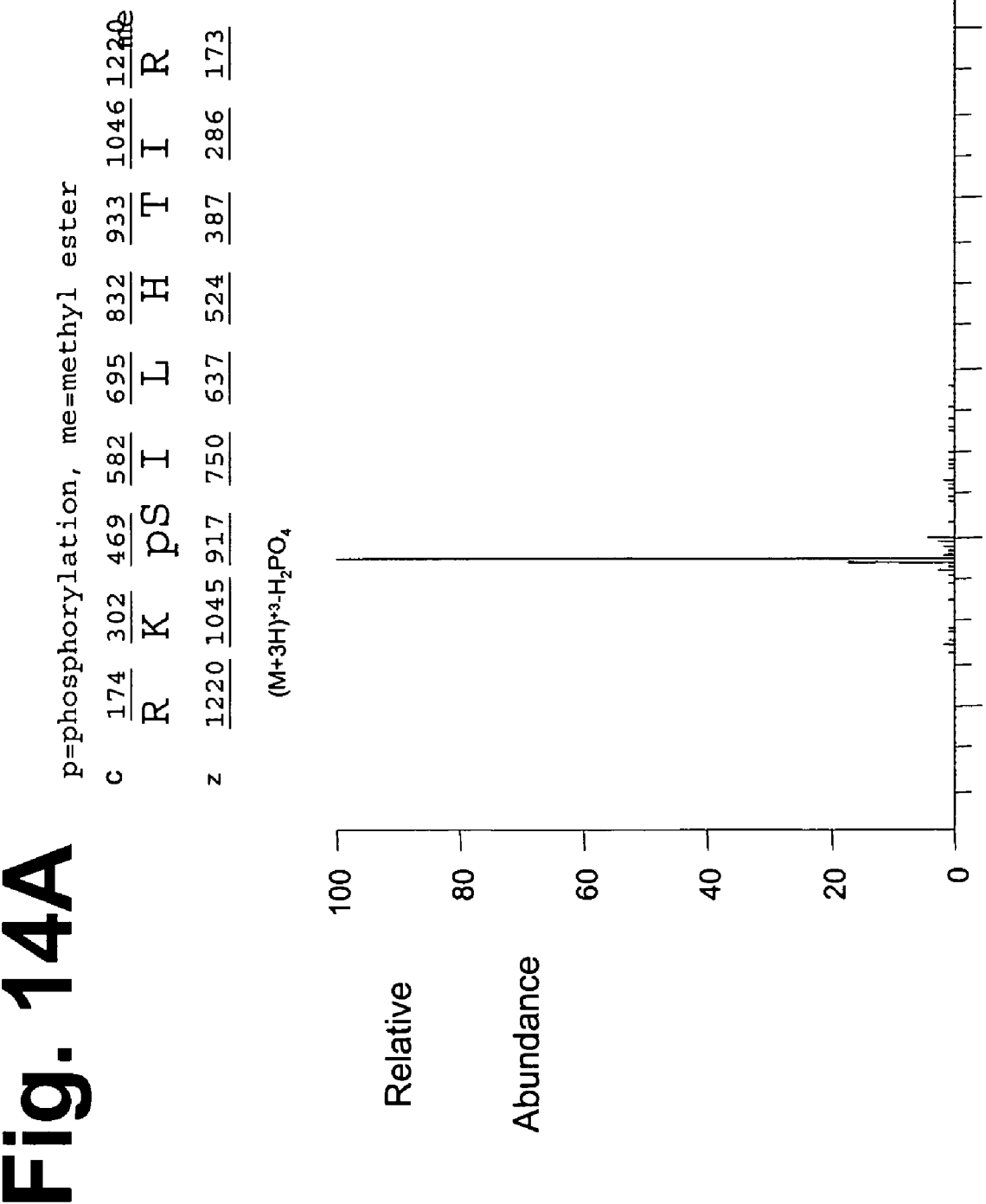
FIGS. 14A and 14B represent the spectrum resulting from analyzing the phosphorylated peptide, RKpSILHTIR (SEQ ID NO: 68) by CAD and ETD dissociation. The majority of the signal in the CAD spectrum (FIG. 14A) corresponds to the loss of phosphoric acid with little peptide backbone fragmentation. The ETD spectrum of the same peptide reveals peptide backbone cleavage generating a complete c and z ion series (FIG. 14B).
Figure 14B:
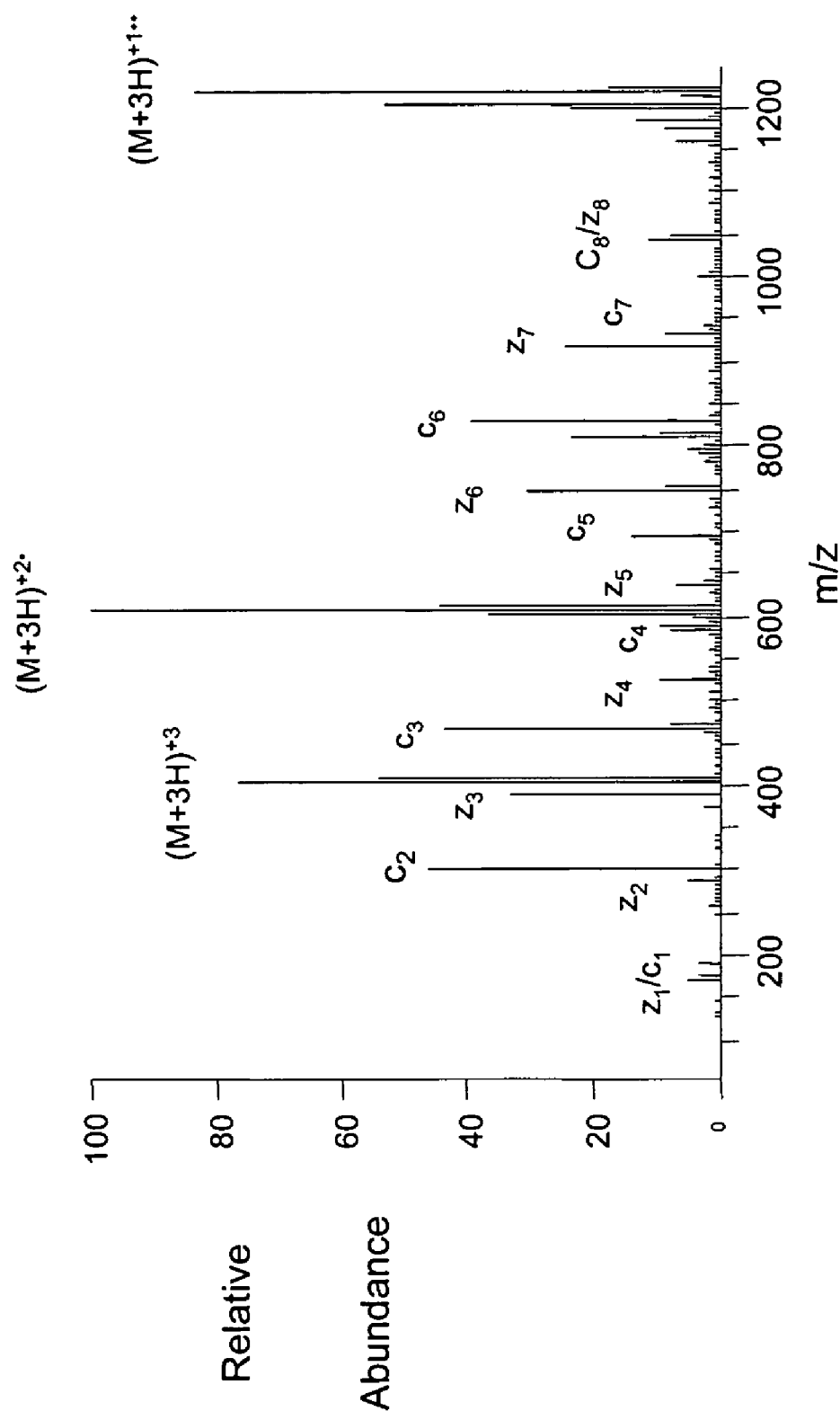

Phosphorylated peptides from a whole yeast lysate, digested with trypsin, were enriched by IMAC and as in example 5, were analyzed sequentially using CAD and ETD dissociation methods. An example of a typical phosphorylated peptide and it's fragmentation behavior under both methods is the triply protonated peptide observed at m/z 407. This phosphorylated peptide, RKpSILHTIR (SEQ ID NO: 68), displays a CAD tandem mass spectrum, wherein an ion corresponding to the neutral loss of $H_3PO_4$ is observed with little peptide backbone fragmentation (FIG. 14A). The low-level b and y ions, present at less than 5% of the total ion current in the CAD spectrum, are insufficient to define this peptide sequence. The ETD spectrum of the same peptide displays significant peptide backbone cleavage to generate a complete c and z type ion series and defines the sequence as RKpSILHTIR (FIG. 14B, wehrein pS indicates phosphoserine).

Figure 15A:
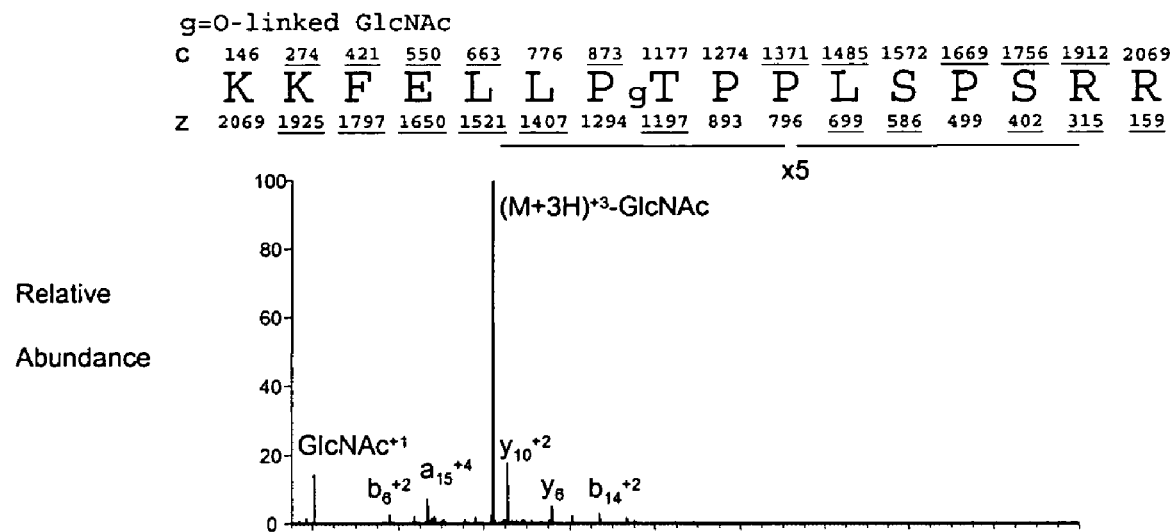
FIGS. 15A and 15B represent the spectrum resulting from analyzing the quadruply protonated peptide ion, KKFELLPgTPPLSPSRR (SEQ ID NO: 69) by CAD and ETD dissociation. The CAD spectrum from the O-GlcNAc modified peptide shows an ion at m/z 204 which corresponds to the O-GlcNAc oxonium ion and the corresponding $(M+3H)+3$ precursor ion with a neutral loss of 203 (GlcNAc) at m/z 623 (FIG. 15A). The rest of the CAD spectrum is composed of a few b, y and a type ions. In the ETD spectrum of KKFELLPgTPPLSPSRR (SEQ ID NO: 69), an almost complete c and z ion series for the peptide is observed (FIG. 15B).
Figure 15B:
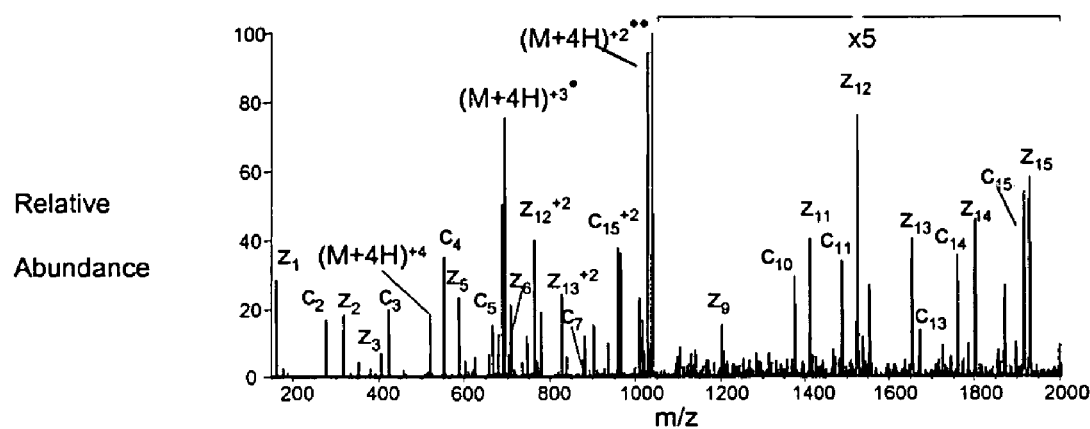

A glycosylated peptide (O-GlcNAc), KKFELLPgTPPL-SPSRR (SEQ ID NO: 69), the quadruply protonated molecule (m/z 518) was also dissociated by both CAD and ETD. The CAD spectrum is characterized by only a few fragment ions, one at m/z 204 which corresponds to the O-GlcNAc oxonium ion, and the corresponding $(M+3H)+^3$ precursor ion with loss of 203 (GlcNAc) at m/z 623 (FIG. 15A). The rest of the CAD spectrum is comprised of only a few b, y and a-type ions. The ETD spectrum, however, displays an almost complete c and z-type ion series for the peptide (FIG. 15B). The only c and z-type ions not observed are the forbidden cleavages involving the proline ring system.

Figure 16A:
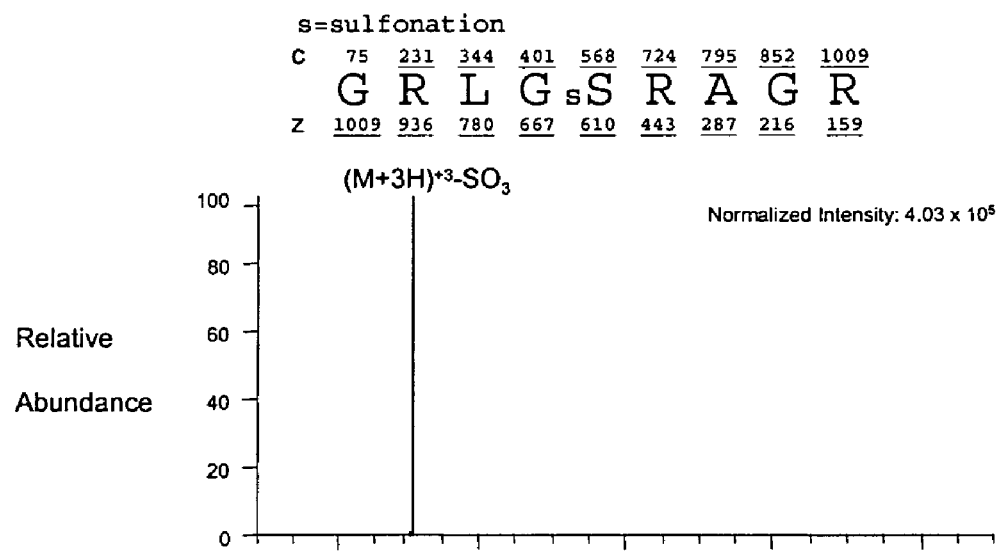
FIGS. 16A and 16B represent the spectrum resulting from analyzing the triply protonated peptide, GRLGsSRAGR (SEQ ID NO: 70), by CAD and ETD dissociation. Using CAD, the spectrum of the triply protonated ion at m/z 337 had one major ion at m/z 311 corresponding to the loss of $(SO_3)$ from the $(M+3H)+3$ precursor ion.
Figure 16B:
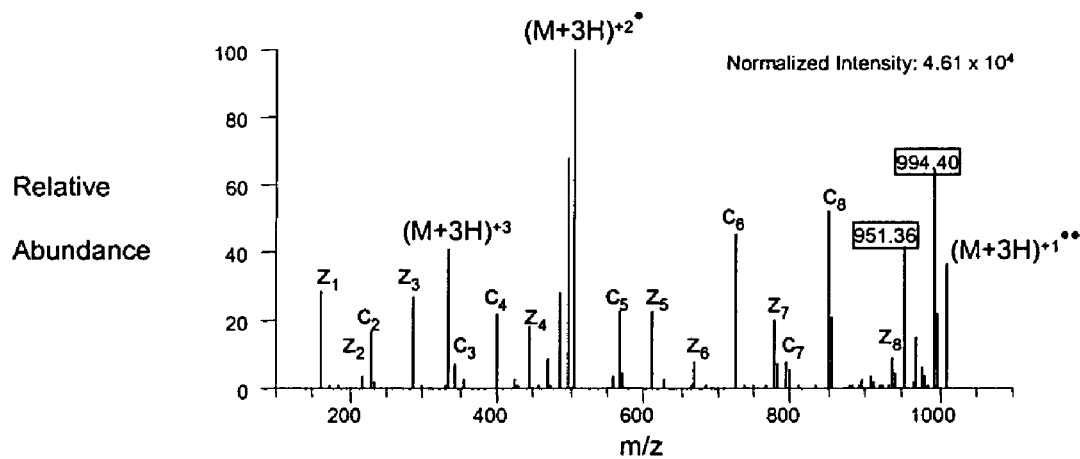

Sulfonation modification is the third type of CAD-labile PTM analyzed here by both ETD and CAD tandem MS. Here the sulfonated peptide, GRLGsSRAGR (SEQ ID NO 70), was fragmented using CAD and ETD mass spectrometry. Using CAD, the spectrum of the triply protonated ion at m/z 337 had one major ion at m/z 311 corresponding to the loss of $SO_3$ from the $(M+3H)^{+3}$ precursor ion. As seen in FIG. 16A, no other fragment ions are detectable. ETD tandem MS of this peptide generates a complete c and z-type ion series with no observable loss of $SO_3$ from the precursor ion (FIG. 16B).

Both phosphorylated peptides and sulfonated peptides have an addition of +80 Da to the parent mass ($PO_3$ and $SO_3$). Without accurate measurement, it can be difficult to identify a sulfonated peptide from a phosphorylated peptide by mass alone as the mass difference between these two PTMs is 0.0843 Da. However, sequential use of CAD and ETD can readily allow determination of both sequence (ETD) and identify the peptide as being phosphorylated vs. sulfonated (CAD). Using CAD, the loss of phosphoric acid is detected as a loss of −98 Da from the precursor mass of phosphorylated peptides while $SO_3$ displays a loss of −80 Da from the precursor ion mass. This will identify the peptide as a phosphorylated or sulfonated peptide. Then, the ETD spectrum can typically characterize the sequence of the peptide.

EXAMPLE 8

Negative Electron Transfer Dissociation of Peptide Anions

Figure 17:
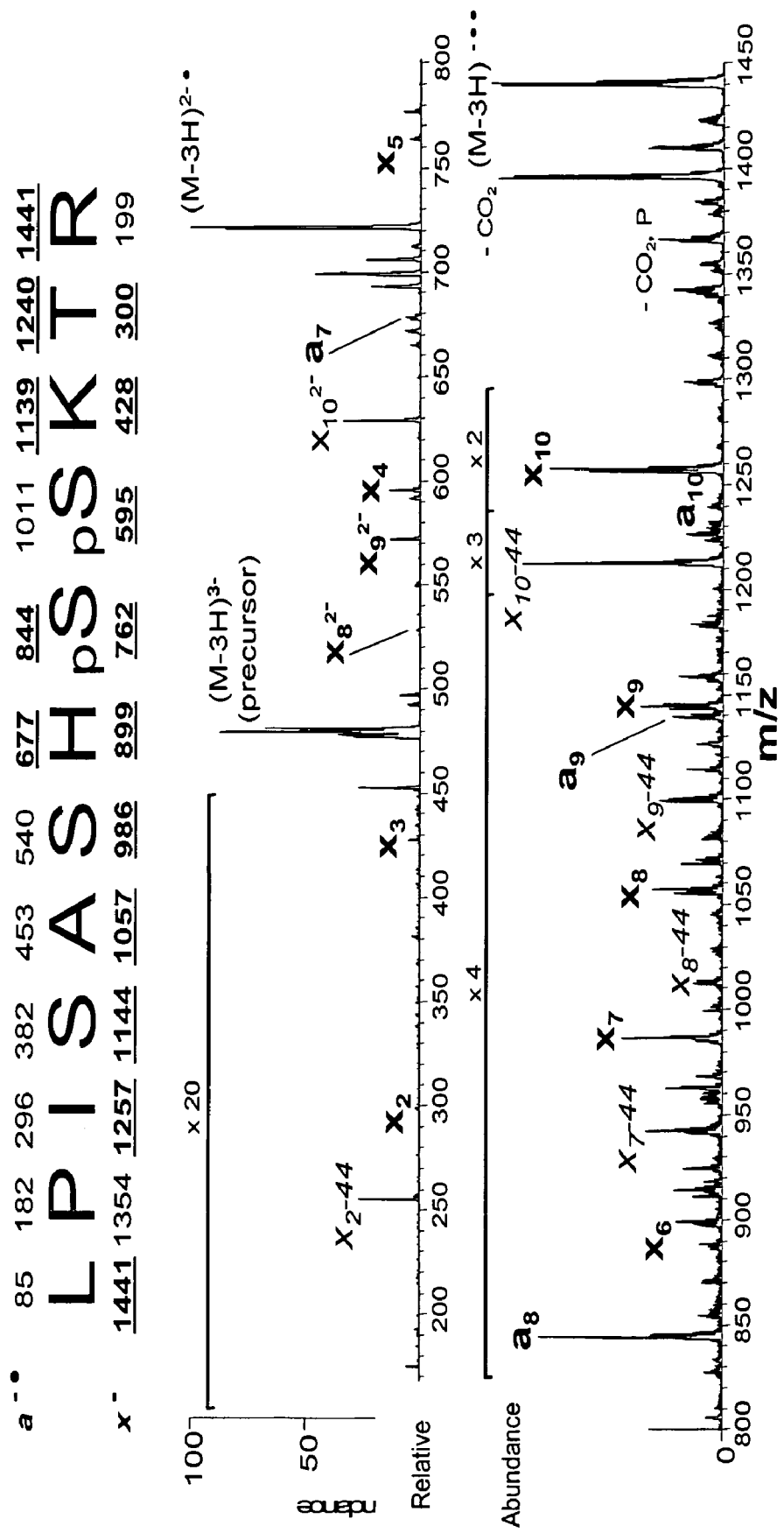
FIG. 17 represents a tandem mass spectra resulting from a 200 ms reaction of the triply deprotonated phosphopeptide, LPISASHpSpSKTR (SEQ ID NO: 1), with radical cations of Xe (average of 10 single-scan mass spectra).

One aspect of the present disclosure is directed to electron transfer reactions of multiply charged peptide cations with singly charged polynuclear aromatic anions to induce extensive peptide backbone fragmentation, electron transfer dissociation (NETD). However in accordance with one embodiment a modified quadrupole linear ion trap (QLT) mass spectrometer has also been used to examine the reactions of multiply deprotonated peptides with cations. The 200 ms reaction of the triply deprotonated phosphopeptide, LPISASHpSpSKTR (SEQ ID NO: 1), with radical cations of xenon generates extensive fragmentation with concomitant charge-reduction (FIG. 17). Of the dissociation products, a- and x-type fragment ions are most prevalent. Losses of carbon dioxide, phosphoric acid, and multiple combinations thereof are observed from both the charge-reduced precursor and the a- and x-type fragments.

Electron abstraction by $Xe^+$ generates a radical containing, charge-reduced peptide capable of dissociation driven by free-radical chemistry. For demonstration purposes, we follow the reaction of the triply deprotonated, three residue acidic peptide, EEA, with the Xe cation. The ion/ion reaction results in formation of a charge-reduced peptide that contains a radical site on the carboxyl group of the second residue. Abstraction of a hydrogen radical from backbone amide N facilitates cleavage of the adjacent C—C bond to produce a- and x-type product ions.

In addition to the a- and x-type products, we also note a series of ions having mass-to-charges 44 units lower than those contained in the x-type fragment series (FIG. 17). We suggest the x-44 ions arise from multiply deprotonated peptides that have lost at least two electrons to $Xe^+$. One electron removal likely occurs at the c-terminus, wherein free-radical-driven chemistry triggers neutral loss of $CO_2$, while another induces peptide backbone cleavage to generate an x-type fragment, which has previously lost its carboxy terminus ($x_n^-$-44, note these processes could occur in either order). If, for example, the $x_2^{2-}$ product ion of the triply deprotonated EEA peptide were to lose an electron through a subsequent reaction with Xe+, neutral loss of $CO_2$ could be triggered to generate an $x_2^-$-$CO_2$ product. Inspection of the tandem mass spectrum generated following reaction of the doubly deprotonated phosphopeptide with Xe cations (here the observed products could only result from a single electron transfer event) showed markedly reduced production of the $x_n^-$-$CO_2$- type product ions (two $x_n^-$-$CO_2$ products were observed at ~5% abundance relative to their respective x-type fragment, data not shown).

Our results are, to a certain extent, comparable with those achieved via EDD by Zubarev and co-workers for the doubly deprotonated caerulein peptide. For example, they also noted neutral losses of $CO_2$ from both the precursor and numerous fragments. Their experiment, however, produced a-, c-, and z-type fragment ions, while our ion/ion reaction predominately generated formation of a- and x-type fragments, with few or no c- and z-type fragments (from a limited set of other peptides, data not shown). It is conceivable that energetic electrons may be less selective in electron abstraction than the Xe cations used here. Any diversity in the initial location of the removed electron could allow EDD to access different reaction pathways than those achieved with negative electron transfer dissociation (NETD). Further characterization of both electron detachment approaches will be required to reveal these and other possible differences between the methods.

Use of Xe cations for electron abstraction precludes the proton transfer side reaction; note that proton transfer to peptide anions is highly exothermic. To study proton transfer reactions of peptide anions, we introduced another cation—protonated fluoranthene. The proton transfer reaction mainly reduced the charge of the peptide (eqn. 1), with only a small amount of fragmentation, $CO_2$

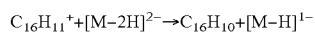

loss (~5% relative abundance, data not shown). Examination of the isotopic distribution of the charge-reduced peptide anion revealed electron transfer still occurred to a minor extent; the transfer presumably occurred from either fluoranthene or a low-level background cation. In either case, since the neutral loss product ion was 45 units less than the charge-reduced proton transfer product, we conclude the $CO_2$ loss was triggered by the electron transfer side reaction.

Wu and McLuckey described both electron and proton transfer reactions for olignonucleotide anions with fragmentation most prevalent following the former pathway (a result in agreement with our observations for peptide anions). Calculations prompted those authors to conclude that reaction exothermicity—not radical site introduction—was the major driving force for nucleotide anion fragmentation following ion/ion reaction. In another experiment Zubarev et al. reacted peptide anions with $H^+$ cations and observed neither $CO_2$ loss nor cleavage of the backbone, stimulating them to suggest that polypeptide anions are only facile when a radical site is present. At least for peptides, we find our results consistent with Zubarev's assertion that electron removal from peptide anions induces fragmentation driven by free-radical chemistry. In short, introduction of free-radical sites to multiply charged peptides allows access to new fragmentation pathways that are otherwise too costly (e.g., lowers activation energies). Ion/ion chemistry, namely electron transfer reactions, presents a rapid and efficient means of generating odd-electron multiply charged peptides. These reactions can be used for studying gas-phase chemistries and for peptide sequence analysis.

EXAMPLE 9

Triggering Electron Transfer Dissociation with Low-Energy, Off-Resonance Activation Following an electron transfer event there are two possible outcomes: (1) the electron-receiving peptide/protein can undergo direct cleavage to form two new species (a c and z-type product pair or with much lower probability a and y product pair), or (2) the peptide/protein ion can retain the additional electron but not undergo fragmentation. An example of this can be found in FIG. 18A where the doubly protonated peptide, RPKPQFFGLM (SEQ ID NO: 71), (m/z 674) was reacted with the radical anion of fluoranthene for 100 ms. After the reaction, several c-type ions are observed; these c-type fragments represent the first process described above (direct c/z-type fragment generation). In FIG. 18A, a substantial proportion of the observed electron transfer products are the charge-reduced intact precursor radical species, (M+2H)+..

This relative partitioning between direct fragmentation and charge-reduction, without dissociation, varies from peptide to peptide. In general we have observed the following trends: (1) For precursor ions of a given charge state, z, high m/z ratios tend to increase the yield of of non-dissociated radical products, and (2) for a given precursor m/z, lower precursor charge (z) also tends to correlate increased production of the non-dissociated product ions and higher charge states correlate to low yield of non-dissociated products. For example, for precursor ions of m/z having charge states of +2 or +3 would mostly like produce primarily the intact charge reduced radical product. Whereas precursors with the same m/z but with charge state of +10 or higher, would yield predominantly c, z, a, and y products ions with the intact charge reduced radical species being a small fraction of the total product ion yield. Note that regardless of m/z ratio or charge some production of charge-reduced, but non-dissociated species is almost always observed following an electron transfer event with all anions studied to date.

It has recently been reported that collsional-activation (CAD) of the intact radical charge-reduced peptide ion produced following electron transfer reactions can be accomplished in a three-dimensional ion trap device. In that work, CAD of the charge-reduced (M+2H)+. neurotensin peptide produced both c/z-type products (fragments characteristic of electron transfer dissociation) and b/y-type products (fragments characteristic of collisional-activation). Similar results have been observed by applicants following conventional collisional-activation of charge-reduced electron transfer products. For example, FIG. 18A shows a substantial yield of product ions corresponding to the (M+2H)+. of the peptide RPKPQFFGLM (SEQ ID NO: 71). Isolation of this charge reduced intact radical species (m/z 1348) followed by collisional activation (FIG. 18B), under typical Finnigan LTQ CAD conditions (q=0.25, normalized activation energy 35%, 30 ms duration), generates products characteristic of both ETD (c and z-type fragments) and collisional activation—m/z 1330 ($NH_3$ loss). Collisional activation of the corresponding non-radical intact, singly charged peptide (M+H)+, m/z 1347) generates the same dominant product ion at m/z 1330 (FIG. 18C). This result, which is in agreement with the observation of McLuckey and co-workers, demonstrates that collisional activation of charge-reduced electron transfer products results in the production of fragment ions characteristic of both ETD and CAD. From an analytical standpoint the possibility of generating products from two different processes is not desirable for several reasons. First, the product ion spectra will become more difficult to interpret since each fragment will require consideration as being c,z b, or y. Secondly, all the limitations associated with the collisional-activation process (described above) will still occur (neutral losses of labile PTMs, $H_2O$, $NH_3$, etc.).

To circumvent this problem the degree collisonal activation (dissociation) was significantly reduced through the use of an off-resonance excitation scheme to activate and dissociate these charge-reduced species. While this process still involves collisional activation, under appropriately weak collisional activation conditions the activation supplies sufficient energy to trigger an electron transfer-type dissociation pathway, but not enough energy to promote production of the conventional collision-activated dissociation products. The application of the weak collisional activation conditions can occur at any time during the ETD reaction or after termination of the ETD reaction. In accordance with one embodiment, after the step of mixing the anion with the positively multi-charged polypeptide the reaction is further supplied with sufficient energy to trigger an electron transfer-type dissociation pathway, but not enough energy to promote production of the conventional collision-activated dissociation products. More particularly, the polypeptide ion products are subjected to low-energy, off-resonance activation. In accordance with one embodiment, the ETD reaction is terminated and the remaining anions are expelled from the ion trap, while retaining the polypeptide ion product within the linear ion trap; and then the polypeptide ion products are subjected to low-energy, off-resonance activation.

FIG. 18D shows the low-energy, off resonance activation of the (M+2H)+. from the peptide RPKPQFFGLM (SEQ ID NO: 71) described above (MS/ETD/MS/CAD/MS). Here we activate the intact radical product at a lower q and with a lower resonant ampltiude (q=0.13, activation energy 17%, 60 ms duration) and apply this waveform slightly off-resonance of the target m/z. The off-resonance activation was accomplished by choosing 5 u wide isolation window of the intact radical product which also alters the range of m/z that is swept through a dipole resonance during the activation step. The larger window did not alter the number or type of ions that were m/z retained in the trap after the m/z isolation step; it did, however, increase the deviation between ion resonant frequencies and the frequency of the supplementary field at the beginning of resonance excitation RF sweep used to promote CAD. The Mathieu parameter q, is approximately proportional to an ions characteristic frequency in the RF trapping field and the maximum attainable kinetic energy it may attain whilst remaining in the field varies as the square of ion frequency and therefore q. Unlike the higher energy activation demonstrated in FIG. 18B, this activation converts the entire charge-reduced intact radical ion population to either c or z-type fragments—fragments that can only be derived from the electron transfer-type dissociation pathway. No fragmentation products associated with the conventional collision-activated dissociation pathway are observed. Further, activation (under these conditions) of the corresponding non-radical-containing, singly charged peptide (M+H)+ does not induce fragmentation of any type (FIG. 18E). We also note that some of the c-type fragments (c6 and c7), generated following this low-energy activation, are shifted to lower m/z by one unit compared to the same c-type ion generated following direct ET dissociation. We do not, as yet, have an explanation for this discrepancy. This low-energy, off-resonance activation can be considered a slow heating process that is apparently capable of triggering fragmentation exclusive to the electron transfer dissociation pathway.

The invention claimed is:

1. A method of mass spectrometry analysis based on electron transfer dissociation (ETD) of multiply charged organic and/or biomolecular cations, said method comprising the steps of introducing said multiply charged cations into an RF electric field ion containment device of a mass spectrometer;

introducing polyaromatic hydrocarbon anions as gas-phase electron transfer reagents into said ion containment device;

mixing the introduced polyaromatic hydrocarbon anions, or derivative anions thereof, and the multiply charged cations, or derivative multiply charged cations thereof, wherein said derivative anions and said derivative multiply charged cations are generated within said ion containment device during performance of said method, so as to facilitate electron transfer from the polyaromatic hydrocarbon anions, or said derivative anions thereof, to the multiply charged cations, or derivative multiply charged cations thereof, to induce cleavage of covalent bonds and produce fragment and/or dissociation product cations; and mass (m/z) analyzing and detecting said fragment and/or dissociation product cations or cations derived from said fragment and/or dissociation product cations for mass spectrometric analysis.

2. The method of claim 1 wherein the multiply charged cation is a polypeptide.

3. The method of claim 2 further comprising an additional activation step wherein sufficient energy in the form of photoactivation or collisional activation is supplied to the undissociated charge reduced electron transfer product cations so as to promote dissociation of said undissociated charge reduced electron transfer product cations via electron transfer-type dissociation pathway, with less than a 20% production of fragment cations characteristic of collisional-activation.

4. The method of claim 3 wherein said additional activation step is after the step of mixing said polyaromatic hydrocarbon anions or derivative anions with the positively multiply charged polypeptide cations.

5. The method of claim 2 further comprising an additional activation step wherein sufficient energy in the form of photoactivation or collisional activation is supplied to the undissociated charge reduced electron transfer product cations so as to promote dissociation of said undissociated charge reduced electron transfer product cations via electron transfer-type dissociation pathway, with less than a 5% production of fragment cations characteristic of collisional-activation.

6. The method of claim 5 wherein said additional activation step is after the step of mixing said polyaromatic hydrocarbon anions with the positively multiply charged polypeptide cations.

7. The method of claim 5 wherein said additional activation step is performed during the step of mixing the polyaromatic hydrocarbon anions with the positively multiply charged polypeptide cations.

8. The method of claim 7 wherein the activation energy is supplied in the form of collisional activation.

9. The method of claim 1 wherein the RF electric field ion containment device is an RF ion guide.

10. The method of claim 1 wherein the RF electric field ion containment device is an RF ion trap.

11. The method of claim 10 wherein the RF ion trap is a RF linear multipole ion trap.

12. The method of claim 11 where said polyaromatic hydrocarbon anions are injected along the linear axis of the RF linear multipole ion trap.

13. The method of claim 11 wherein the ion trap is a segmented linear RF multipole ion trap.

14. The method of claim 11 wherein the multiply charged polypeptide cations and the polyaromatic hydrocarbon anions are spatially segregated within the ion trap until said mixing step.

15. The method of claim 10 wherein the RF ion trap is a RF 3 dimensional multipole ion trap.

16. The method of claim 10 wherein the polyaromatic hydrocarbon anions and/or said derivative anions are radical anions.

17. The method of claim 10 further comprising the steps of expelling the remaining polyaromatic hydrocarbon anions from the RF ion trap, while retaining the electron transfer fragment and/or dissociation product cations within the RF ion trap; and
subjecting the electron transfer fragment and/or dissociation product cations to a low-energy, off-resonance kinetic excitation to effect collisional activation that produces less than 20% conventional collision-activated fragment and/or dissociation products.

18. The method of claim 10 further comprising the steps of expelling the remaining polyaromatic hydrocarbon anions from the RF ion trap, while retaining the electron transfer fragment and/or dissociation product cations within the RF ion trap; and
subjecting the electron transfer fragment and/or dissociation product cations to a low-energy, off-resonance kinetic excitation to effect collisional activation that produces less than 5% conventional collision-activated fragment and/or dissociation products.

19. The method of claim 1 wherein the kinetic energies of the introduced polyaromatic hydrocarbon anions, or said derivative anions thereof, and the multiply charged cations, or said derivative multiply charged cations thereof, are less than 1 electron volt, during the mixing step.

20. The method of claim 1 wherein said polyaromatic hydrocarbon anions and/or said derivative anions are radical anions.

21. The method of claim 1 wherein the polyaromatic hydrocarbon anions are generated from a low electron affinity substrate selected from the group consisting of anthracene, 9,10-diphenyl-anthracene, naphthalene, fluorene, phenanthrene, pyrene, fluoranthene, chrysene, triphenylene, perylene, acridine, 2,2'-dipyridyl, 2,2'-biquinoline, 9-anthracenecarbonitrile, dibenzothiophene, 1,10'-phenanthroline, 9'-anthracenecarbonitrile, and anthraquinone and substituted derivatives of said low electron affinity substrates.

22. The method of claim 1 wherein the multiply charged cations and the polyaromatic hydrocarbon anions are spatially segregated within the RF field ion containment device until said mixing step.

23. The method of claim 1 further comprising the steps of introducing anions of a second type into said ion containment device, wherein the second type anion will substantially exclusively abstract protons from cations; and mixing and reacting said second type of anions with said fragment and/or dissociation product cations.

24. The method of claim 23 wherein the second anion type is derived from a compound selected from the group consisting of a carboxylic acid, phenolic, and alkoxide containing compound.

25. The method of claim 24 wherein the second anion type is an anion of a compound selected from the group consisting of benzoic acid, perfluoro-1,3-dimethylcyclohexane, $SF_6$, and perfluorotributylamine.

26. The method of claim 1, wherein the mixing step includes simultaneously confining in a common region of the RF electric field containment device the polyaromatic hydrocarbon anions, or said derivative anions thereof, and the multiply charged cations, or derivative multiply charged cations thereof.

27. A method for analyzing the amino acid sequence of a polypeptide, said method comprising
introducing multiply charged polypeptide cations into an RF ion trap;
introducing polyaromatic hydrocarbon anions as gas-phase electron transfer reagents into an RF ion trap;
mixing said polyaromatic hydrocarbon anions and multiply charged polypeptide cations so as to facilitate electron transfer from the polyaromatic hydrocarbon anions to the multiply charged polypeptide cations, thus inducing cleavage of covalent bonds and the production of electron transfer fragment and/or dissociation product cations;
terminating the reactions by physically separating the remaining polyaromatic hydrocarbon anions from the electron transfer fragment and/or dissociation product cations;
conducting m/z analysis of cations remaining in the trap.

28. The method of claim 27 wherein the electron transfer fragment and/or dissociation product cations are m/z sequentially ejected from said RF ion trap to an ion detector.

29. The method of claim 28 wherein the ion trap is a linear RF multipole ion trap.

30. The method of claim 29 wherein the polyaromatic hydrocarbon anions are injected along the linear axis of the linear ion trap.

31. The method of claim 27 wherein the polyaromatic hydrocarbon anions are radical anions generated from a low electron affinity substrate selected from the group consisting of anthracene, 9,10-diphenyl-anthracene, naphthalene, fluorene, phenanthrene, pyrene, fluoranthene, chrysene, triphenylene, perylene, acridine, 2,2'-dipyridyl, 2,2' biquinoline, 9-anthracenecarbonitrile, dibenzothiophene, 1,10'-phenanthroline, 9'-anthracenecarbonitrile, and anthraquinone and substituted derivatives of said low electron affinity substrates.

32. The method of claim 27 wherein said polyaromatic hydrocarbon anions and/or said derivative anions are radical anions.

33. The method of claim 27, wherein the mixing step includes simultaneously confining in a common region of the RF ion trap the polyaromatic hydrocarbon anions and the multiply charged polypeptide cations.

34. A method for dissociating a polypeptide by negative electron transfer dissociation (NETD) for mass spectrometry analysis, said method comprising
introducing multiply charged polypeptide anions into an RF electric field ion containment device;
introducing gas-phase cations of an inert gas, into an RF electric field ion containment device;
mixing the gas-phase inert gas cations and the polypeptide anions so as to facilitate electron transfer from the anions to the cations, and thus inducing the cleavage of covalent bonds and production of negative electron transfer fragment and/or dissociation product anions; and mass (m/z) analyzing and detecting said negative electron transfer dissociation product ions or ions derived from negative electron transfer dissociation product ions.

35. The method of claim 34, wherein the mixing step includes simultaneously confining in a common region of the RF electric field containment device the cations and the multiply charged polypeptide anions.

* * * * *